(12) United States Patent
Runnels et al.

(10) Patent No.: US 11,565,064 B2
(45) Date of Patent: Jan. 31, 2023

(54) ARTICULATING STYLET

(71) Applicant: Through the Cords, LLC, Salt Lake City, UT (US)

(72) Inventors: Sean Runnels, Salt Lake City, UT (US); Wil Roberge, Salt Lake City, UT (US); Benjamin Fogg, Salt Lake City, UT (US)

(73) Assignee: Through the Cords, LLC, Salt Lake City, UT (US)

( * ) Notice: Subject to any disclaimer, the term of this patent is extended or adjusted under 35 U.S.C. 154(b) by 0 days.

(21) Appl. No.: 15/789,787

(22) Filed: Oct. 20, 2017

(65) Prior Publication Data

US 2018/0110950 A1 Apr. 26, 2018

Related U.S. Application Data

(60) Provisional application No. 62/411,265, filed on Oct. 21, 2016.

(51) Int. Cl.
*A61B 1/267* (2006.01)
*A61M 16/04* (2006.01)
(Continued)

(52) U.S. Cl.
CPC ....... *A61M 16/0488* (2013.01); *A61B 1/0051* (2013.01); *A61B 1/00078* (2013.01);
(Continued)

(58) Field of Classification Search
CPC ..................... A61M 16/04–0497; A61B 1/267
See application file for complete search history.

(56) References Cited

U.S. PATENT DOCUMENTS

| 4,244,362 A * | 1/1981 | Anderson ............. A61M 16/04 |
| | | 128/200.26 |
| 4,248,221 A * | 2/1981 | Winnard ............... A61M 16/04 |
| | | 128/207.15 |

(Continued)

FOREIGN PATENT DOCUMENTS

| JP | 08510666 A | 11/1996 |
| KR | 101100785 B1 | 1/2012 |

(Continued)

OTHER PUBLICATIONS

Patent Cooperation Treaty International Searching Authority; International Search Report & Written Opinion for PCT Patent Application No. PCT/US2017/057440 dated Feb. 7, 2018, 15 pages.

(Continued)

*Primary Examiner* — Eduardo C Robert
*Assistant Examiner* — Steven J Cotroneo
(74) *Attorney, Agent, or Firm* — Bochner IP, PLLC; Andrew D. Bochner

(57) ABSTRACT

An articulating stylet usable with a tracheal intubation system is disclosed. Methods for using the articulating stylet and systems that incorporate the articulating stylet are also disclosed. In some examples, a stylet adapted for mounting an endotracheal tube comprises a shaft and a control wire. The shaft comprises a distal shaft portion, a proximal shaft portion, and an expanding connection joining the distal shaft portion to the proximal shaft portion. The proximal shaft portion has a body portion and a tip portion. The tip portion includes a tip and has greater flexibility than the body portion. The control wire is at least partially disposed within both the distal shaft portion and the proximal shaft portion and is configured to cause the tip portion of the proximal shaft portion to deform.

12 Claims, 67 Drawing Sheets

(51) Int. Cl.
*A61M 16/00* (2006.01)
*A61B 1/05* (2006.01)
*A61B 1/06* (2006.01)
*A61B 1/00* (2006.01)
*A61B 1/233* (2006.01)
*A61B 1/005* (2006.01)

(52) U.S. Cl.
CPC .............. *A61B 1/05* (2013.01); *A61B 1/0676* (2013.01); *A61B 1/233* (2013.01); *A61B 1/267* (2013.01); *A61M 16/024* (2017.08); *A61M 16/0418* (2014.02); *A61B 1/00059* (2013.01); *A61M 2205/502* (2013.01); *A61M 2205/584* (2013.01)

(56) References Cited

U.S. PATENT DOCUMENTS

| | | | | |
|---|---|---|---|---|
| 5,247,927 | A * | 9/1993 | Kepp | A61L 29/041 128/207.14 |
| 5,758,656 | A * | 6/1998 | Schroeder | A61M 25/0147 600/585 |
| 5,791,338 | A * | 8/1998 | Merchant | A61M 16/0488 128/200.26 |
| 6,164,277 | A * | 12/2000 | Merideth | A61M 16/0488 128/207.14 |
| 6,668,832 | B2 * | 12/2003 | Hipolito | A61M 16/04 128/200.24 |
| 8,416,291 | B2 * | 4/2013 | Carrey | A61B 1/00039 348/77 |
| 8,746,239 | B2 | 6/2014 | Yoshida | |
| 9,199,051 | B2 * | 12/2015 | Booth | A61M 16/0488 |
| 9,364,628 | B2 * | 6/2016 | Hwang | A61M 16/04 |
| 2003/0154987 | A1 * | 8/2003 | Palmer | A61M 16/0672 128/207.14 |
| 2004/0210114 | A1 * | 10/2004 | Simon | A61B 1/00032 600/185 |
| 2007/0219499 | A1 * | 9/2007 | Hayakawa | A61M 25/0043 604/164.01 |
| 2012/0078050 | A1 | 3/2012 | Schwartz et al. | |
| 2013/0025588 | A1 * | 1/2013 | Bosel | A61M 16/0434 128/200.26 |
| 2014/0200405 | A1 * | 7/2014 | Atlas | A61M 16/0488 128/200.26 |
| 2014/0275772 | A1 | 9/2014 | Chuda | |
| 2015/0099935 | A1 * | 4/2015 | Runnels | A61M 16/0488 600/188 |
| 2015/0224273 | A1 * | 8/2015 | Booth | A61M 16/0418 128/200.26 |
| 2016/0220777 | A1 * | 8/2016 | Weaver | A61M 16/0488 |
| 2016/0279365 | A1 | 9/2016 | Esnouf | |

FOREIGN PATENT DOCUMENTS

| | | |
|---|---|---|
| WO | 2010065566 A2 | 6/2010 |
| WO | 2014011530 A1 | 1/2014 |

OTHER PUBLICATIONS

Extended European Search Report issued in European Patent Application No. 17861947 dated May 12, 2020, 10 pages.

* cited by examiner

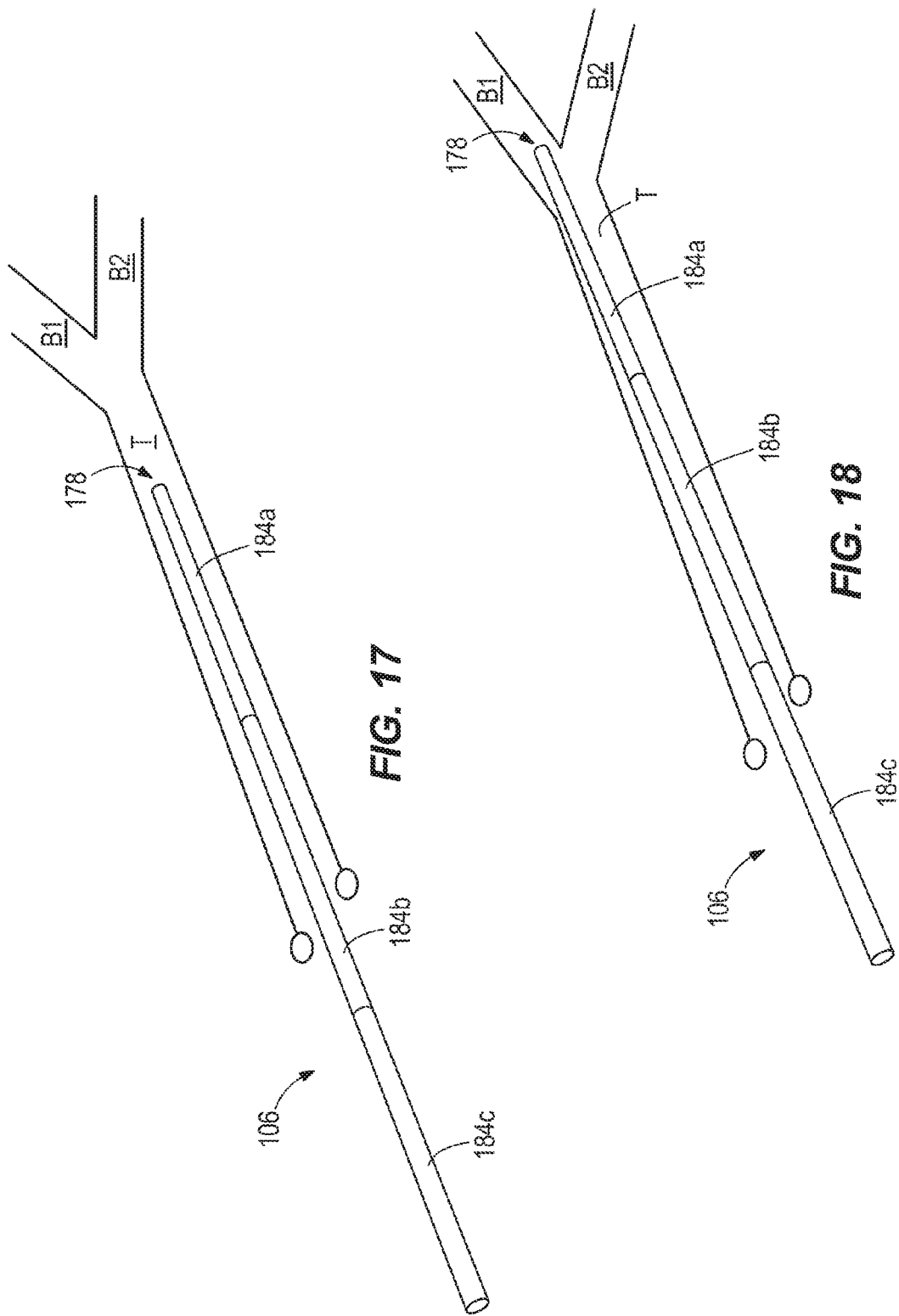

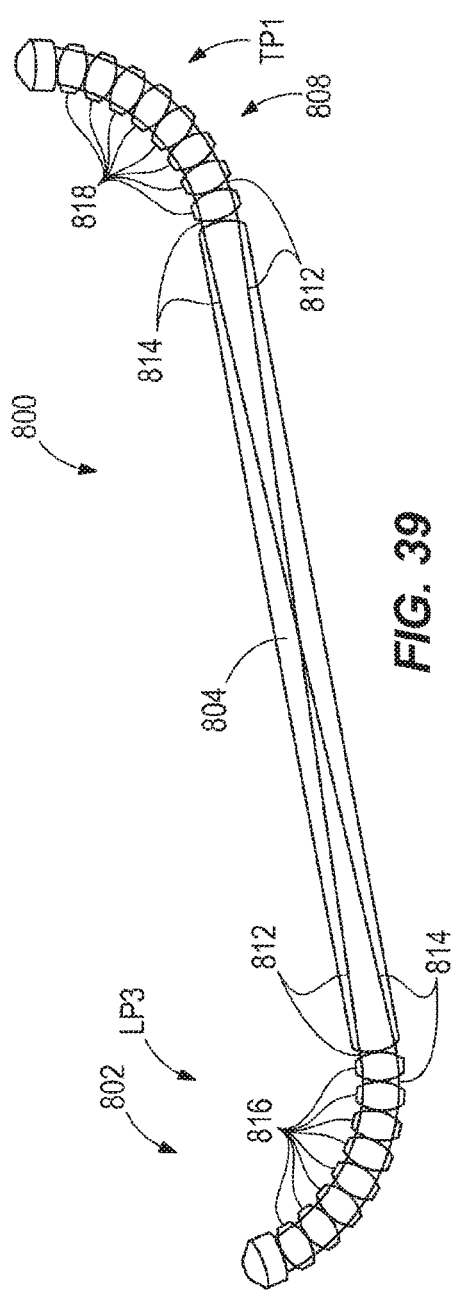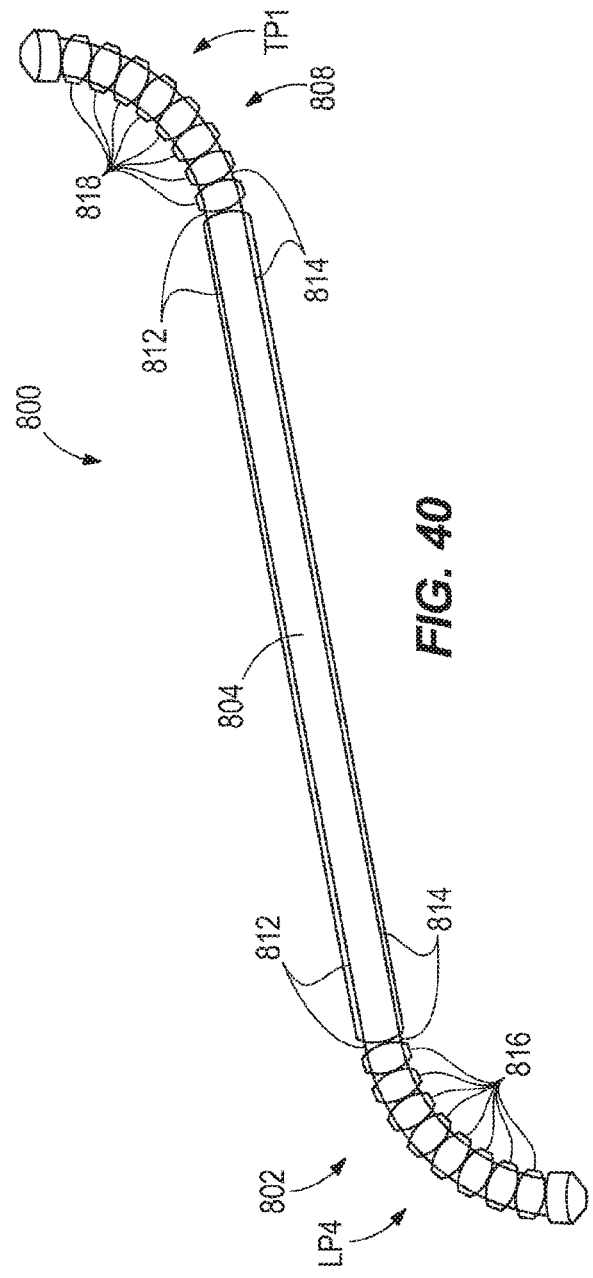

ARTICULATING STYLET

CROSS-REFERENCE TO RELATED APPLICATION

This application claims priority to U.S. Provisional Patent Application Ser. No. 62/411,265, filed Oct. 21, 2016, entitled "Articulating Stylet," the disclosure of which is hereby incorporated by reference in its entirety.

BACKGROUND

Many surgical procedures are typically performed while the patient is under general anesthesia. During these procedures, the patient is given a combination of medications to cause a loss of consciousness and muscle paralysis. The medications that cause loss of consciousness and muscle paralysis also interfere with the patient's ability to breath. Accordingly, patients often undergo tracheal intubation during these procedures so that the patient may be connected to an external ventilator or breathing circuit. Patients may also be intubated for nonsurgical conditions in which enhanced oxygen delivery is required. Tracheal intubation may also be used in other circumstances.

During tracheal intubation, an endotracheal tube is placed in the patient's airway. Generally, the endotracheal tube is advanced through the patient's nose or mouth into the patient's trachea. The endotracheal tube is then connected to an external ventilator or breathing circuit. The ventilator is then able to breath for the patient, delivering oxygen into the patient's lungs.

The patient's vocal cords and the space between them form the entrance to the trachea, these structures are also known as the glottis. The glottis is visible from and may be accessed through the pharynx. The pharynx is the portion of the upper airway that is located behind the patient's mouth and below the patient's nasal cavity. The mouth and the nasal cavity meet in the pharynx. Additionally, the esophagus and the glottis may be accessed through the pharynx. During the intubation process, the endotracheal tube must be carefully advanced through the patient's pharynx and placed through the vocal cords into the trachea.

The intubation process interferes with the patient's ability to breathe and thus deliver oxygen to the body independently. If the patient is without oxygen for more than two or three minutes, tissue injury may occur, which can lead to death or permanent brain damage. Accordingly, the intubation process must be performed quickly and accurately.

SUMMARY

In general terms, this disclosure is directed to an articulating stylet for use with a tracheal intubation system. In one possible configuration and by non-limiting example, the tracheal intubation system allows a caregiver to properly position an endotracheal tube in a normal or difficult airway quickly, accurately, and safely. In another configuration and by non-limiting example, the tracheal intubation system allows a caregiver to properly perform an endotracheal tube exchange procedure quickly, accurately, and safely.

An aspect is a stylet adapted for mounting an endotracheal tube comprising: a shaft comprising: a distal shaft portion; a proximal shaft portion having a body portion and a tip portion, the tip portion including a tip and having greater flexibility than the body portion; and an expanding connection joining the distal shaft portion to the proximal shaft portion; and a control wire at least partially disposed within both the distal shaft portion and the proximal shaft portion and configured to cause the tip portion of the proximal shaft portion to deform.

Another aspect is a stylet adapted for mounting an endotracheal tube comprising: a shaft comprising a distal shaft portion, a proximal shaft portion having a body portion and a tip portion, the tip portion comprising a tip and having greater flexibility than the body portion, and an expanding connection joining the distal shaft portion to the proximal shaft portion, and a control wire at least partially disposed within both the distal shaft portion and the proximal shaft portion and configured to cause the tip portion of the proximal shaft portion to deform.

Another aspect is a method of positioning an endotracheal tube in a patient comprising: inserting a blade of a laryngoscope in a mouth of the patient, viewing a trachea of the patient with the laryngoscope, mounting the endotracheal tube on an articulating stylet, the articulating stylet comprising a shaft comprising a distal shaft portion, a proximal shaft portion having a body portion and a tip portion, the tip portion including a tip and having greater flexibility than the body portion, and a control wire at least partially disposed within both the distal shaft portion and the proximal shaft portion and configured to cause the tip portion of the proximal shaft portion to deform, inserting the stylet into an airway of the patient, viewing a tip of the stylet with the laryngoscope, articulating the tip of the stylet towards an entrance of the trachea, and sliding the endotracheal tube along the stylet and into the trachea of the patient.

DESCRIPTION OF THE DRAWINGS

FIG. 17 is a schematic view of an embodiment of the endotracheal tube of FIG. 6 disposed in the trachea of a patient.

FIG. 18 is another schematic view of an embodiment of the endotracheal tube of FIG. 6 disposed further into the trachea if a patient.

FIG. 39 is a side view of an embodiment of the articulating stylet of FIG. 19.

FIG. 40 is a side view of another embodiment of the articulating stylet of FIG. 19.

DETAILED DESCRIPTION

Figure 1:
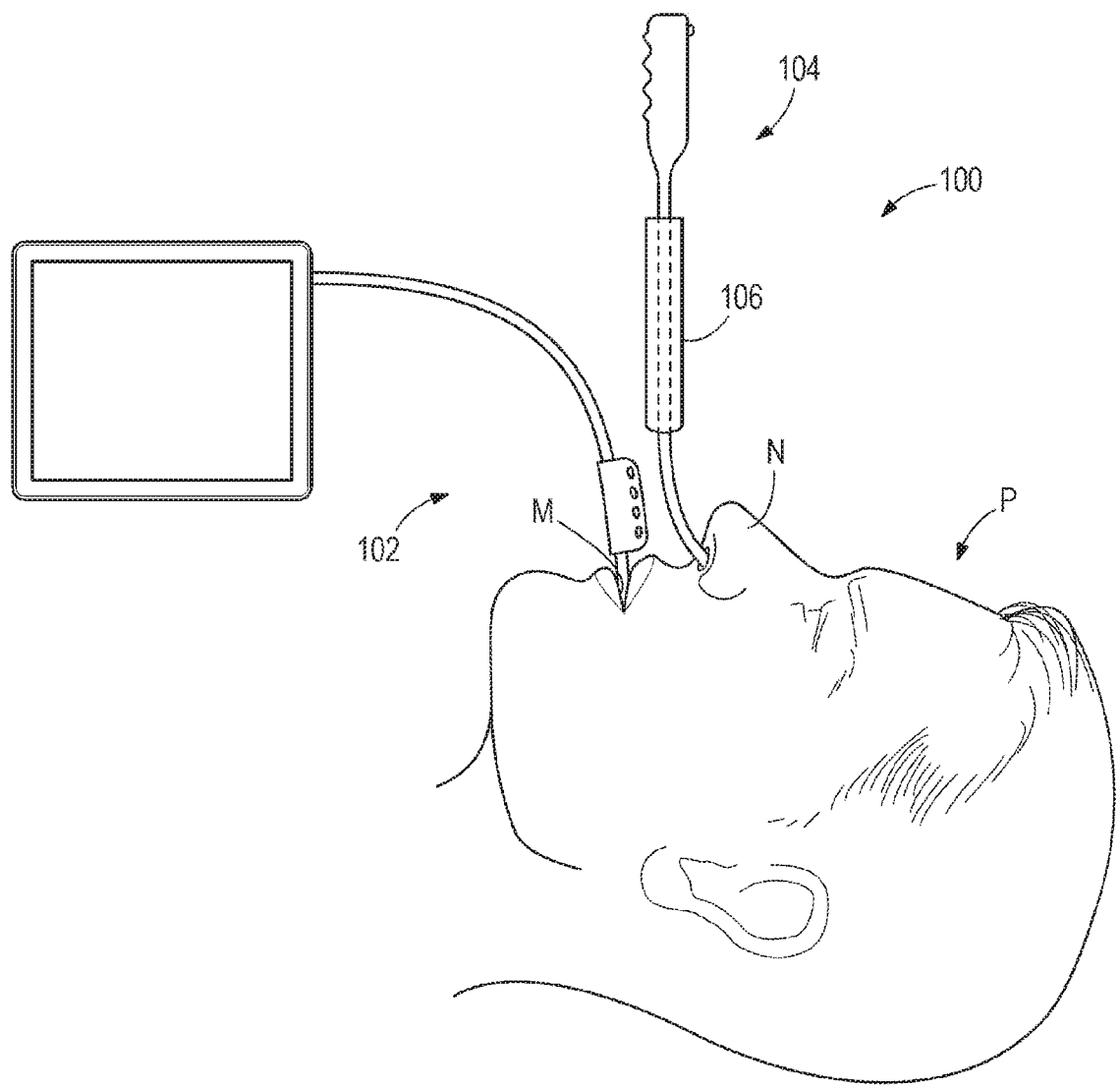
FIG. 1 is a diagram of an example tracheal intubation system including a laryngoscope being used to intubate a patient.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates generally to an articulating stylet that is usable with a tracheal intubation system. A stylet is a slender probe that is used to guide placement of an endotracheal tube or another device. Stylets are also sometimes referred to as introducers or catheters. This disclosure also relates to methods of performing tracheal intubation and endotracheal tube exchange procedures.

In some cases, the endotracheal tube of an intubated patient needs to be exchanged for a new endotracheal tube. One method for this exchange process involves placing a catheter or stylet through the existing endotracheal tube until the tip of the catheter or stylet enters the trachea. The existing endotracheal tube is then removed over the catheter or stylet, while the catheter or stylet is left in place. A new endotracheal tube is then placed over the catheter or stylet. The new endotracheal tube is then advanced over the catheter or stylet until the tip of the new endotracheal tube is properly placed in the trachea. The catheter or stylet is then removed from the patient. The new endotracheal tube is then connected to an external ventilator or breathing circuit. The ventilator is then able to breath for the patient, delivering oxygen into the patient's lungs.

Many potential complications may arise during endotracheal tube exchange procedures. For example, the tip of the catheter or stylet can cause tracheal and lung trauma, which can cause harm or death to the patient. Poor depth control of the tip of the catheter or stylet during the endotracheal tube exchange procedure is a contributing factor in this trauma to the trachea or lungs. An additional potential complication is the accidental removal of the tip of the exchange catheter or stylet from the trachea during the endotracheal tube exchange procedure. This can lead to the new endotracheal tube not entering the trachea, resulting in a failed endotracheal intubation and harm or death to the patient.

FIG. 1 is a diagram of an example tracheal intubation system 100 including a laryngoscope being used to intubate a patient P. The example intubation system 100 includes a laryngoscope 102, an articulating stylet 104, and an endotracheal tube 106. Also illustrated are the mouth M and the nose N of the patient P. In this example, the laryngoscope 102 is inserted into the mouth M of the patient P, the articulating stylet 104 is inserted into the nose N of the patient P, and the endotracheal tube 106 is mounted on the articulating stylet 104. Alternatively, the articulating stylet 104 is inserted into the mouth M of the patient P.

The patient P is a person or animal who is being intubated. Although the intubation system 100 is particularly useful to intubate a patient with a difficult airway, the intubation system 100 may also be used on a patient with a normal airway. Examples of patient P include adults, children, infants, elderly people, obese people, people with tumors affecting the head or neck, and people with unstable cervical spines. In some embodiments, the intubation system 100 may be used to intubate animals with normal or difficult airways. The intubation system 100 may be used to intubate other people or animals as well.

The laryngoscope 102 is a medical instrument configured to permit a caregiver to directly or indirectly view, among other things, the glottis of the patient P. In some embodiments, the laryngoscope 102 includes a blade with an integrated optical capture device and light source. In some embodiments, the blade is configured to be inserted through the mouth M of the patient P and positioned so that the glottis is in the field of view of the optical capture device. The image captured by the laryngoscope 102 is viewed from a position that is external to the patient P. In some embodiments, the image captured by the laryngoscope 102 is viewed on an external display device, such as a screen. The laryngoscope 102 is illustrated and described in more detail with reference to FIG. 2.

The articulating stylet 104 is a device that is inserted into the patent P's airway. In this example, the articulating stylet 104 is used to guide the placement of the endotracheal tube 106. The articulating stylet 104 includes a thin, flexible tube that may be directed and advanced into the airway of the patient P. The articulating stylet 104 includes a control mechanism that directs the tip of the articulating stylet 104.

The articulating stylet 104 may be configured to be viewed with the laryngoscope 102 during the intubation procedure. The articulating stylet 104 is illustrated and described in more detail throughout the application, including with reference to FIGS. 3-5 and 51-62.

In some embodiments, the endotracheal tube 106 is a hollow tube that is configured to be placed in the airway of the patient P. When the patient P is intubated, one end of the endotracheal tube 106 is disposed inside the trachea of the patient P and the other end is connected to an external ventilator or breathing circuit. The endotracheal tube 106 is configured to occlude the airway of the patient P. Thus, gases (e.g., room air, oxygenated gases, anesthetic gases, expired breath, etc.) may flow into and out of the trachea of the patient P through the endotracheal tube 106. In some embodiments, the endotracheal tube 106 may be connected to a breathing circuit, including for example a machine-powered ventilator or a hand-operated ventilator. In other embodiments, the patient P may breathe through the endotracheal tube 106 spontaneously. The endotracheal tube 106 is illustrated and described in more detail with reference to FIG. 6.

The endotracheal tube 106 is configured to be mounted on the articulating stylet 104 by sliding over the tip and along the shaft of the articulating stylet 104. After a caregiver has positioned the tip of the articulating stylet 104 in the trachea of the patient P, the endotracheal tube 106 is advanced over the shaft of the articulating stylet 104 and into the trachea of the patient P. In this manner, the articulating stylet 104 guides the endotracheal tube 106 into the proper location in the trachea of the patient P. The process of positioning the endotracheal tube 106 is illustrated and described in more detail with reference to FIGS. 7-16.

Figure 2:
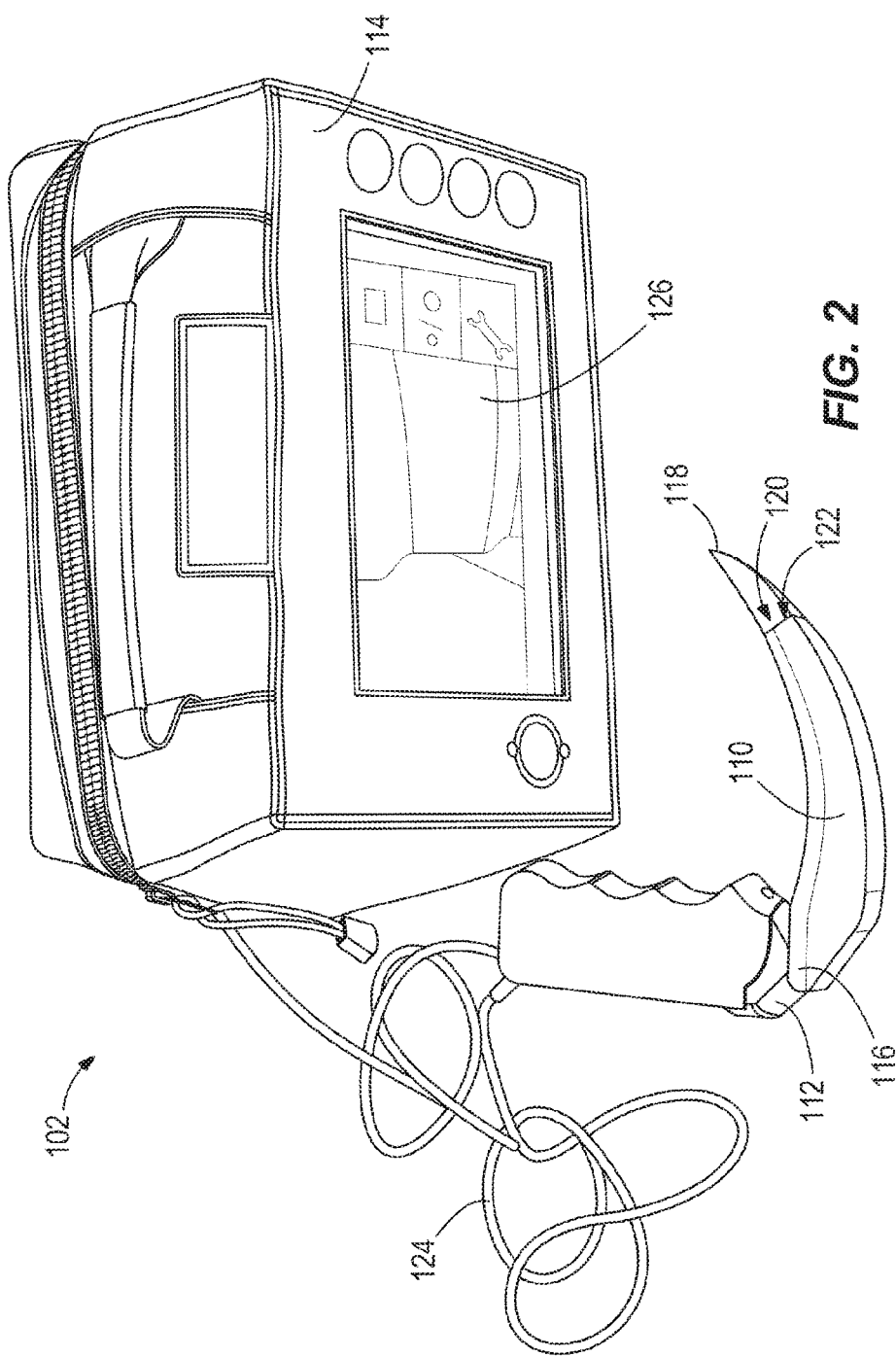
FIG. 2 is a perspective view of an example laryngoscope.

FIG. 2 is a perspective view of an example of the laryngoscope 102. In some embodiments, the laryngoscope 102 includes a blade 110, handle 112, and display device 114.

In some embodiments, the blade 110 is curved and has a first end 116 and a second end 118. The first end 116 is coupled to the handle 112. The second end 118 is configured to be inserted through the mouth of the patient and into the pharynx of the patient as illustrated and described with reference to FIG. 8. In some embodiments, the blade 110 is straight. In some embodiments, the cross section of the blade 110 is trough-like, while in other embodiments the cross section of the blade 110 is tubular. Yet other embodiments of the blade 110 are possible.

In some embodiments, the blade 110 includes an optical capture device 120 and light source 122. In some embodiments, the optical capture device 120 and the light source 122 are disposed near the second end 118 of the blade 110. Accordingly, when the blade 110 is inserted into the pharynx of the patient, the light source 122 illuminates the glottis of the patient and the optical capture device 120 captures an optical representation of the glottis of the patient, such as an image, a video, or light waves. In some embodiments, the blade 110 includes multiple optical capture devices 120 and light sources 122.

The optical capture device 120 is a device for capturing images. In some embodiments, the optical capture device 120 is a camera or image capture sensor, such as a charge-coupled device or complementary metal-oxide-semiconductor. In some embodiments, the optical capture device 120 is a digital video camera. In other embodiments, the optical capture device 120 is an optical fiber. In yet other embodiments, the optical capture device 120 is a mirror. Yet other embodiments of the optical capture device 120 are possible as well.

The light source 122 is a device that is configured to transmit or direct light towards the glottis. In some embodiments, the light source 122 is configured to generate light. In other embodiments, the light source 122 is configured to reflect light. Examples of the light source 122 include light emitting diodes, incandescent bulbs, optical fibers, and mirrors. Other embodiments include other light sources.

The handle 112 is coupled to the first end 116 of the blade 110 and is configured to be held in a hand of a user. The user may be an autonomous robot, a semi-autonomous robot, a robot remotely controlled by a medical professional, or a medical professional. The handle 112 operates to receive inputs from a caregiver and to adjust the position and orientation of the blade 110, and accordingly to aim the optical capture device 120 contained at the second end 118 thereof.

In some embodiments, the handle 112 has a cylindrical shape. In some embodiments, the cross section of the handle 112 is rectangular. In other embodiments, the cross section of the handle 112 is rectangular with rounded corners. In some embodiments, the handle 112 includes one or more molded finger grips. Other embodiments have other configurations of handle 112.

The display device 114 is configured to display, among other things, videos, images, or light waves that are captured by the optical capture device 120. In some embodiments, the display device 114 includes a screen 126. In some embodiments, the display device 114 is coupled to the handle 112 with a cable 124. In other embodiments, the display device 114 is formed integrally with the handle 112. In some embodiments, the display device 114 is a mirror. In some embodiments, a single mirror operates as both the display device 114 and the optical capture device 120. Yet other embodiments of display device 114 are possible.

In some embodiments, a cable 124 is disposed inside part or all of the handle 112, the blade 110, or both. In some embodiments, the cable 124 is configured to carry power to the optical capture device 120 and light source 122 and to carry electrical signals representing the video or images generated by the optical capture device 120 to the display device 114. In other embodiments, cable 124 is a fiber cable and operates to optically transmit light waves captured by the optical capture device 120 to the display device 114. Other embodiments do not include cable 124. For example, in some embodiments, video or images captured by the optical capture device 120 are transmitted wirelessly to the display device 114. In yet other embodiments, images captured by the optical capture device 120 are transmitted with one or more mirrors.

In some embodiments, the screen 126 is a liquid crystal display. In other embodiments, the screen 126 is a light-emitting diode display or cathode ray tube. In some embodiments, screen 126 is the surface of a mirror. Still other embodiments of the screen 126 are possible as well. The screen 126 operates to receive a signal representing an image and display that image.

Examples of the laryngoscope 102 include the GLIDE-SCOPE® video laryngoscope, manufactured by Verathon Inc. of Bothell, Wash., the VIVIDTRAC VT-A100® video intubation device, manufactured by Vivid Medical Inc. of Palo Alto, Calif., and the C-MAC® video laryngoscope, manufactured by Karl Storz GmbH & Co. KG of Tuttlingen, Germany. Other examples of laryngoscope 102 include other video laryngoscopes, fiberoptic bronchoscopes, fiberoptic stylets, mirror laryngoscopes, and prism laryngoscopes. There are many other examples of the laryngoscope 102 as well.

Figure 3:
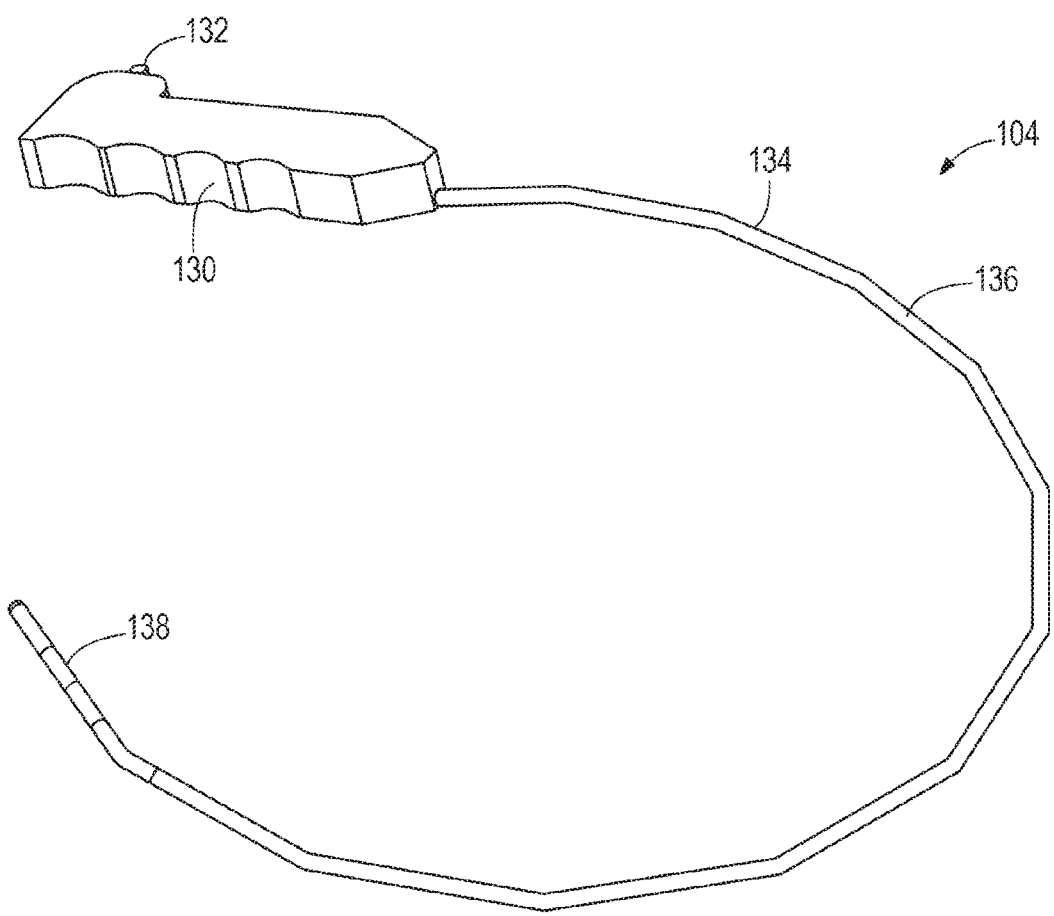
FIG. 3 is a perspective view of an example articulating stylet.

FIG. 3 is a perspective view of an example articulating stylet 104 configured to guide an endotracheal tube into the trachea of a patient. The articulating stylet 104 includes a handle 130 and a shaft 134. The handle 130 includes a tip control mechanism 132.

In some embodiments, the handle is configured to be held in a hand of a caregiver. In some embodiments, the handle 130 has a shape that fits comfortably in the hand of a caregiver. In some embodiments, the cross section of the handle 130 is cylindrical. In some embodiments, the cross section of the handle 130 is rectangular. In other embodiments, the cross section of the handle 130 is rectangular with rounded corners. In some embodiments, the handle 130 includes one or more molded finger grips.

The tip control mechanism 132 is configured to control the directional movement of the tip 138 of the shaft 134. In some embodiments, the tip control mechanism 132 is configured to be manipulated by a thumb of a caregiver. In other embodiments, the tip control mechanism 132 is configured to be manipulated by one or more fingers or the palm of a caregiver.

In some embodiments, the tip control mechanism 132 is a switch that has three physical positions. Each physical position corresponds to a movement instruction for the tip 138. For example, one physical position instructs the tip 138 to move or pivot in a first direction, a second physical position instructs the tip 138 to move or pivot in a second direction, and a third physical position instructs the tip 138 to remain stationary. In other embodiments, the tip control mechanism 132 may have fewer or more than three physical positions.

In some embodiments, the tip control mechanism 132 is a potentiometer and behaves in a manner similar to a joystick. In these embodiments, the tip 138 is articulated in a first direction by actuating the potentiometer in one direction and the tip 138 is articulated in a second direction by actuating the potentiometer in another direction. Depending on the magnitude of actuation of the potentiometer, the tip 138 may pivot to a greater or lesser degree. When the potentiometer is not actuated, the tip 138 is not articulated. In other embodiments, the tip control mechanism 132 is implemented with one or more buttons or touch sensors. When one of the buttons or touch sensors is activated, the tip 138 is articulated in a specific direction. In some embodiments, the tip control mechanism 132 is a wheel, trigger, or lever. Still other embodiments of tip control mechanism 132 are possible.

The shaft 134 includes an exterior surface 136 and a tip 138. The shaft 134 is configured to be inserted into the nose or mouth of a patient and directed through the glottis of the patient and into the trachea of the patient.

At an end opposite the tip 138, the shaft 134 is coupled to the handle 130. In some embodiments, the shaft 134 is between two to three feet in length and has a diameter of 3/16" of an inch. In other embodiments, especially those directed towards pediatric patients, the shaft 134 has a smaller diameter. Other embodiments, with smaller or greater lengths or smaller or greater diameters are possible as well.

In some embodiments, the shaft 134 has a tubular shape and is formed from a flexible material that is configured to adapt to the shape of the airway of the patient. In some embodiments, the cross-section of the shaft 134 has an oblong shape. Other embodiments of shaft 134 with other shapes are possible.

In some embodiments, the exterior surface 136 comprises a single, continuous, uniform material. In some embodiments, the exterior surface 136 has non-stick properties. For example, in some embodiments the exterior surface 136 is formed from polytetrafluoroethylene. In other embodiments, the exterior surface 136 is configured to receive a lubricant. Other embodiments of the exterior surface 136 are possible as well. Because the exterior surface 136 is formed from a continuous material, the exterior surface 136 does not have any seams. Accordingly, the exterior surface 136 can be quickly and inexpensively cleaned. For example, the exterior surface 136 may be sterilized without the use of expensive and time-consuming sterilization equipment (e.g., an autoclave).

In some embodiments, the tip 138 is configured to move or pivot independently from the remainder of shaft 134. In some embodiments, the tip 138 is configured to minimize trauma as it moves through the nose or mouth into the upper airway and advances into the trachea of the patient. In some embodiments, the tip 138 is contained within the exterior surface 136. In some embodiments, the tip 138 has a blunt rounded shape. In some embodiments, the tip 138 does not have edges, corners, or crevices that may potentially injure the patient. Still other embodiments of the tip 138 are possible.

In some embodiments the shaft 134 and tip 138 do not contain, and are free of, a camera, light source, or other mechanism to illuminate or capture images of the patient. Accordingly, in some embodiments the design of the exterior surface 136 of the shaft 134 and tip 138 is designed to reduce trauma and simplify sterilization. The design of the exterior surface 136 of the shaft 134 and tip 138 is not constrained by the requirements of a camera, light source, or optical fibers, such as lenses, heating elements for defogging, and lumens for directing water or suctioning to clear the field of view.

Figure 4:
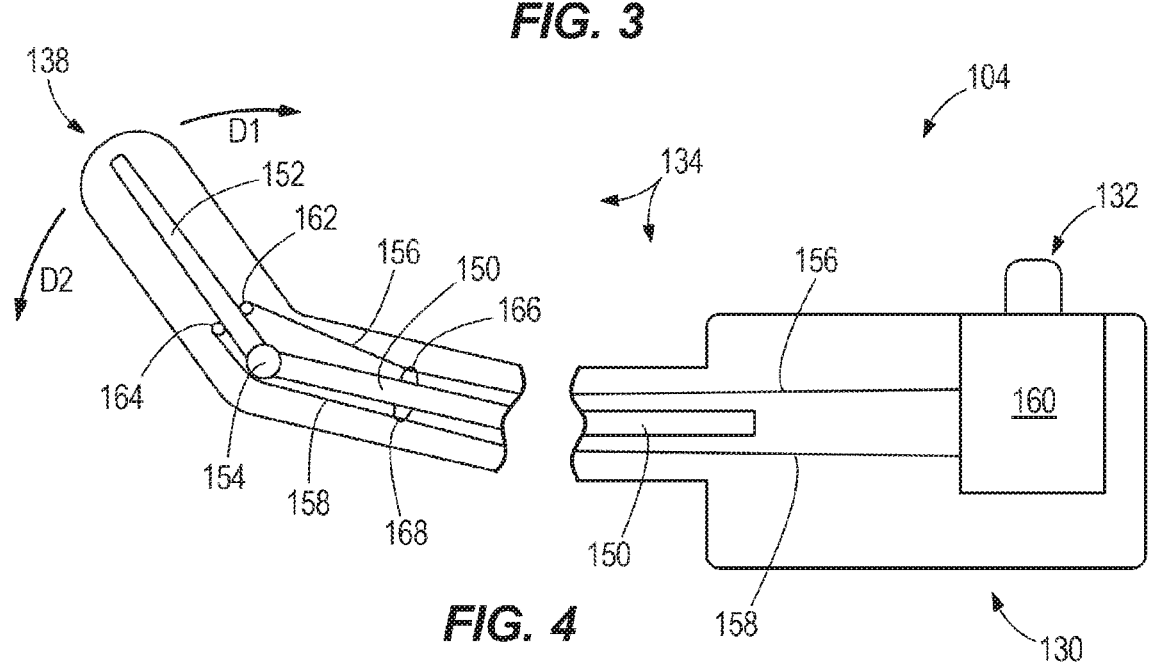
FIG. 4 is a cross-sectional view of the articulating stylet of FIG. 3.

FIG. 4 is a cross-sectional view of an example of the articulating stylet 104. The articulating stylet 104 includes a shaft 134 and a handle 130. In some embodiments, the shaft 134 includes a first segment 150, a second segment 152, a pivotable portion 154, a first cable 156, and a second cable 158, all of which are contained within the exterior surface 136. The handle 130 includes a tip control mechanism 132 and cable control mechanism 160.

The first segment 150 is coupled to the handle 130 on one end and the pivotable portion 154 on the other end. The first segment 150 is contained within the exterior surface 136. In some embodiments, the first segment 150 is formed of a flexible material. In other embodiments, the first segment 150 is formed from a semi-rigid material. In some embodiments, the first segment 150 is formed from a shape memory material. In these examples, the first segment 150 has a bias towards straightening out and the flexibility to bend to adapt to the anatomy of the airway of the patient. In some embodiments, the first segment 150 is formed from a flexible spring. Yet other embodiments of first segment 150 are possible as well.

The second segment 152 is coupled to the pivotable portion 154 on one end and forms the tip 138 with the other end. The second segment 152 is contained within the exterior surface 136. In some embodiments, the second segment 152 is formed from a rigid material, such as a metal, plastic, composite, or a combination thereof. In other embodiments, second segment 152 is formed from a rigid or semi-rigid material. In some embodiments, second segment 152 is formed from the same material as first segment 150.

The pivotable portion 154 is coupled to the first segment 150 and the second segment 152. The pivotable portion 154 is configured to pivot about one or more axes. In some embodiments, the pivotable portion 154 is a hinge. In other embodiments, the pivotable portion 154 is a joint, such as a ball and socket joint. In yet other embodiments, some or all of the shaft 134 is formed from a spring and the pivotable portion 154 is formed from a spring that is loosely wound relative to adjacent portions of the spring.

In some embodiments, the pivotable portion 154 is configured to allow second segment 152 to pivot about an axis between negative 90 degrees and positive 90 degrees. In other embodiments, pivotable portion 154 is configured to allow second segment 152 to pivot about an axis by more or fewer degrees.

In some embodiments, the pivotable portion 154 is configured to allow the second segment 152 to pivot about an axis in a single plane. In other embodiments, the pivotable portion 154 is configured to allow the second segment 152 to move about axes in multiple planes or even to move freely in any direction. However, in other embodiments the shaft 134 does not include the second segment 152, the pivotable portion 154, the first cable 156, and the second cable 158. Accordingly, in these embodiments, the tip 138 does not articulate.

In some embodiments, the second segment 152 includes a first cable connection point 162 and a second cable connection point 164. The first cable connection point 162 and second cable connection point 164 are disposed at or near the same distance longitudinally along the second segment 152 but on or near opposite sides radially of second segment 152. In some embodiments, the first segment 150 includes a first eyelet 166 and a second eyelet 168. In some embodiments, the first eyelet 166 and the second eyelet 168 are circular apertures.

In some embodiments, one end of the first cable 156 is connected to the first cable connection point 162 and one end of the second cable 158 is connected to the second cable connection point 164. The opposite ends of the first cable 156 and the second cable 158 are connected to the cable control mechanism 160. In some embodiments, the first cable 156 passes through first eyelet 166 and the second cable 158 passes through the second eyelet 168.

In some embodiments, the cable control mechanism 160 operates in a first mode, a second mode, and a third mode. In the first mode, the cable control mechanism 160 pulls the first cable 156 and relaxes the second cable 158 causing the second segment 152 to pivot in a direction D1. In the second mode, the cable control mechanism 160 relaxes the first cable 156 and pulls the second cable 158 causing the second segment 152 to pivot in a direction D2. In the third mode, the cable control mechanism 160 neither pulls nor relaxes the first cable 156 and neither pulls nor relaxes the second cable 158 leaving the second segment 152 in its current position. In some embodiments, tip control mechanism 132 is configured to select the mode of the cable control mechanism 160. In some embodiments, there are more or fewer cables are there are more or fewer modes. Other embodiments use completely different methods of moving or pivoting the tip 138. For example, in some embodiments, a motor is disposed in the shaft 134 near the tip 138 to pivot the second segment 152.

Although the embodiment shown in FIG. 4 includes two segments and one pivotable portion, other embodiments with additional segments and pivotable portions are possible as well. In some of these embodiments, the shaft 134 also includes additional cables, cable connection points, and eyelets.

Figure 5:
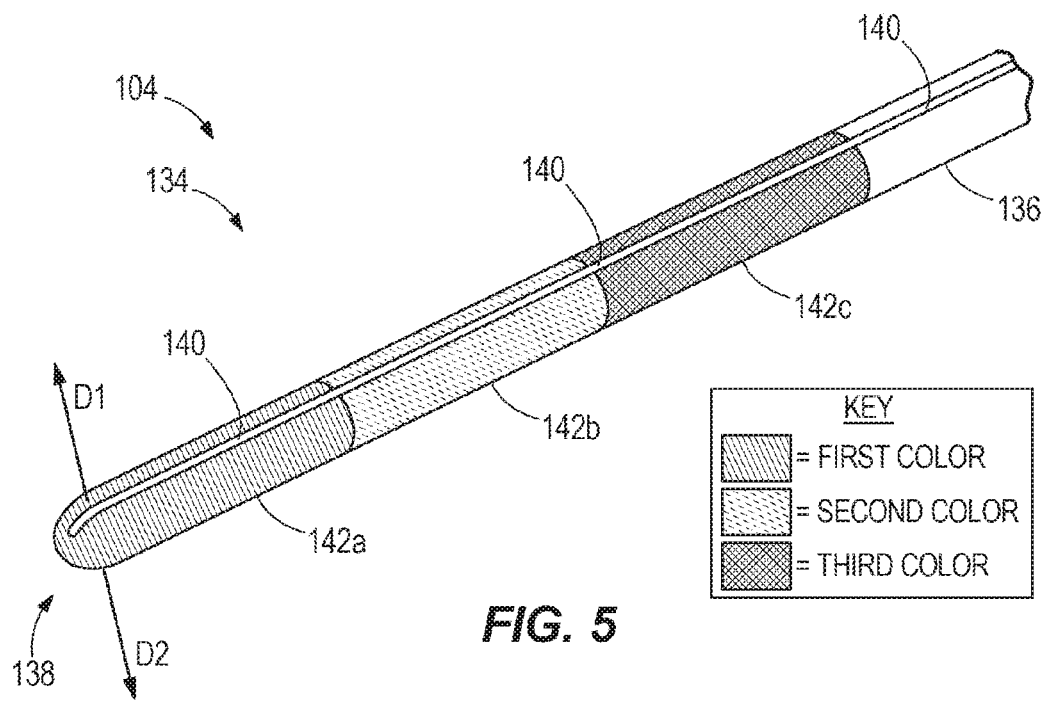
FIG. 5 is a perspective view of the tip of the articulating stylet of FIG. 3.

FIG. 5 is a perspective view of the tip 138 of an example articulating stylet 104. The tip 138 includes an orientation mark 140 and one or more depth-assessment bands 142*a-c* (collectively depth-assessment bands 142).

The orientation mark 140 is an indicator that is on or visible through the exterior surface 136 and is configured to be visible when the articulating stylet 104 is viewed with the laryngoscope 102. The orientation mark 140 is configured to convey information about the radial orientation of the articulating stylet 104. In some embodiments, the orientation mark 140 is a straight line that starts at or near the end of tip 138 and continues longitudinally along the length of shaft 134. In some embodiments, the orientation mark 140 is present throughout the entire length of the shaft 134. In other embodiments, the orientation mark 140 is only present along a portion of the shaft 134. In some embodiments, the orientation mark 140 is radially aligned with the direction D1, in which the tip 138 is configured to move. In this manner, a caregiver is able to view the orientation mark 140 on the display device of the laryngoscope 102 to determine the direction the tip 138 will move if it is pivoted. Thus, a caregiver is able to quickly direct the articulating stylet 104 into the trachea of the patient without erroneously pivoting the tip 138, which may result in delay or trauma to the patient.

In some embodiments, the orientation mark 140 is a dashed line or a series of dots. In some embodiments, the orientation mark 140 is not radially aligned with the direction D1 but still conveys the orientation information necessary for a caregiver to direct the articulating stylet 104. In some embodiments, multiple orientation marks are included. Yet other embodiments are possible as well.

In some embodiments, the articulating stylet 104 includes one or more depth-assessment bands 142. In the embodiment shown in FIG. 5, the articulating stylet 104 includes a first depth-assessment band 142*a*, second depth-assessment band 142*b*, and a third depth-assessment band 142*c*. The depth-assessment bands 142 are visual indicators that are on or visible through the exterior surface 136 and are configured to be visible when the articulating stylet 104 is viewed with the laryngoscope 102. The depth-assessment bands 142 are configured to convey information about the placement of the articulating stylet 104 relative to the anatomical landmarks of the patient, such as the vocal cords, that are also visible through the laryngoscope 102. The depth-assessment bands 142 are also configured to convey information about the longitudinal distance to the end of the tip 138.

Adjacent depth-assessment bands 142 are visually distinct from each other so that a caregiver who views a part of one of the depth-assessment bands 142 from the laryngoscope is able to identify specifically which of the depth-assessment bands 142 is in the field of view. Because the depth-assessment bands 142 are continuous regions, it is not necessary for a caregiver to advance or retract the articulating stylet 104 to bring one of the depth-assessment bands 142 into the field of view of the laryngoscope 102, which would create a risk of trauma to the patient or inadvertent removal of the articulating stylet 104 from the trachea of the patient. Nor does a caregiver need to remember or count the depth-assessment bands 142 as they pass through the field of view. In this manner, the depth-assessment bands 142 minimize trauma to the patient and allow a caregiver to focus on using the articulating stylet 104 rather than counting depth-assessment bands 142. Further, using the depth-assessment bands 142 in this manner may reduce the time necessary to complete a tracheal intubation procedure.

In some embodiments, the depth-assessment bands 142 are continuous regions of color that extend along a portion of the length of the shaft 134. For example, the first depth-assessment band 142a is a first color, the second depth-assessment band 142b is a second color, and the third depth-assessment band 142c is a third color. In other embodiments, the depth-assessment bands 142 are continuous regions of visually distinct patterns rather than colors. In some embodiments, the depth-assessment bands 142 include both visually distinct patterns and colors. Yet other embodiments are possible as well.

In some embodiments, the lengths of the depth-assessment bands 142 are selected based on the clinical precision required for the intubation procedure in which the articulating stylet 104 is intended and the distance into the trachea of the patient, a caregiver wishes to insert the tip 138. For example, a caregiver may wish to insert the tip 138 two to four centimeters into the trachea of an adult patient. In some embodiments for adult patients, the length of each of the depth-assessment bands 142 is two centimeters. In this manner, the caregiver will know that the tip 138 is properly inserted into the trachea of the patient when any part of the second depth-assessment band 142b is aligned with the entrance of the trachea of an adult patient (i.e., the patient's vocal cords).

Similarly, in some embodiments for pediatric patients, the lengths of the depth-assessment bands 142 are adapted to the shorter tracheas of those pediatric patients. For example, a caregiver may wish to insert the tip 138 one to two centimeters into the trachea of the pediatric patient. In some embodiments for pediatric patients, the length of each depth-assessment band 142 is one centimeter. In this manner, the caregiver will know that the tip 138 is properly inserted into the trachea of the patient when any part of the second depth-assessment band 142b is aligned with the entrance of the trachea of a pediatric patient (i.e., the patient's vocal cords).

In some embodiments, the colors of the depth-assessment bands 142 convey information about whether the tip 138 is properly positioned. In some example embodiments, the first depth-assessment band 142a is yellow, the second depth-assessment band 142b is green, and the third depth-assessment band 142c is red. The yellow color of the first depth-assessment band 142a may convey to a caregiver to use caution in advancing the tip 138 because it is not yet properly positioned. The green color of the second depth-assessment band 142b may convey success to a caregiver because the tip 138 appears to be properly positioned. The red color of the third depth-assessment band 142c may convey warning to a caregiver because the tip 138 may be positioned too deeply in the trachea of the patient, potentially causing trauma.

Although the embodiment shown in FIG. 5 includes three depth-assessment bands 142, other embodiments that include fewer or more depth-assessment bands 142 are possible as well. In some embodiments, the depth-assessment bands 142 are uniform in length. In other embodiments, one or more of the depth-assessment bands 142 has a different length than the other depth-assessment bands 142. For example, in applications requiring great precision, one of the depth-assessment bands 142 is shorter in length than the other depth-assessment bands 142. Accordingly, when that one of the depth-assessment bands 142 is aligned with the entrance to the trachea of a patient (i.e., the vocal cords), a caregiver is able to determine the depth of the tip 138 with greater precision.

Although the embodiment of the depth-assessment bands 142 shown in FIG. 5 relates to an articulating stylet 104, the depth-assessment bands 142 can also be used with other stylets. For example, in some embodiments, the depth-assessment bands 142 are used with a stylet that does not articulate. In these embodiments, the stylet is similar to the articulating stylet 104 described herein, except that the tip does not articulate and the components that control the tip are not included. In these embodiments, the stylet still includes the depth-assessment bands 142, which can be viewed with the laryngoscope 102 to determine the position of the non-articulating tip of the stylet relative to various anatomical landmarks.

Although the embodiments described herein relate to placement of an endotracheal tube, the depth-assessment bands are not limited to use in airway devices. In some embodiments, the depth-assessment bands 142 are included on other medical devices to guide the proper placement of those medical devices as well. For example, in some embodiments, the depth-assessment bands 142 are included in central venous catheters, endoscopic devices, devices placed in the gastrointestinal tract, devices placed inside the cardiovascular system, devices placed inside the urinary system, devices placed inside of the ears, devices placed inside of the eyes, devices placed in the central nervous system, devices placed inside of the abdomen, devices placed inside the chest, or devices placed inside the musculoskeletal system. In these embodiments, the depth-assessment bands 142 are configured to be compared to various tissue structures. In these embodiments, the depth-assessment bands 142 are configured to convey information about the placement of the device relative to various anatomical landmarks compared to other organ systems inside the body or even outside of the body. Additionally, in some embodiments, the depth-assessment bands 142 are included on non-medical devices in which depth control is desired. For example, the depth-assessment bands 142 can be included in industrial devices, such as devices for the inspection of machinery or physical structures, and devices for the proper placement of fasteners or other industrial or physical parts.

Figure 6:
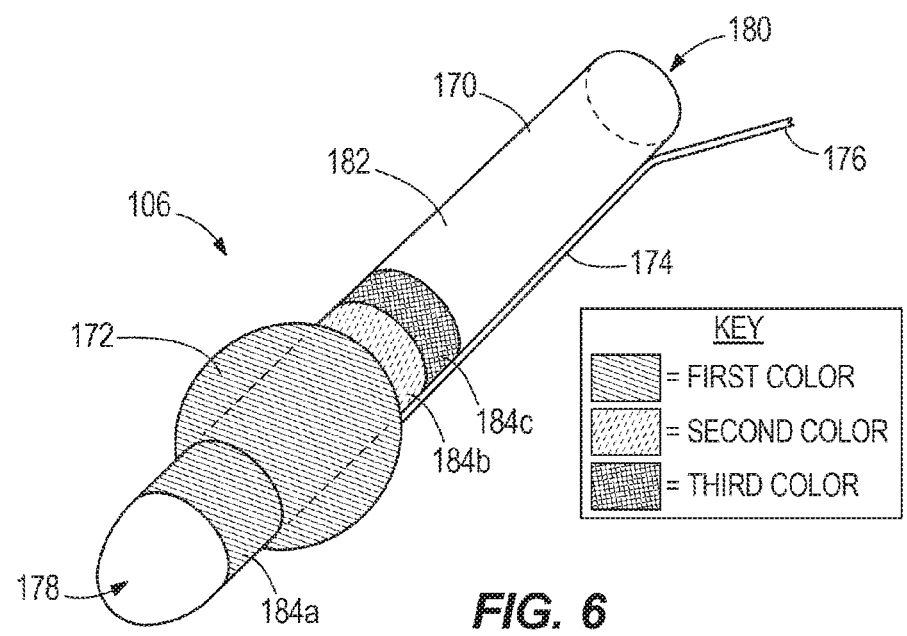
FIG. 6 is a perspective view of an example endotracheal tube.

FIG. 6 is a perspective view of an example endotracheal tube 106. The endotracheal tube 106 includes a pipe 170, a cuff 172, and an inflation lumen 174. In some embodiments, the endotracheal tube 106 does not include the cuff 172 or the inflation lumen 174.

In some embodiments, the pipe 170 is hollow and includes a first end 178, a second end 180, and an exterior surface 182. In some embodiments, the pipe 170 is formed from a flexible material and operates to adapt to the anatomy of the patient. For example, in some embodiments, the pipe 170 is formed from polyvinyl chloride. In other embodiments, the pipe 170 is formed from silicone rubber or latex rubber. In some embodiments, the pipe 170 is formed from a rigid or semi-rigid material, such as stainless steel.

The pipe 170 operates as a passage for gases to enter and exit the trachea of the patient. The pipe 170 also operates to protect the lungs of the patient from stomach contents. Further, in some embodiments, the pipe 170 operates as a passage to suction the trachea and lungs of the patient. The first end 178 is configured to be advanced into the trachea of the patient. The second end 180 is configured to be connected to a ventilator or breathing circuit.

In some embodiments, the cuff 172 is disposed on the exterior surface 182 of the pipe 170 near the first end 178. The cuff 172 is configured to form a seal between the exterior surface 182 of the pipe 170 and the trachea of the patient. In this manner, the cuff 172 prevents gases and liquids from entering or exiting the trachea of the patient without passing through the pipe 170. In addition, the cuff 172 secures the position of the endotracheal tube 106 in the trachea of the patient. In some embodiments, the cuff 172 is an inflatable chamber. For example, in some embodiments, the cuff 172 is a balloon. Yet other embodiments of the cuff 172 are possible as well.

The inflation lumen 174 includes an inflation port 176. The inflation lumen 174 is connected to the cuff 172 and operates as a channel for the entry of fluid into the cuff 172. The inflation port 176 is configured to receive a fluid. In some embodiments, the inflation port 176 is configured to receive a syringe that operates to expel fluid through the inflation lumen 174 and into the cuff 172. In this manner, the cuff 172 can be inflated to seal the trachea of the patient.

In some embodiments, the endotracheal tube 106 is formed from a transparent or translucent material that allows the articulating stylet 104 to be seen there through. In some embodiments, the endotracheal tube 106 includes one or more depth-assessment bands 184a-c (collectively depth-assessment bands 184). In the embodiment shown in FIG. 6, the example endotracheal tube 106 includes a first depth-assessment band 184a, second depth-assessment band 184b, and a third depth-assessment band 184c. The depth-assessment bands 184 are indicators that are on or visible through the exterior surface 182 and are configured to be visible when the articulating stylet 104 is viewed with the laryngoscope 102. The depth-assessment bands 184 are configured to convey information about the placement of the endotracheal tube 106 relative to the anatomical landmarks of the patient, such as the vocal cords, that are also visible through the laryngoscope 102. The depth-assessment bands 184 are also configured to convey information about the longitudinal distance to the end of the first end 178.

Adjacent depth-assessment bands 184 are visually distinct from each other so that a caregiver who views a part of one of the depth-assessment bands 184 from the laryngoscope 102 is able to identify which specific one of the depth-assessment bands 184 is in the field of view. Because the depth-assessment bands 184 are continuous regions, it is not necessary for a caregiver to advance or retract the endotracheal tube 106 to bring the depth-assessment bands 184 into the field of view of the laryngoscope 102, which would create a risk of trauma to the patient or inadvertent removal of the endotracheal tube 106 from the trachea of the patient. Nor does a caregiver need to remember or count the depth-assessment bands 184 as they pass through the field of view. In this manner, the depth-assessment bands 184, minimize trauma to the patient and allow a caregiver to focus on advancing the endotracheal tube 106 rather than counting depth-assessment bands 184. Further, using the depth-assessment bands 184, in this manner may reduce the time necessary to complete a tracheal intubation procedure.

In some embodiments, the depth-assessment bands 184 are continuous regions of color that extend along a portion of the length of the pipe 170. For example, the first depth-assessment band 184a is a first color, the second depth-assessment band 184b is a second color, and the third depth-assessment band 184c is a third color. In other embodiments, the depth-assessment bands 184 are continuous regions of visually distinct patterns rather than colors. In some embodiments, the depth-assessment bands 184 include both visually distinct patterns and colors. In addition, in some embodiments, one or more of the depth-assessment bands 184 may include part or all of cuff 172. Yet other embodiments of the depth-assessment bands 184 are possible as well.

In some embodiments, the lengths of the depth-assessment bands 184 are selected based on the clinical precision required for the intubation procedure in which the endotracheal tube 106 is intended and the distance into the trachea of the patient, a caregiver wishes to insert the first end 178. For example, a caregiver may wish to insert the first end 178 two to four centimeters into the trachea of an adult patient. In some embodiments for adult patients, the length of each of the depth-assessment bands 184 is two centimeters. In this manner, the caregiver will know that the first end 178 is properly inserted into the trachea of the patient when any part of the second depth-assessment band 184b is aligned with the entrance of the trachea of an adult patient (i.e., the patient's vocal cords).

Similarly, in some embodiments for pediatric patients, the lengths of the depth-assessment bands 184 are adapted to the shorter tracheas of those pediatric patients. For example, a caregiver may wish to insert the first end 178 one to two centimeters into the trachea of the pediatric patient. In some embodiments for pediatric patients, the length of each of the depth-assessment bands 184 is one centimeter. In this manner, the caregiver will know that the first end 178 is properly inserted into the trachea of the patient when any part of the second depth-assessment band 184b is aligned with the entrance of the trachea of a pediatric patient (i.e., the patient's vocal cords).

In some embodiments, the colors of the depth-assessment bands 184 convey information about whether the first end 178 is properly positioned. In some example embodiments, the first depth-assessment band 184a is yellow, the second depth-assessment band 184b is green, and the third depth-assessment band 184c is red. The yellow color of the first depth-assessment band 184a may convey to a caregiver to use caution in advancing the first end 178 because it is not yet properly positioned. The green color of the second depth-assessment band 184b may convey success to a caregiver because the first end 178 appears to be properly positioned. The red color of the third depth-assessment band 184c may convey warning to a caregiver because the first end 178 may be positioned too deeply in the trachea of the patient, potentially causing trauma.

Although the embodiment shown in FIG. 6 includes three depth-assessment bands 184, other embodiments that include fewer or more depth-assessment bands 184 are possible as well. In some embodiments, the depth-assessment bands 184 are uniform in length. In other embodiments, one or more of the depth-assessment bands 184 has a different length than the other depth-assessment bands 184. For example, in applications requiring great precision, one of the depth-assessment bands 184 is shorter in length than the other depth-assessment bands 184. Accordingly, when that one of the depth-assessment bands 184 is aligned with the entrance to the trachea of a patient (i.e., the vocal cords), a caregiver is able to determine the depth of the first end 178 with greater precision.

Figure 7:
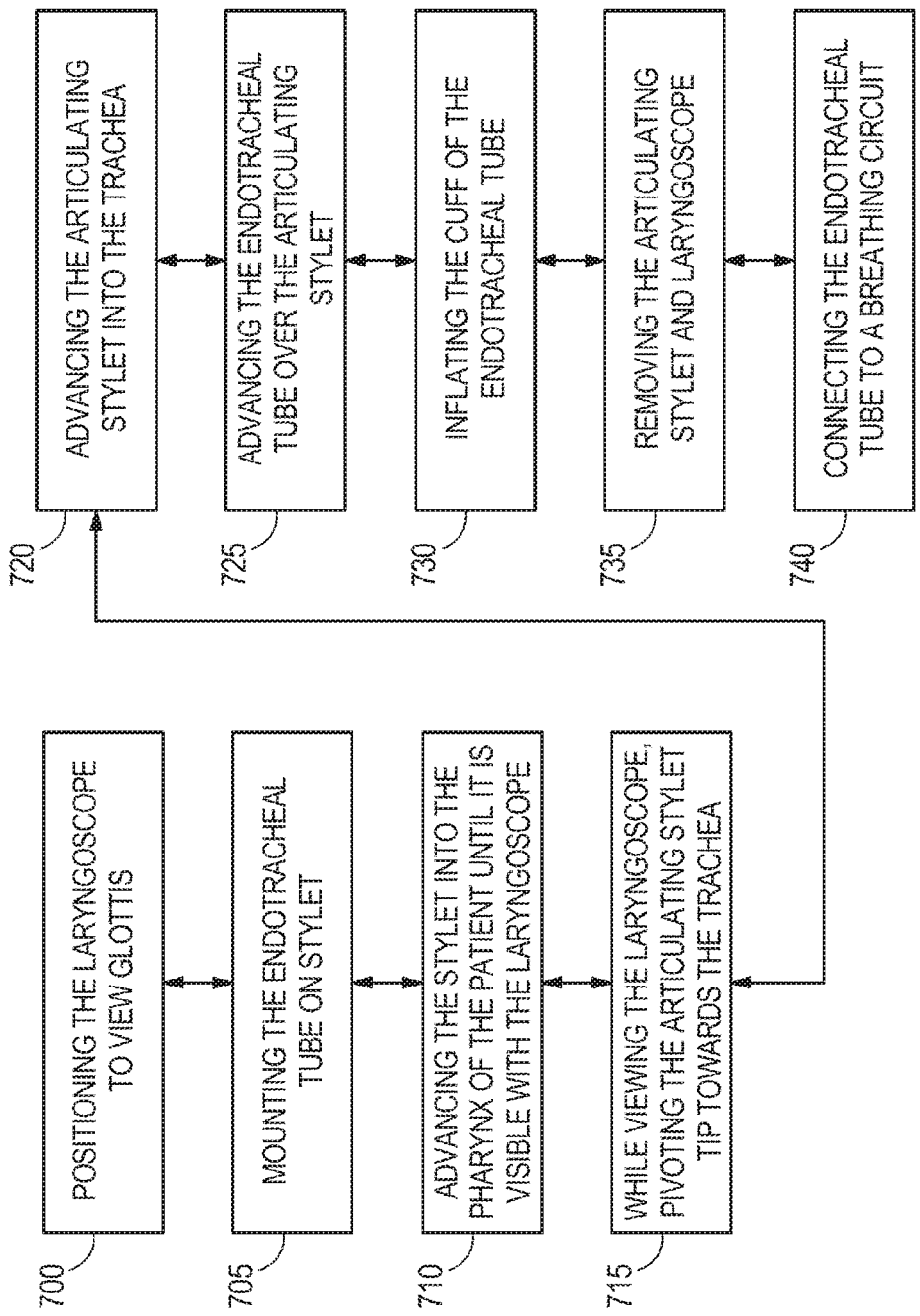
FIG. 7 is a flowchart of an example process of placing an endotracheal tube in a patient using an example tracheal intubation system including a laryngoscope.

FIG. 7 is a flowchart of an example process of positioning an endotracheal tube in a patient using an example tracheal intubation system including a laryngoscope. In some embodiments, the articulating stylet includes a handle, a flexible shaft, and a blunt, rounded tip that is directed by a control mechanism on the handle.

Figure 8:
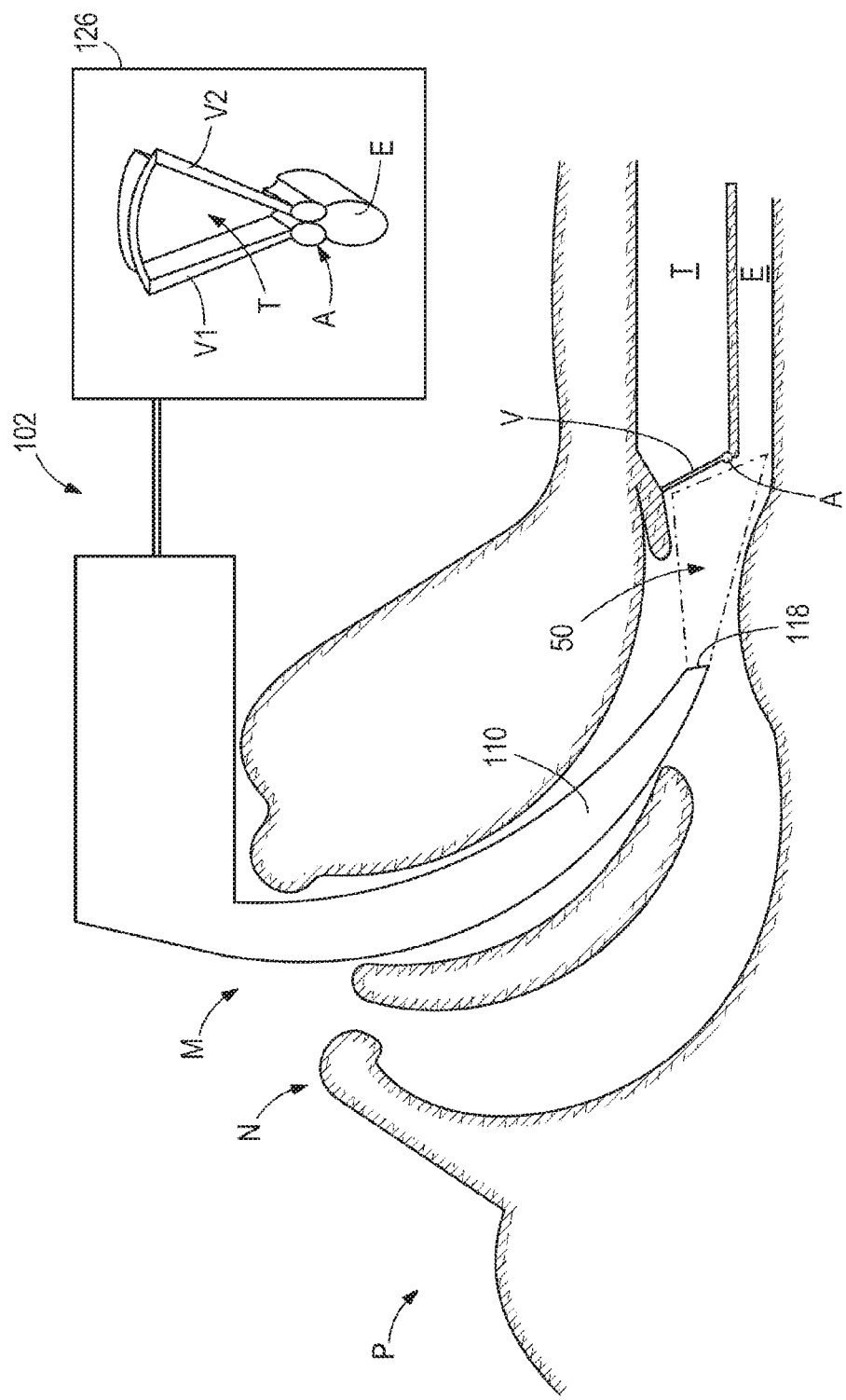
FIG. 8 is a cross-sectional view of a patient after a laryngoscope is positioned to view the glottis during an intubation procedure using an example tracheal intubation system including a laryngoscope.

Initially, at step 700, the laryngoscope is positioned to view the glottis of the patient. In some embodiments, the laryngoscope is inserted through the mouth of the patient. In other embodiments, the laryngoscope is inserted through the nose of the patient. A caregiver, usually a physician or a person assisting a physician, grips the handle of the laryngoscope and maneuvers the handle to position the blade so that the optical capture device of the laryngoscope has a clear view of the glottis of the patient. In some embodiments, the caregiver verifies that the laryngoscope is properly positioned by checking the screen of the display device of the laryngoscope. The field of view of the laryngoscope is best seen in FIG. 8.

Figure 9:
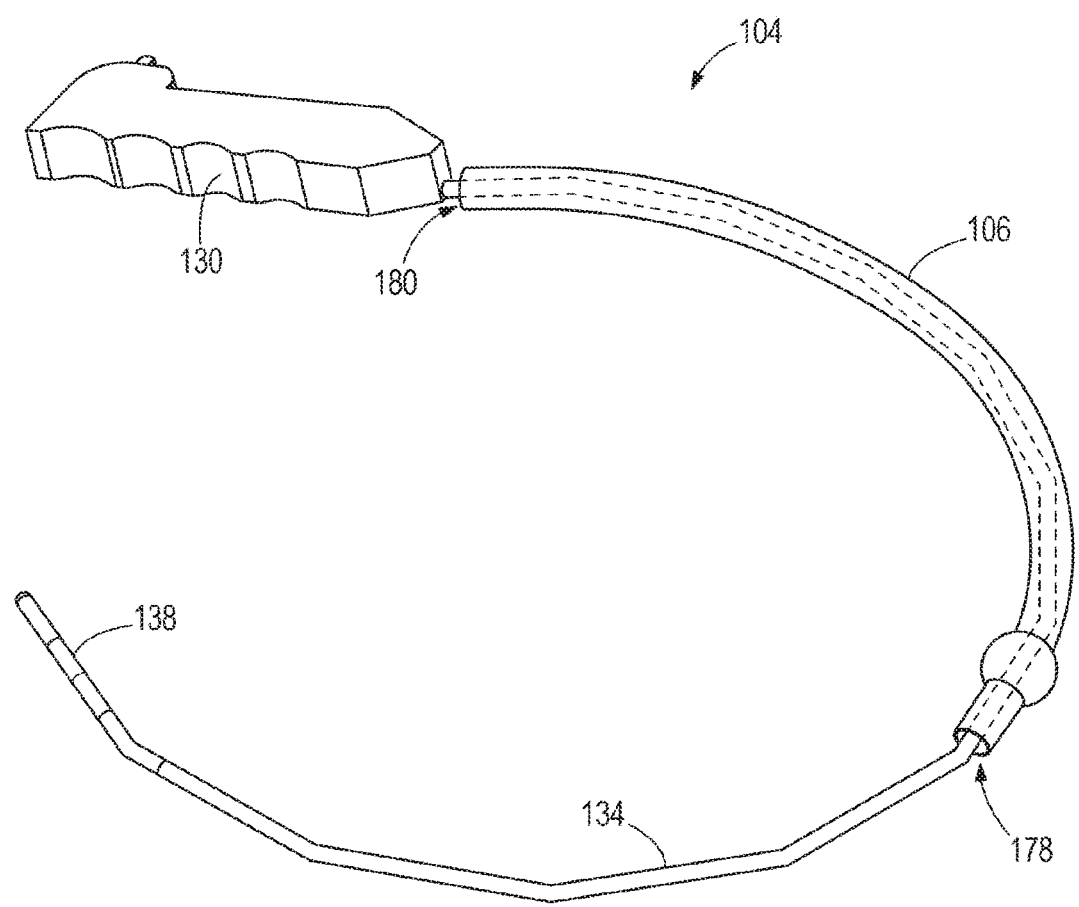
FIG. 9 is a view of an example endotracheal tube mounted on an example articulating stylet.

At operation 705, the endotracheal tube is mounted on the articulating stylet. The endotracheal tube is mounted by placing the second end of the endotracheal tube over the tip of the articulating stylet and sliding the tube up the shaft of the articulating stylet. This operation may be performed by the physician, someone assisting the physician, or someone preparing the equipment in advance. An example of an articulating stylet with an endotracheal tube mounted is shown in FIG. 9. Alternatively, the endotracheal tube may be mounted after the stylet is placed in the trachea.

Figure 10:
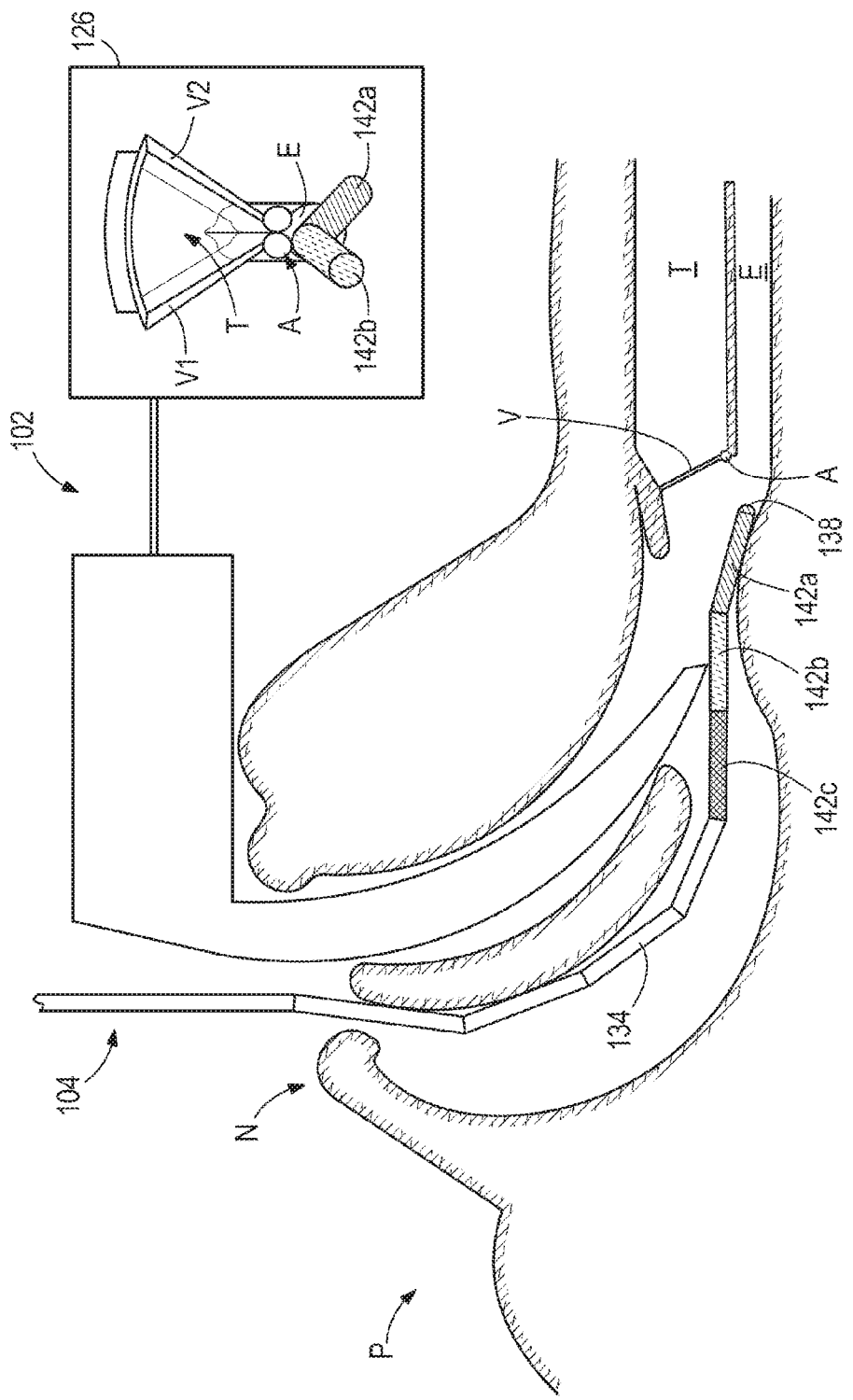
FIG. 10 is a cross-sectional view of a patient after the tip of the articulating stylet is advanced into the field of view of a laryngoscope during an intubation procedure using an example tracheal intubation system including a laryngoscope.

At operation 710, the tip of the articulating stylet is positioned in the pharynx of the patient and is advanced until the tip is visible on the screen of the laryngoscope. In some embodiments, the tip of the articulating stylet is inserted through the nose of the patient. In other embodiments, depending on the anatomy of the patient, the tip of the articulating stylet is inserted through the mouth of the patient. An example embodiment of an articulating stylet that is visible in the field of view of the laryngoscope is shown in FIG. 10.

Figure 11:
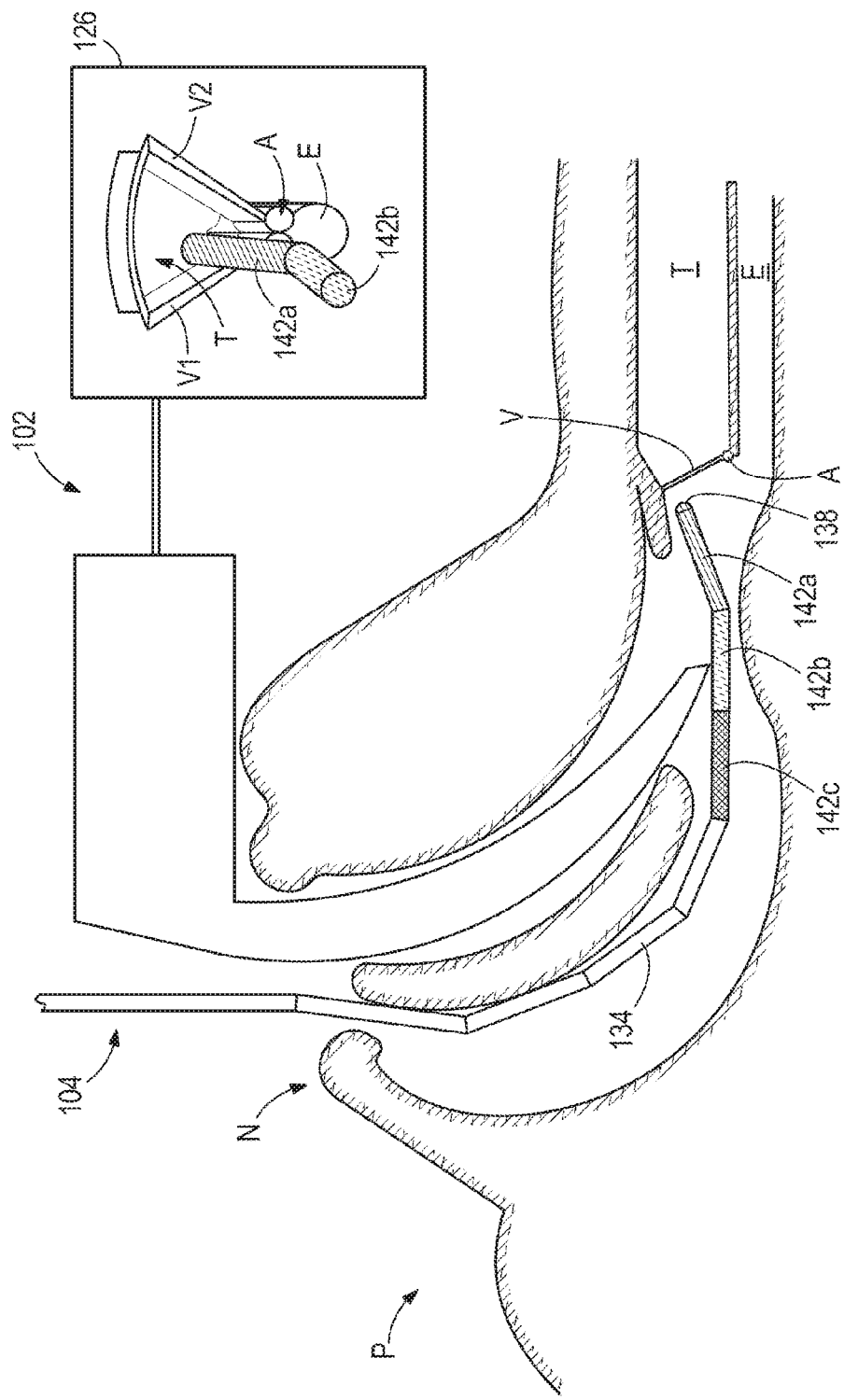
FIG. 11 is a cross-sectional view of a patient after the tip of an articulating stylet is pivoted towards the glottis during an intubation procedure using an example tracheal intubation system including a laryngoscope.

At operation 715, the tip of the articulating stylet is pivoted towards the entrance to the trachea of the patient. That is, the tip is pivoted so that when the articulating stylet is advanced, the tip will pass between the vocal cords of the patient and into the trachea of the patient. In some embodiments, a caregiver, usually a physician or person assisting a physician, pivots the tip of the articulating stylet using a tip control mechanism. The caregiver pivots the tip of the articulating stylet while viewing the tip on the screen of the laryngoscope. In some embodiments, the caregiver will observe an orientation mark on the shaft of the articulating stylet to determine the orientation of the stylet relative to the anatomy of the patient before using the tip control mechanism to pivot the tip. In this manner, a caregiver is able to determine the direction the tip will pivot prior to actually pivoting the tip. An example embodiment of the articulating stylet with the tip pivoted towards the entrance of the trachea of the patient is shown in FIG. 11.

At operation 720, the articulating stylet is advanced into the trachea of the patient. In some embodiments, a caregiver, usually a physician or a person assisting a physician, advances the articulating stylet by holding the handle of the articulating stylet and slowly pushing the shaft of the articulating stylet into the mouth or nose of the patient. In some embodiments, where the patient is an adult, the caregiver will advance the articulating stylet through the trachea of the patient by approximately three centimeters. In other embodiments, the caregiver will advance the stylet through the trachea of the patient by a smaller or larger distance. To accomplish this, the caregiver watches the tip of the articulating stylet with the laryngoscope.

In some embodiments, the articulating stylet includes one or more depth-assessment bands. The caregiver views the shaft of the articulating stylet on the screen of the laryngoscope to determine which depth-assessment band is adjacent to the vocal cords of the patient. Depending on which depth-assessment band is adjacent to the vocal cords, the caregiver may continue to advance the articulating stylet or stop advancing the articulating stylet.

Figure 12:
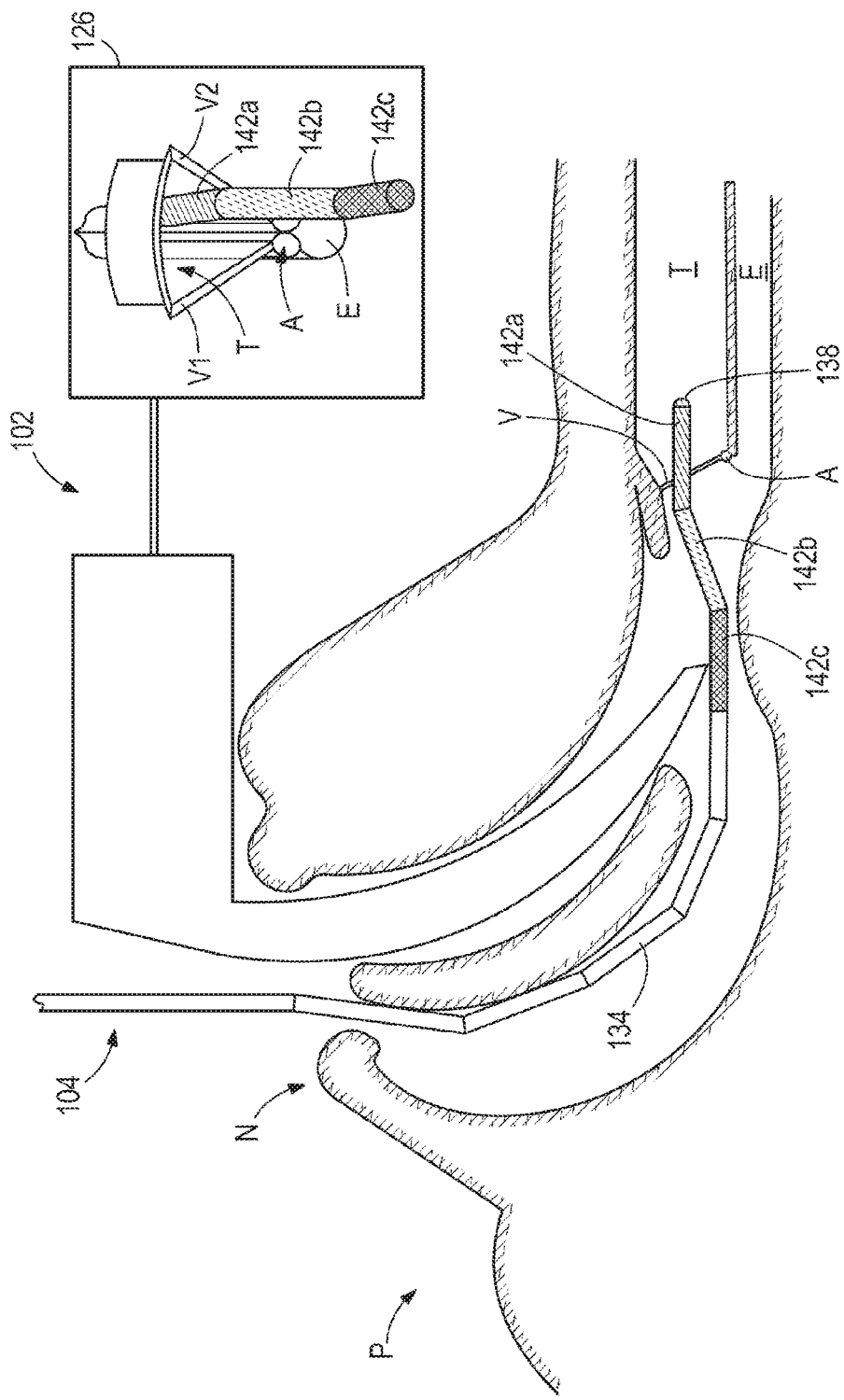
FIG. 12 is a cross-sectional view of a patient after the tip of an articulating stylet is advanced into the trachea to a first depth-assessment band during an intubation procedure using an example tracheal intubation system including a laryngoscope.
Figure 13:
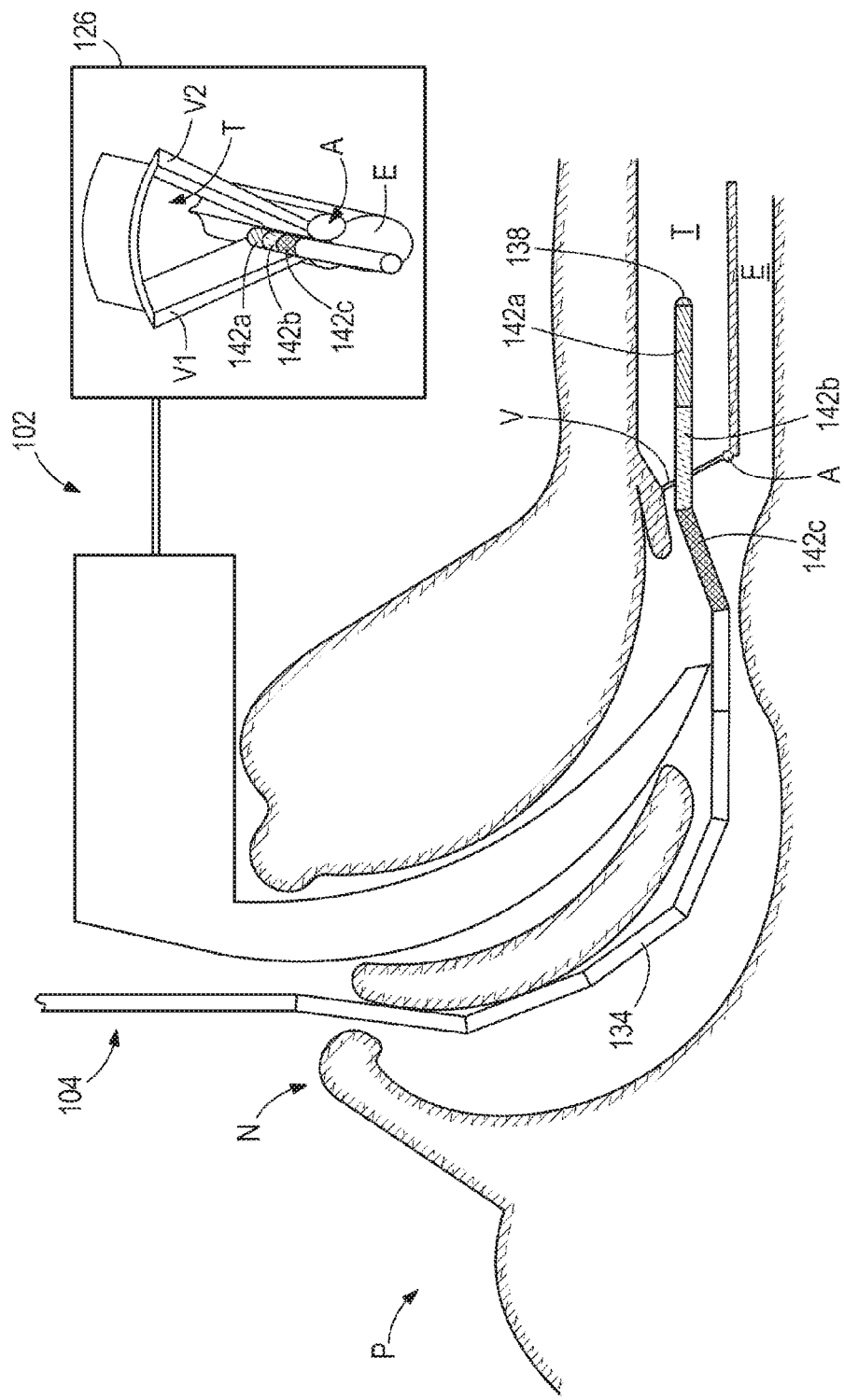
FIG. 13 is a cross-sectional view of a patient after the tip of an articulating stylet is advanced into the trachea to a second depth-assessment band during an intubation procedure using an example tracheal intubation system including a laryngoscope.

For example, in an embodiment in which the articulating stylet includes three depth-assessment bands and the second depth-assessment band represents the target insertion depth, a caregiver will continue to advance the articulating stylet until the second depth-assessment band is adjacent to the vocal cords of the patient. Accordingly, if the screen of the laryngoscope shows that the first depth-assessment band is adjacent to the vocal cords, the caregiver may continue to advance the articulating stylet. Similarly, if the screen of the laryngoscope shows that the second depth-assessment band is adjacent to the vocal cords of the patient, the caregiver may determine that the tip of the articulating stylet is properly positioned and, accordingly, will stop advancing the articulating stylet. Finally, if the screen of the laryngoscope shows that the third depth-assessment band is adjacent to the vocal cords of the patient, the caregiver may determine that the tip of the articulating stylet has been advanced too far and will stop advancing the articulating stylet or, in some cases, will retract the articulating stylet. An example embodiment of the articulating stylet with three depth-assessment bands being advanced into the trachea of the patient is shown in FIGS. 12 and 13.

Figure 14:
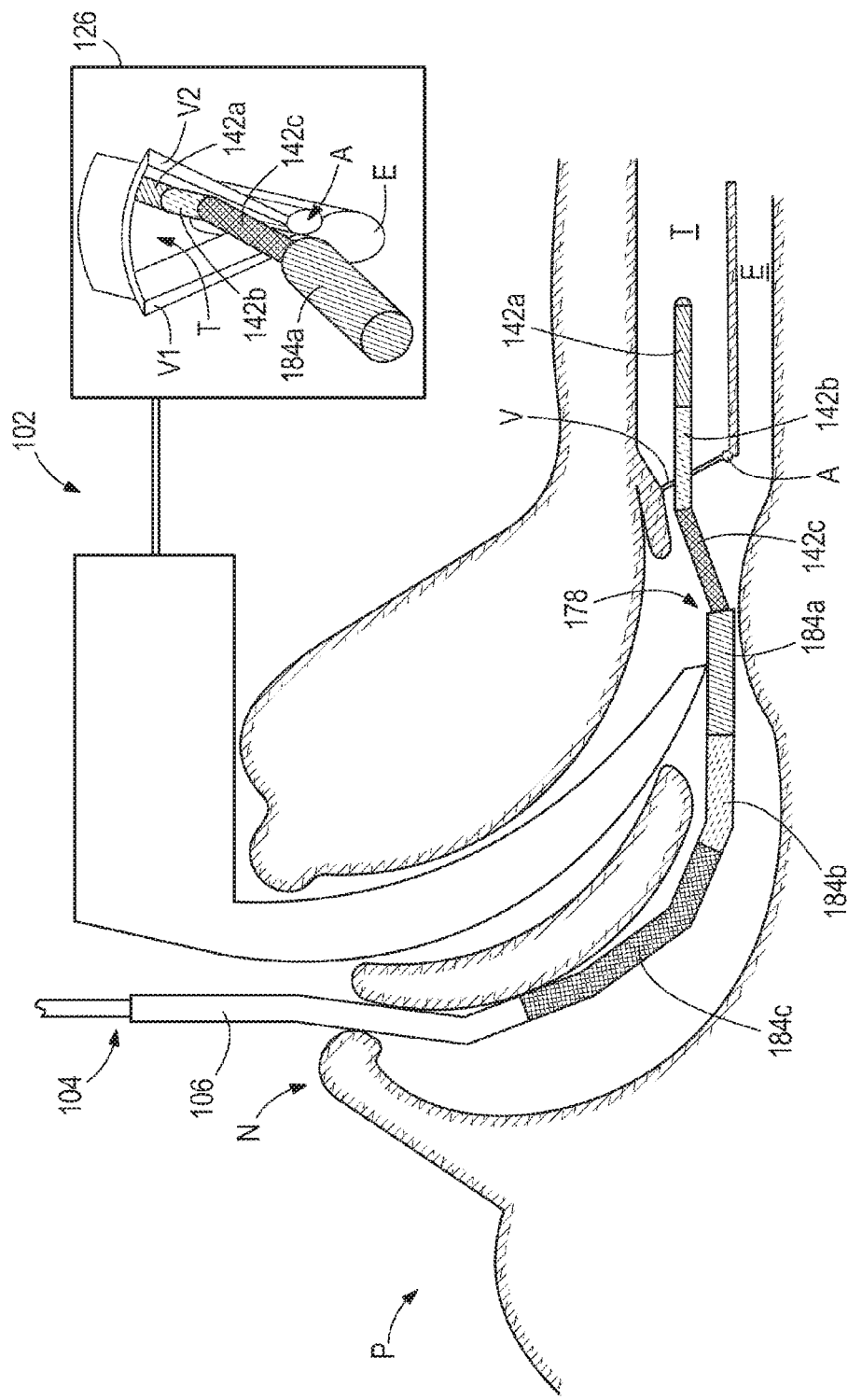
FIG. 14 is a cross-sectional view of a patient after an endotracheal tube is advanced over the articulating stylet into the field of view of the laryngoscope during an intubation procedure using an example tracheal intubation system including a laryngoscope.
Figure 15:
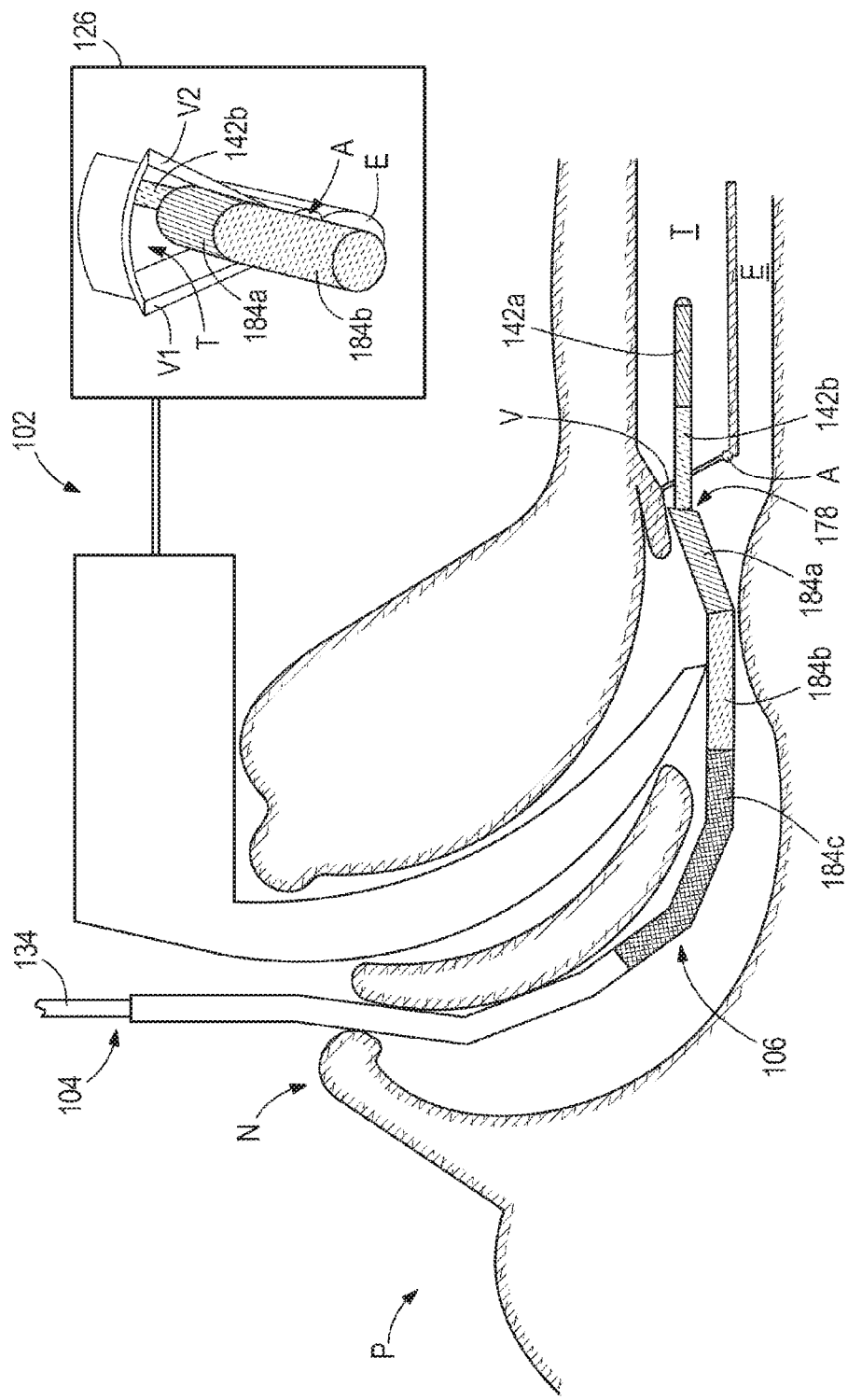
FIG. 15 is a cross-sectional view of a patient after an endotracheal tube is advanced over the articulating stylet towards the glottis during an intubation procedure using an example tracheal intubation system including a laryngoscope.

At operation 725, the endotracheal tube is advanced over the shaft of the articulating stylet. In some embodiments, a caregiver, usually a physician or person assisting a physician grabs the endotracheal tube and slides it along the articulating stylet until the first end of the endotracheal tube enters the trachea of the patient. An example embodiment of the endotracheal tube being advanced over the shaft of the articulating stylet is shown in FIGS. 14 and 15.

Figure 16:
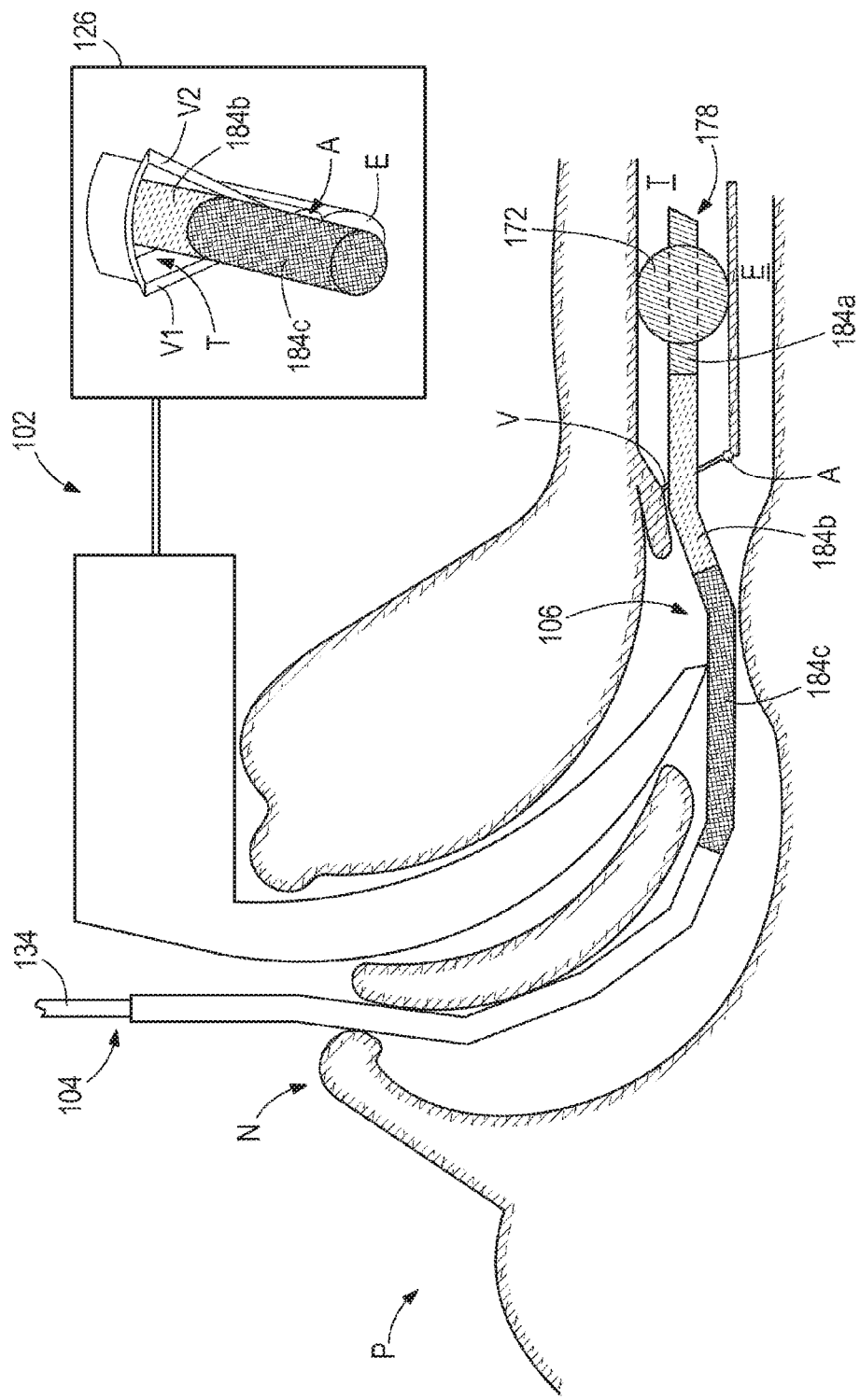
FIG. 16 is a cross-sectional view of a patient after an endotracheal tube is advanced over the articulating stylet into a final position in the trachea during an intubation procedure using an example tracheal intubation system including a laryngoscope.

At operation 730, the cuff of the endotracheal tube is inflated. In some embodiments, a caregiver, usually a physician or person assisting a physician inserts a fluid into the inflation port of the endotracheal tube. This causes the inflation cuff to expand and secures the endotracheal tube in the trachea of the patient. In addition, the inflation cuff seals the trachea of the patient so that gases will not flow around the endotracheal tube. Further, the inflation cuff seals the trachea of the patient so that liquids, such as the contents of the stomach of the patient, will not enter the trachea and the lungs of the patient. An example embodiment of an endotracheal tube with an inflated cuff is shown in FIG. 16. In embodiments where the endotracheal tube does not include a cuff, this operation 730 is not performed.

At operation 735, the articulating stylet and laryngoscope are removed. The shaft of the articulating stylet is pulled out of the endotracheal tube, leaving the endotracheal tube in place. In addition, the laryngoscope is also removed from the patient. The laryngoscope is removed by grabbing the handle and pulling the blade out of the pharynx of the patient.

At operation 740, the endotracheal tube is connected to a ventilator or breathing circuit to provide ventilation for the patient. In some embodiments, the endotracheal tube is connected to the ventilator or breathing circuit before the laryngoscope is removed.

FIG. 8 is a cross-sectional view of a patient P during an intubation procedure using an example tracheal intubation system including a laryngoscope.

The mouth M and nose N of the patient P are shown. The blade 110 of the laryngoscope 102 is disposed in the pharynx of the patient P. The blade 110 is oriented so that the field of view 50 of the optical capture device on blade 110 includes the vocal cords V and trachea T of the patient P. Screen 126 shows the contents of the field of view 50 of the optical capture device in the laryngoscope 102.

The screen 126 displays an image of the trachea T. The entrance to the trachea T is defined by the vocal cords V1 and V2 (collectively vocal cords V). The vocal cords V meet at the arytenoids A. The esophagus E is below the trachea T and parallel to the trachea T. It is important that the blade 110 of the laryngoscope 102 is oriented so that screen 126 shows a clear image of the entrance of the trachea T because the articulating stylet will be directed into the trachea T.

FIG. 9 is a view of an example of an endotracheal tube 106 mounted on an articulating stylet 104. As described in FIG. 6, the endotracheal tube 106 includes a pipe with a first end 178 and a second end 180. The shaft 134 of the articulating stylet 104 passes through the endotracheal tube 106. The endotracheal tube 106 is oriented so that the first end 178 is nearer to the tip 138 of the articulating stylet 104 and the second end 180 is nearer to the handle 130 of the articulating stylet 104.

FIG. 10 is a cross-sectional view of a patient P during an intubation procedure using an example tracheal intubation system including a laryngoscope. The shaft 134 of the articulating stylet 104 is being advanced into the patient P through the nose N of the patient P. The tip 138 is in the field of view of the optical capture device of the laryngoscope 102. The first depth-assessment band 142a and the second depth-assessment band 142b are visible on screen 126. Screen 126 displays that the tip 138 is currently directed towards the esophagus E.

FIG. 11 is a cross-sectional view of a patient P during an intubation procedure using an example tracheal intubation system including a laryngoscope. The tip 138 of the articulating stylet 104 is pivoted up as compared to its position in FIG. 10. The screen 126 shows that the tip 138 is now directed towards the entrance of the trachea T.

FIG. 12 cross-sectional view of a patient P during an intubation procedure using an example tracheal intubation system including a laryngoscope. The tip 138 of the articulating stylet 104 is advanced into the trachea T of the patient P. The screen 126 shows that the first depth-assessment band 142a is adjacent to the vocal cords V. Accordingly, a caregiver may determine that the tip 138 needs to be advanced further into the trachea T.

FIG. 13 is a cross-sectional view of a patient P during an intubation procedure using an example tracheal intubation system including a laryngoscope. The tip 138 of the articulating stylet 104 is advanced further into the trachea T of the patient P as compared to FIG. 12. The screen 126 shows that the second depth-assessment band 142b is now adjacent to the vocal cords V. Accordingly, a caregiver may determine that the tip 138 is properly positioned and does not need to be advanced further into the trachea T.

FIG. 14 is a cross-sectional view of a patient P during an intubation procedure using an example tracheal intubation system including a laryngoscope. The tip 138 of the articulating stylet 104 is properly positioned in the trachea T of the patient P. The endotracheal tube 106 has been advanced over the shaft 134 of the articulating stylet 104. The endotracheal tube 106 is guided by the articulating stylet 104 through the nose N of the patient P and into the pharynx of the patient P. The first end 178 and the first depth-assessment band 184a of endotracheal tube 106 are visible on the screen 126.

FIG. 15 is a cross-sectional view of a patient P during an intubation procedure using an example tracheal intubation system including a laryngoscope. The tip 138 of the articulating stylet 104 is properly positioned in the trachea T of the patient P. The endotracheal tube 106 has been advanced further along shaft 134 of the articulating stylet 104 as compared to FIG. 14. The endotracheal tube 106 is guided into the trachea T of the patient P by the articulating stylet 104. The screen 126 displays that the first end 178 of endotracheal tube 106 has not yet reached the vocal cords V. Both the first depth-assessment band 184a and the second depth-assessment band 184b are visible on screen 125. However, neither the first depth-assessment band 184a nor the second depth-assessment band 184b are adjacent to the vocal cords V yet. Accordingly, the caregiver may determine that the first end 178 of the endotracheal tube 106 needs to be advanced further to enter the trachea T of the patient P.

FIG. 16 is cross-sectional view of a patient P during an intubation procedure using an example tracheal intubation system including a laryngoscope. The endotracheal tube 106 has been advanced further along shaft 134 of the articulating stylet 104 as compared to FIG. 15. The screen 126 displays that the endotracheal tube 106 has entered the trachea T. Additionally, screen 126 displays that the second depth-assessment band 184b is adjacent to the vocal cords V. Accordingly, a caretaker may determine that the endotracheal tube 106 has been guided into the trachea T of the patient P and has been properly positioned therein. If instead the first depth-assessment band 184a were adjacent to the vocal cords V, a caregiver may determine that the endotracheal tube 106 needs to be advanced further into the trachea T of the patient P. Conversely, if instead the third depth-assessment band 184c were adjacent to the vocal cords V, the caregiver might determine that the endotracheal tube 106 was advanced too far into the trachea T of the patient P. Once the endotracheal tube 106 is properly positioned, the cuff 172 is inflated to seal the trachea T and secure the endotracheal tube 106 in position.

FIG. 17 is a schematic view of an embodiment of the endotracheal tube 106 disposed in a trachea T. The diagram illustrates the vocal cords V that form the entrance to the trachea T and the left bronchus B1 and the right bronchus B2 that split off from the bottom of the trachea T. The example endotracheal tube 106 includes a first end 178, a first depth-assessment band 184a, a second depth-assessment band 184b, and a third depth-assessment band 184c. In the figure, the second depth-assessment band 184b is adjacent to the vocal cords V and the first end 178 is disposed in the middle of the trachea T. Here, a caretaker may determine that the endotracheal tube 106 is properly positioned in the trachea T. Accordingly, by viewing the vocal cords V and the second depth-assessment band 184b with a laryngoscope, a caretaker is able to determine whether the endotracheal tube 106 is properly positioned.

FIG. 18 is another schematic view of an embodiment of the endotracheal tube 106 disposed in a trachea T. Here, the endotracheal tube 106 has been advance further into the trachea T relative to its position in FIG. 17. In the figure, the third depth-assessment band 184c is adjacent to the vocal cords V and the first end 178 has begun to enter the left bronchus B1. Here, the endotracheal tube 106 may cause trauma to the left bronchus B1. Accordingly, by viewing the vocal cords V and the third depth-assessment band 184c with a laryngoscope, a caretaker is able to determine whether the endotracheal tube 106 is positioned too deeply in the trachea T.

Figure 19:
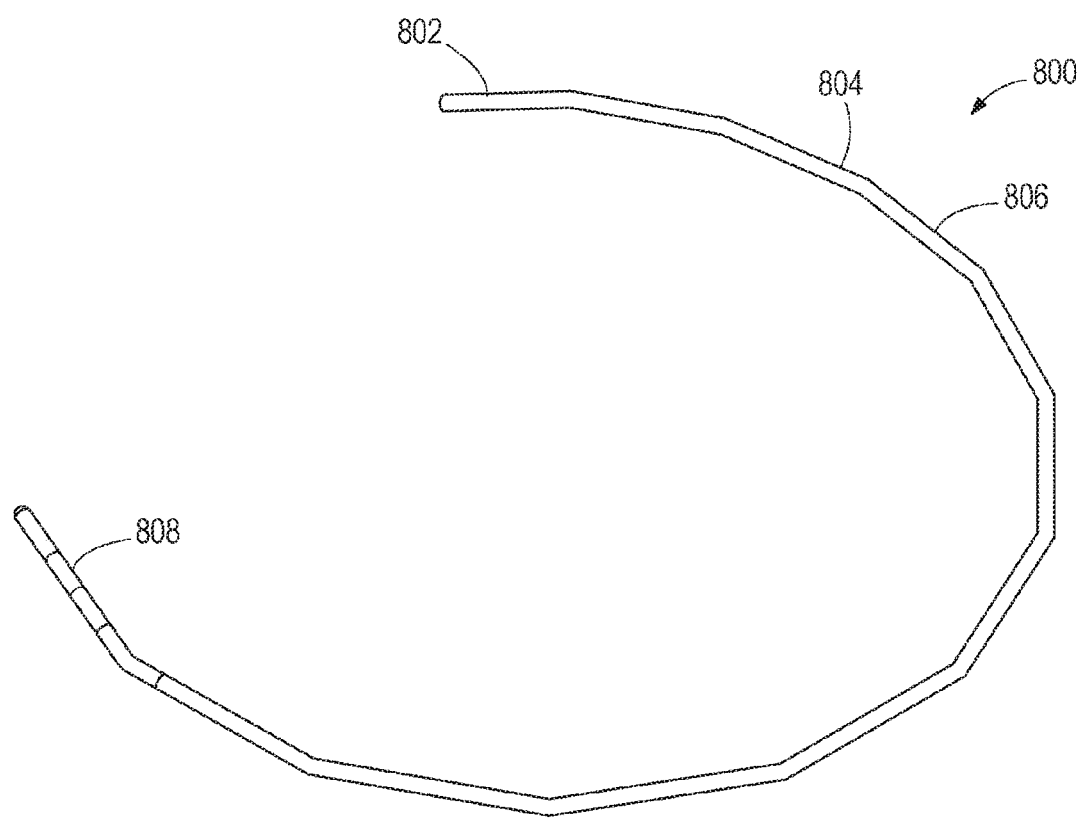
FIG. 19 is a perspective view of an example alternative embodiment of an articulating stylet.

FIG. 19 is a perspective view of an example alternative embodiment of an articulating stylet 800. The articulating stylet 800 is configured to guide an endotracheal tube into the trachea of a patient. In some embodiments, the articulating stylet 800 is configured to be used during an endotracheal tube exchange procedure in which an existing endotracheal tube is replaced with a new endotracheal tube. In some embodiments, the articulating stylet 800 includes a shaft 804 and tip control lever 802. However, in other embodiments, the articulating stylet 800 does not include the tip control lever 802.

The shaft 804 includes an exterior surface 806 and a tip 808. In some embodiments, the shaft 804, the exterior surface 806, and the tip 808 are similar to the shaft 134, the exterior surface 136, and the tip 138 respectively, which are all shown and described in greater detail with respect to FIG. 3. In some embodiments, the tip 808 is configured to articulate. In other embodiments, the tip 808 does not articulate.

The tip control lever 802 is an elongate member and is configured to control the directional movement of the tip 808. In some embodiments, the tip control lever 802 is configured to be actuated in one or more directions by a caregiver. Upon actuation in a first direction, the tip control lever 802 causes the tip 808 to articulate in a corresponding direction. In some embodiments, the tip control lever 802 causes the tip 808 to move in a direction that is substantially similar to the direction in which the tip control lever 802 is actuated. In other embodiments, the tip control lever 802 causes the tip 808 to move in a direction that is substantially opposite to the direction in which the tip control lever 802 is actuated. In some embodiments, the tip control lever 802 is rigid and actuates substantially in a rotational manner around a single end point. In other embodiments, the tip control lever 802 is flexible and is configured to be bent in one or more directions.

Additionally, in some embodiments, the tip control lever 802 is narrow enough that the endotracheal tube 106 may be advanced over it. If an existing endotracheal tube 106 is already positioned in the trachea T of the patient P, the articulating stylet 800 may be advanced into the trachea T of the patient P through that endotracheal tube 106. Then the endotracheal tube 106 may be removed by advancing the endotracheal tube 106 along the articulating stylet 800, over the tip control lever 802, and off of the articulating stylet 800. Further, after the articulating stylet 800 is positioned in the trachea T of the patient P, a new endotracheal tube 106 may be placed over the end of the tip control lever 802 and advanced along the articulating stylet 800. In this manner, the articulating stylet 800 can be used to perform an endotracheal tube exchange procedure in which an existing first endotracheal tube is removed and a new second endotracheal tube is inserted.

Figure 20:
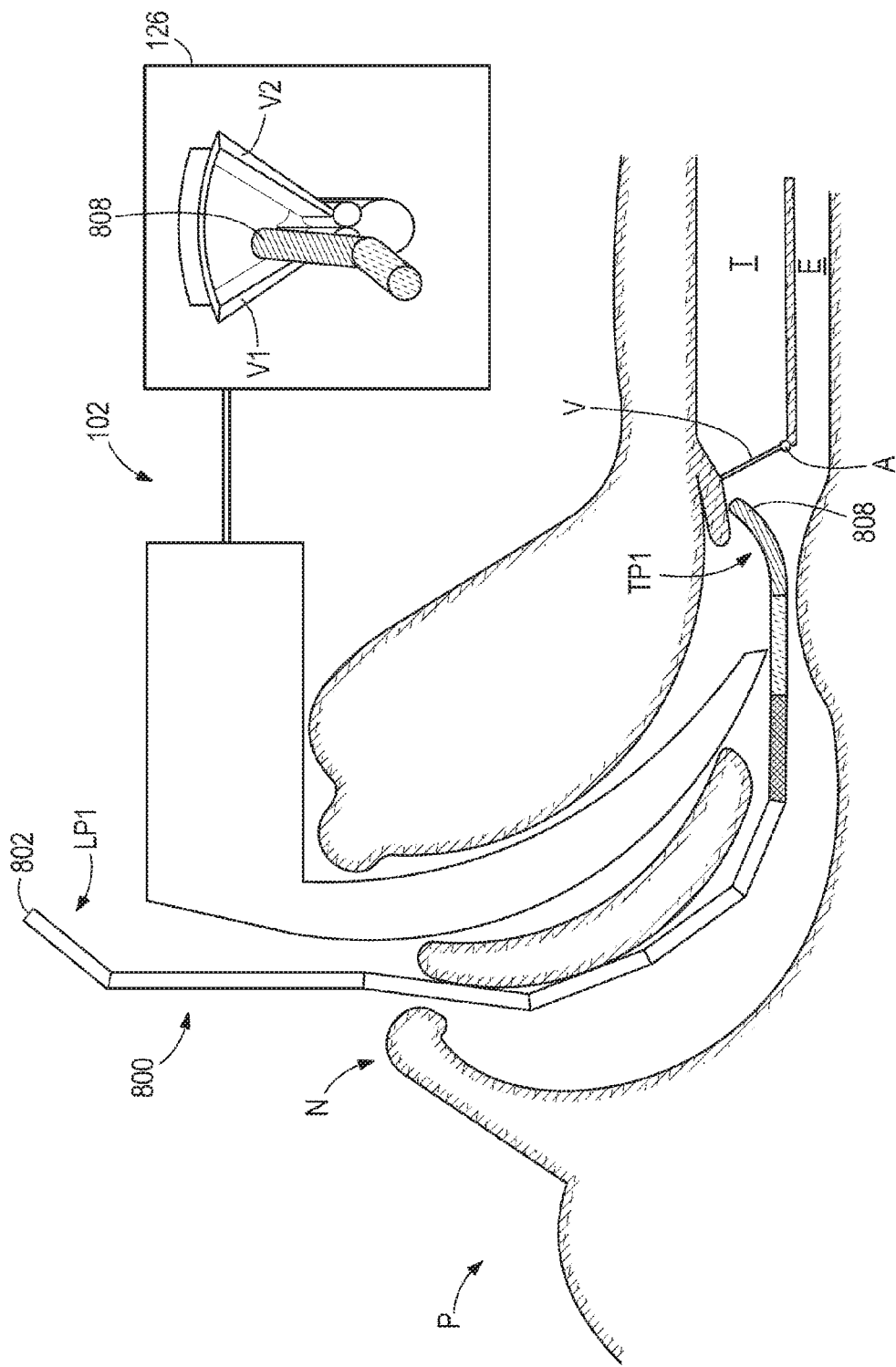
FIG. 20 is a cross-sectional view of a patient during an intubation procedure using an embodiment of the articulating stylet of FIG. 19 in an example tracheal intubation system including a laryngoscope.

FIG. 20 is a cross-sectional view of a patient P during an intubation procedure using an example tracheal intubation system including a laryngoscope. The example tracheal intubation system including a laryngoscope also includes the articulating stylet 800. In the example shown, the tip control lever 802 is rigid and is rotated into a position LP1. Correspondingly, the tip 808 is articulated into a position TP1.

Figure 21:
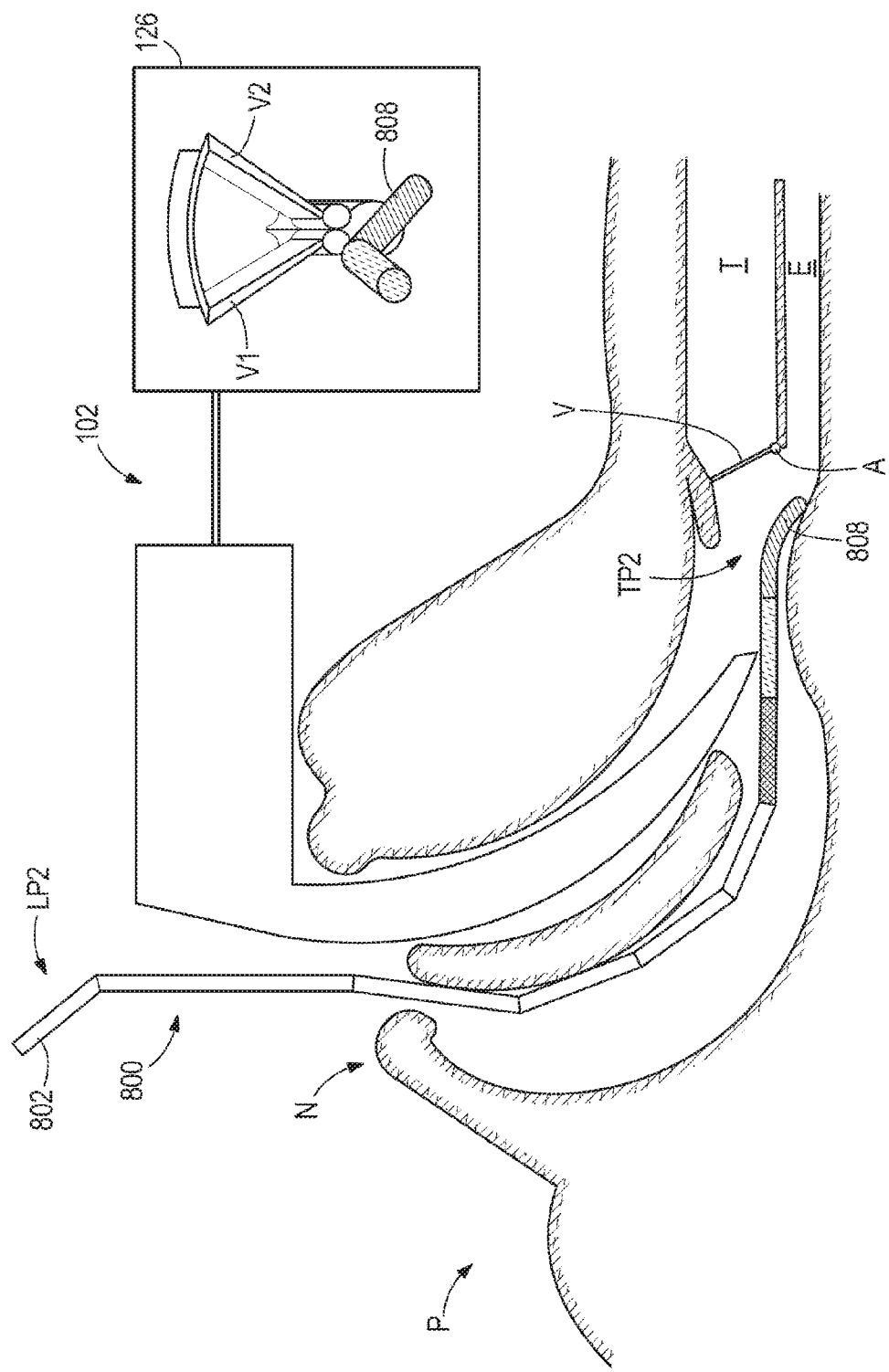
FIG. 21 is another cross-sectional view of a patient during an intubation procedure using an embodiment of the articulating stylet of FIG. 19 in an example tracheal intubation system including a laryngoscope.

FIG. 21 is another cross-sectional view of a patient P during an intubation procedure using an example tracheal intubation system including a laryngoscope. The example tracheal intubation system including a laryngoscope also includes the articulating stylet 800. In this example, the tip control lever 802 is rigid and is rotated into a position LP2. Correspondingly, the tip 808 is articulated into a position TP2.

Figure 22:
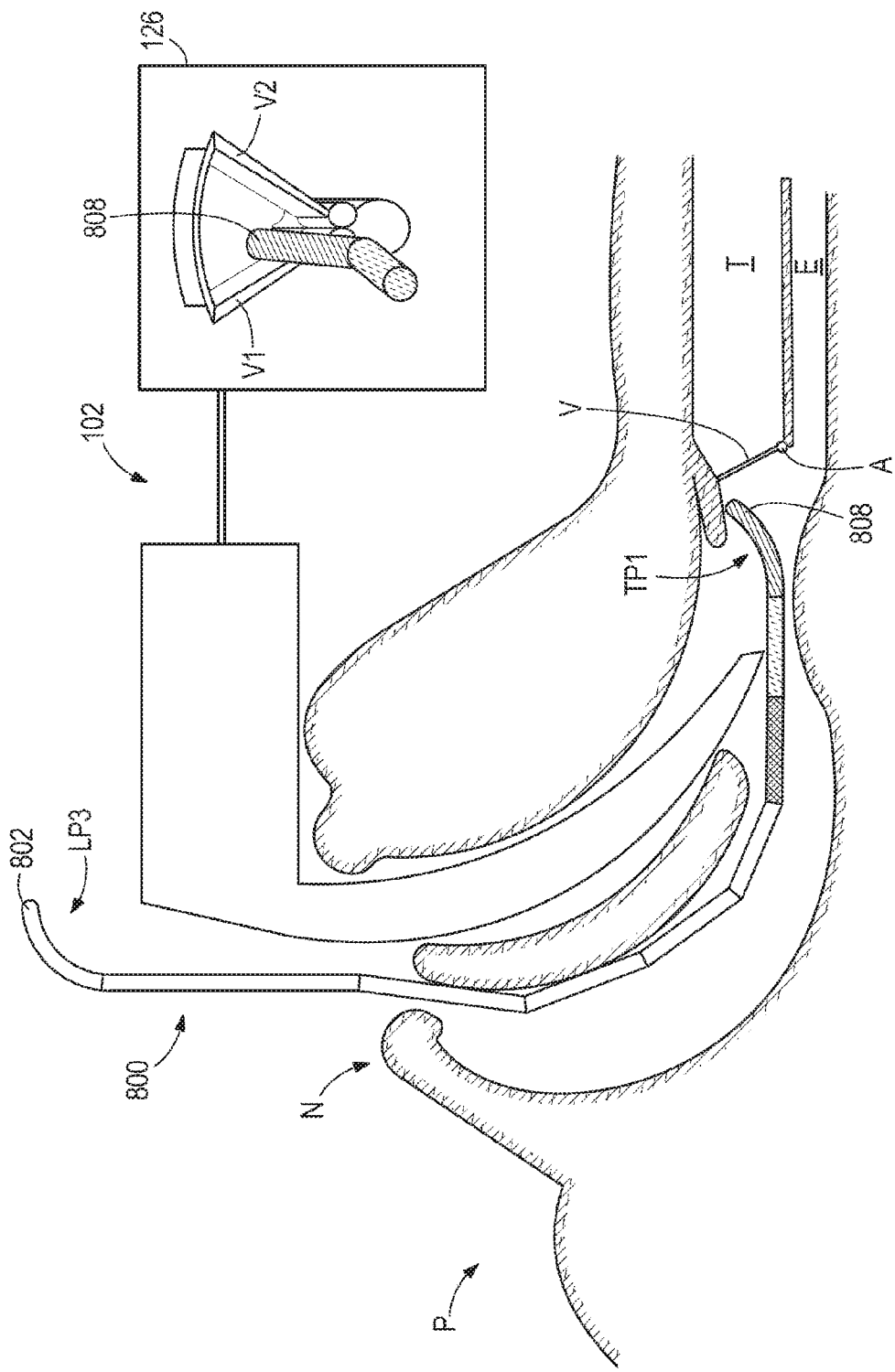
FIG. 22 is a cross-sectional view of a patient during an intubation procedure using another embodiment of the articulating stylet of FIG. 19 in an example tracheal intubation system including a laryngoscope.

FIG. 22 is a cross-sectional view of a patient P during an intubation procedure using an example tracheal intubation system including a laryngoscope. The example tracheal intubation system including a laryngoscope also includes the articulating stylet 800. In the example shown, the tip control lever 802 is flexible and is bent into a position LP3. Correspondingly, the tip 808 is articulated into a position TP1.

Figure 23:
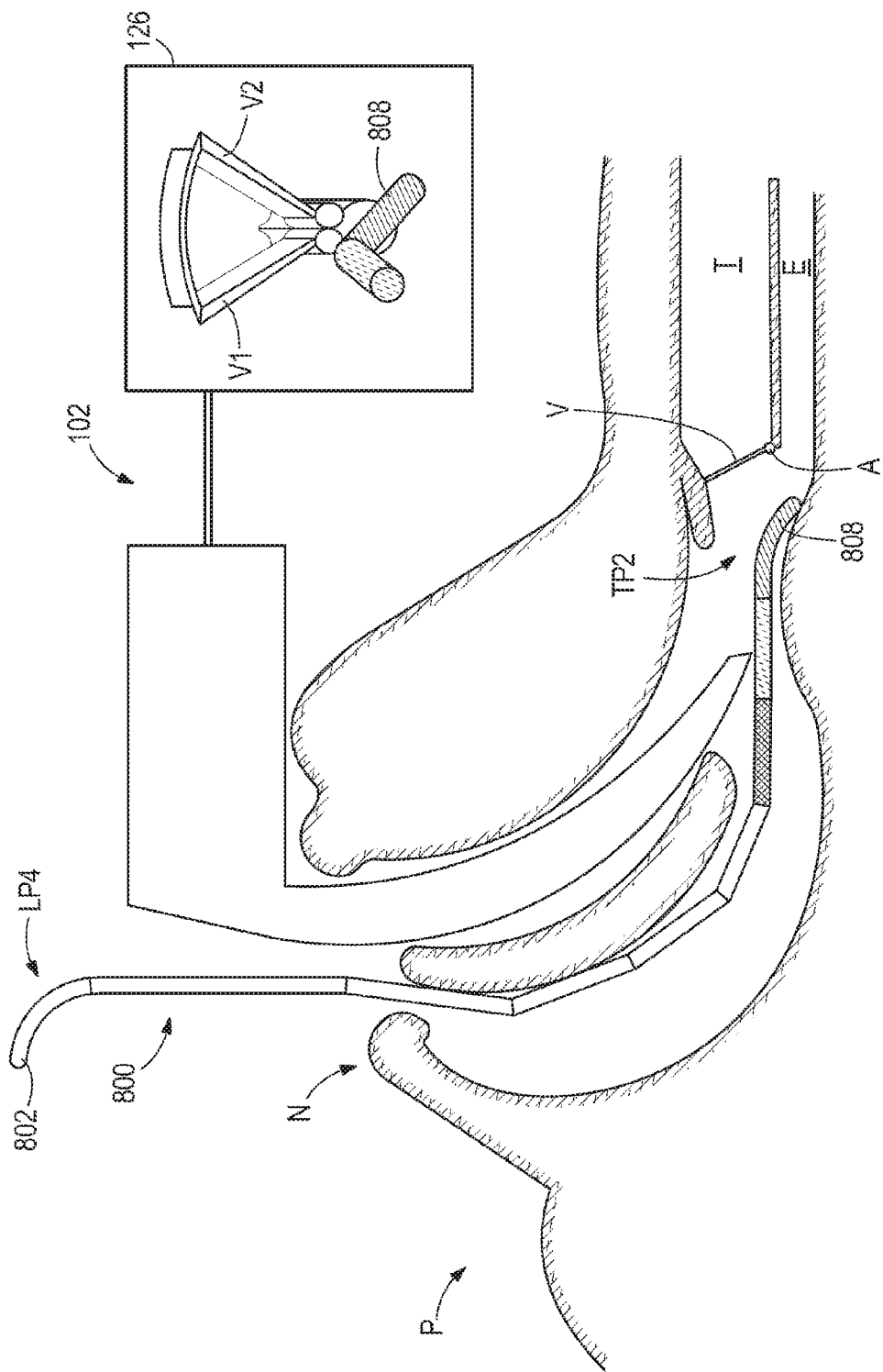
FIG. 23 is another cross-sectional view of a patient during an intubation procedure using another embodiment of the articulating stylet of FIG. 19 in an example tracheal intubation system including a laryngoscope.

FIG. 23 is a cross-sectional view of a patient P during an intubation procedure using an example tracheal intubation system including a laryngoscope. The example tracheal intubation system including a laryngoscope also includes the articulating stylet 800. In the example shown, the tip control lever 802 is flexible and is bent into a position LP4. Correspondingly, the tip 808 is articulated into a position TP2.

Figure 24:
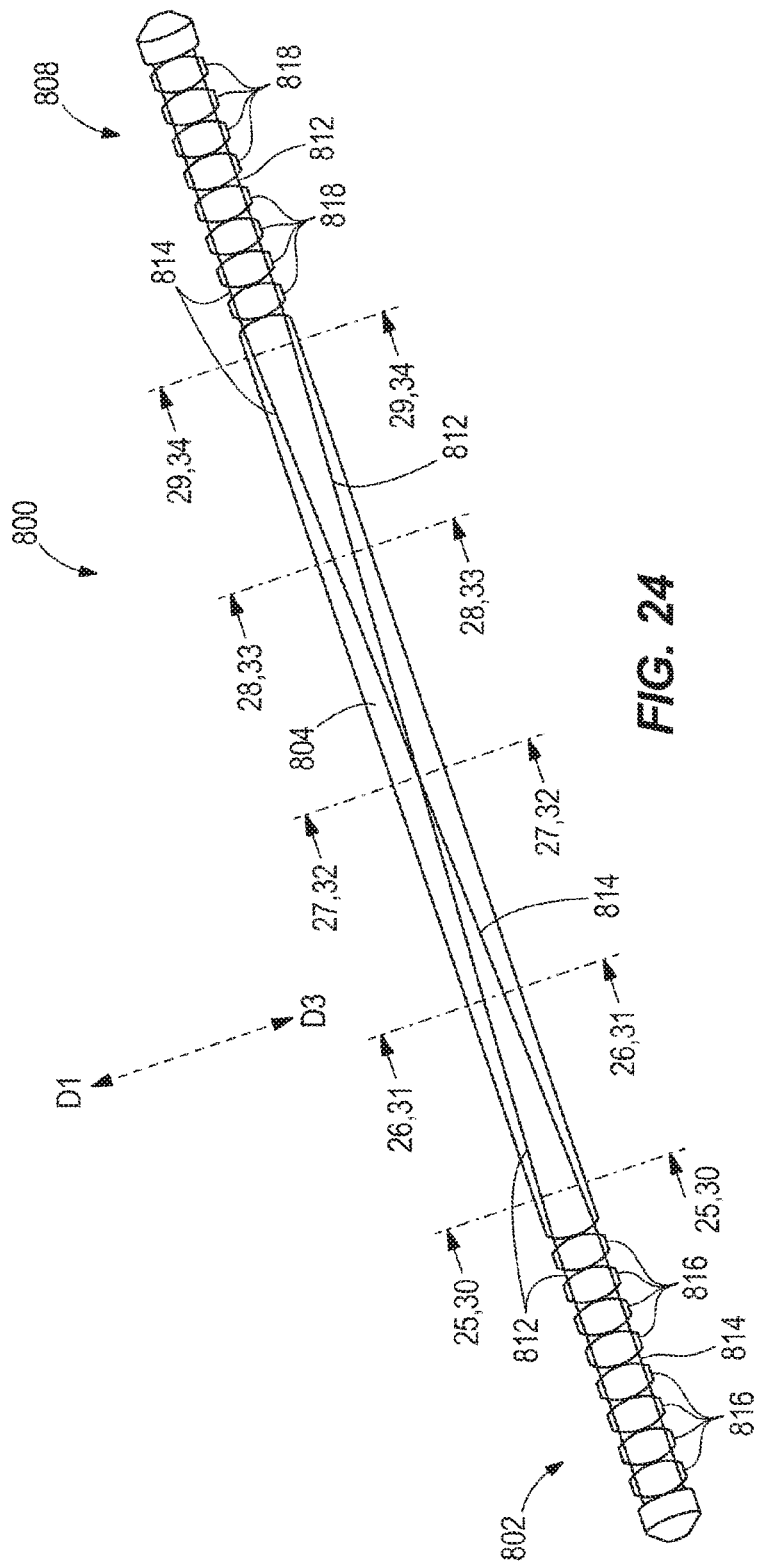
FIG. 24 is a cross-sectional view of an embodiment of the articulating stylet of FIG. 19.

FIG. 24 is a cross-sectional view of an embodiment of the articulating stylet 800. In FIG. 24, the articulating stylet 800 is in a straight position. The articulating stylet 800 includes the tip control lever 802, the shaft 804, the tip 808, a first cable 812, and a second cable 814.

The tip control lever 802 includes a plurality of articulating discs 816. Although in the embodiment shown, the tip control lever 802 includes eight articulating discs 816, in other embodiments, the tip control lever 802 includes more or fewer articulating discs 816. Similarly, the tip 808 also includes a plurality of articulating discs 818. Although in the embodiment shown, the tip 808 includes eight articulating discs 816, in other embodiments, the tip 808 includes more or fewer articulating discs 818.

Figure 35:
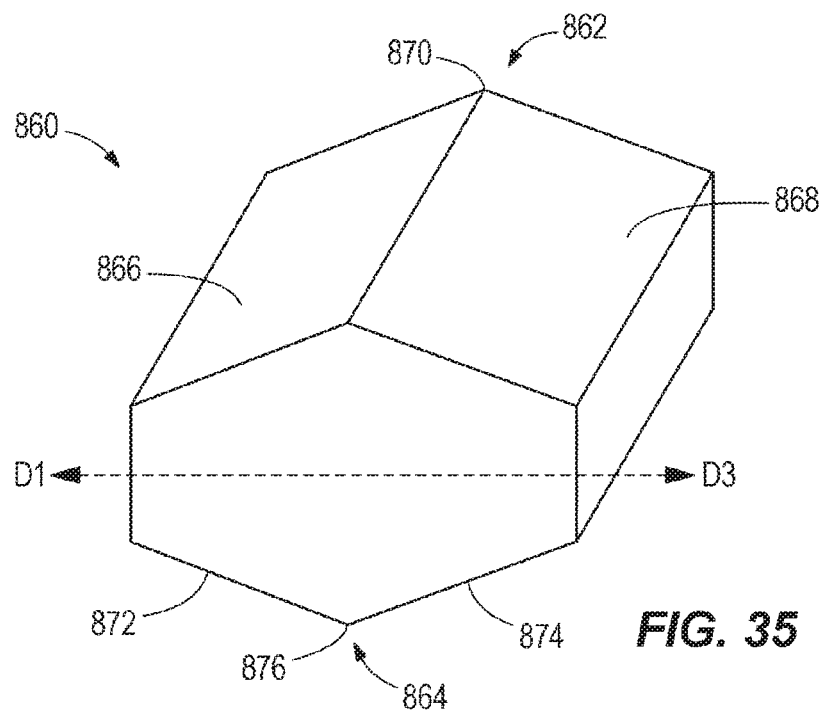
FIG. 35 is a perspective view of an embodiment of a pyramidal-shaped articulating disc of the articulating stylet of FIG. 19.
Figure 36:
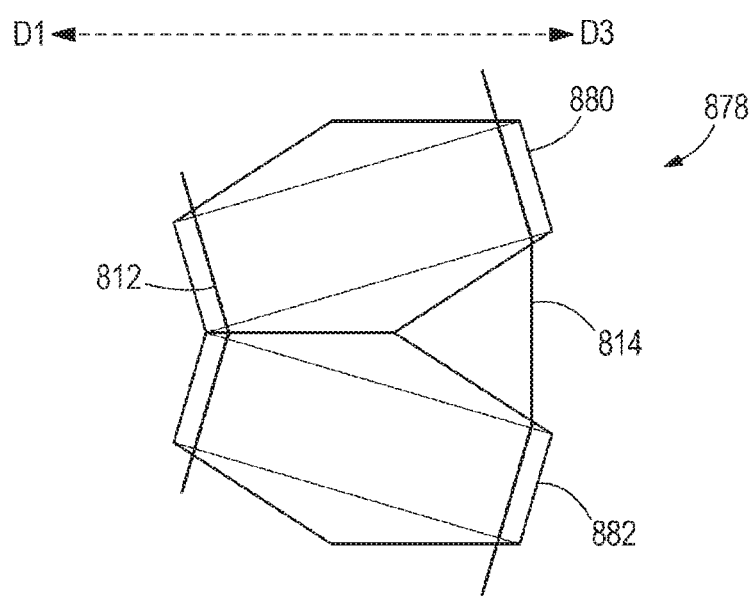
FIG. 36 is a side view of a structure of an embodiment of the articulating stylet of FIG. 19.
Figure 37:
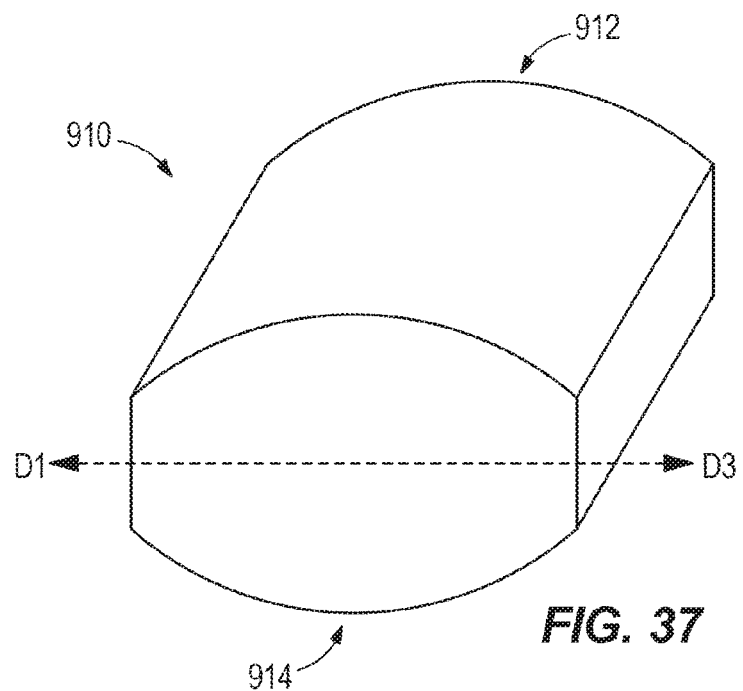
FIG. 37 is a perspective view of an embodiment of a round-shaped articulating disc of the articulating stylet of FIG. 19.
Figure 38:
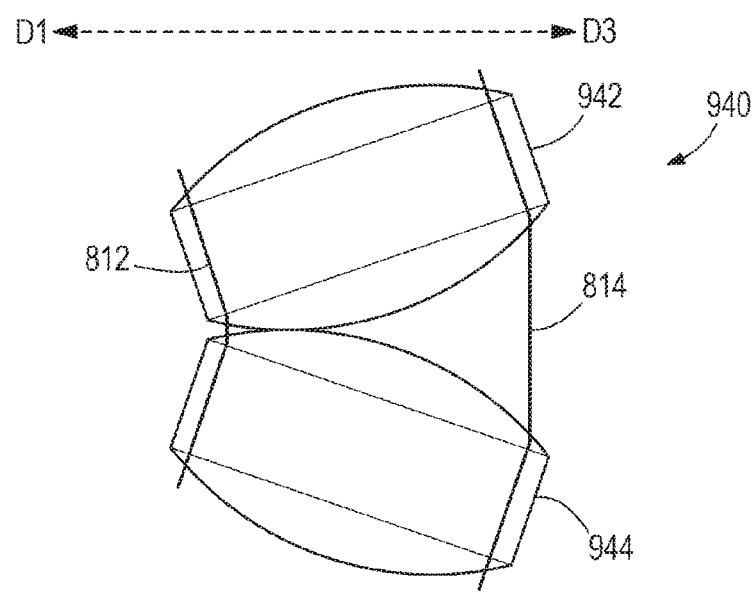
FIG. 38 is a side view of a structure of an embodiment of the articulating stylet of FIG. 19.

The articulating discs in the plurality of articulating discs 816 rotate or articulate against one another and allow the tip control lever 802 to bend or flex. Similarly, the articulating discs in the plurality of articulating discs 818 also rotate or articulate against one another and allow the tip 808 to bend or flex. Example embodiments of the articulating discs of the pluralities of articulating discs 816 and 818 are illustrated and described in greater detail with respect to FIGS. 35-38. In some embodiments, at least a portion of the articulating discs in the pluralities of articulating discs 816 and 818 are pyramidal shaped as are shown in FIGS. 35-36. In some embodiments, at least a portion of the articulating discs in the pluralities of articulating discs 816 and 818 are round shaped as are shown in FIGS. 37-38. In other embodiments, at least a portion of the articulating discs in the pluralities of articulating discs 816 and 818 are other shapes. Further, in some embodiments, the articulating discs in the plurality of articulating discs 816 have a different shape than the articulating discs in the plurality of articulating discs 818. Yet other embodiments are possible as well.

The first cable 812 and the second cable 814 are cables or wires and are configured to control the movement of the tip 808. The first cable 812 is secured to the tip control lever 802 and the tip 808. Similarly, the second cable 814 is also secured to the tip control lever 802 and the tip 808. The first cable 812 and the second cable 814 connected to the tip control lever 802 and the tip 808 at the same distance longitudinally along the tip control lever 802 and the tip 808 but on or near opposite sides radially of the tip control lever 802 and the tip 808. Both the first cable 812 and the second cable 814 are threaded through the shaft 804 and at least a portion of the articulating discs in the pluralities of articulating discs 816 and 818. In some embodiments, the first cable 812 and the second cable 814 cross in the shaft 804. In other embodiments, the first cable 812 and the second cable 814 do not cross in the shaft 804. Various embodiments of the shaft 804 and configurations of the cables are shown in FIGS. 25-34.

Figure 25:
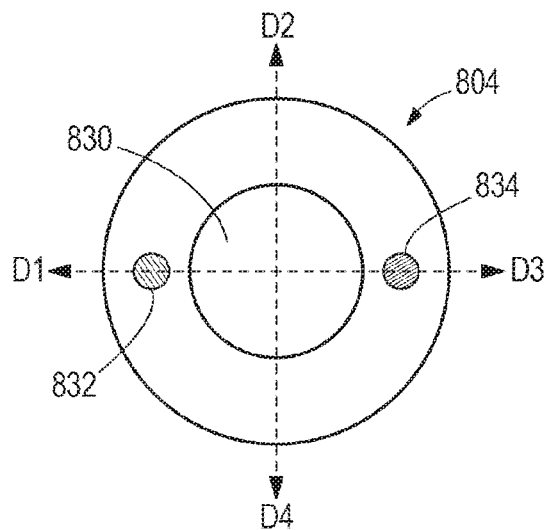
FIG. 25 is a cross-sectional view of an embodiment of the shaft of the articulating stylet of FIG. 19 at the location indicated in FIG. 24.

FIG. 25 is a cross-sectional view of an embodiment of the shaft 804 at the location indicated on FIG. 24. In the embodiment shown, the shaft 804 includes a lumen 830, a first cable route 832, and a second cable route 834.

The lumen 830 is pathway formed in the middle of the shaft 804. In some embodiments, the lumen 830 is used as a passageway between the tip control lever 802 and the tip 808 for oxygen or other gasses. However, some embodiments do not include a lumen 830. In those embodiments, the shaft 804 is solid.

In some embodiments, the first cable route 832 and the second cable route 834 are holes in the shaft 804 through which the first cable 812 and the second cable 814, respectively, are routed. In some embodiments of the shaft 804 that include a lumen 830, the first cable route 832 and the second cable route 834 are holes disposed in a wall structure of the shaft 804. Other embodiments of the first cable route 832 and the second cable route 834 are possible as well.

In FIG. 25, the first cable route 832 is disposed in the shaft 804 in the direction of D1 and the second cable route 834 is disposed in the shaft 804 in the direction of D3.

Figure 26:
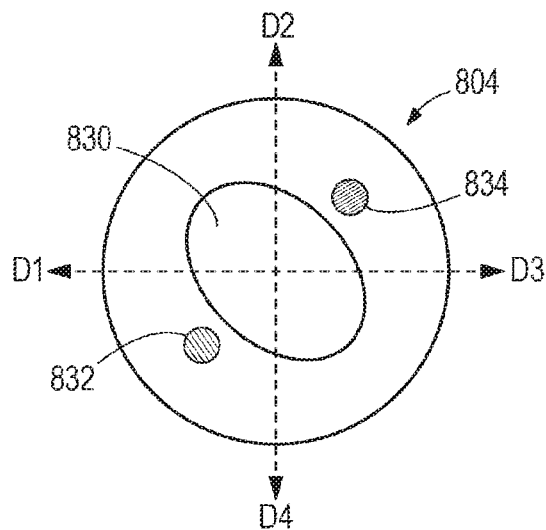
FIG. 26 is another cross-sectional view of the embodiment of the shaft of FIG. 25 at the location indicated in FIG. 24.

FIG. 26 is a cross-sectional view of an embodiment of the shaft 804 at the location indicated on FIG. 24. In FIG. 26, the first cable route 832 is disposed in the shaft 804 between directions D1 and D4 and the second cable route 834 is disposed in the shaft 804 between directions D3 and D2.

Figure 27:
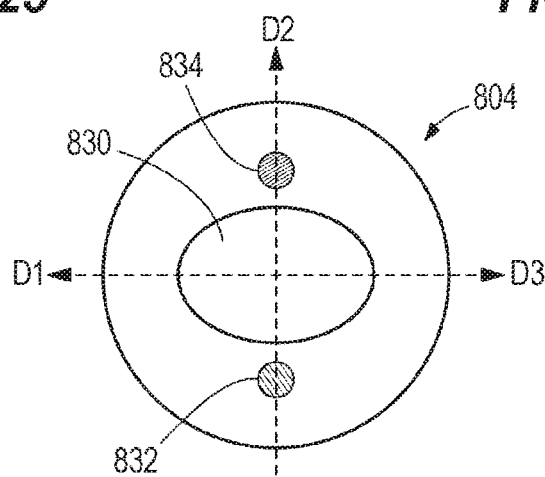
FIG. 27 is another cross-sectional view of an embodiment of the shaft of FIG. 25 at the location indicated in FIG. 24.

FIG. 27 is a cross-sectional view of an embodiment of the shaft 804 at the location indicated on FIG. 24. In FIG. 27, the first cable route 832 is disposed in the shaft 804 in the direction of D4 and the second cable route 834 is disposed in the shaft 804 in the direction of D2.

Figure 28:
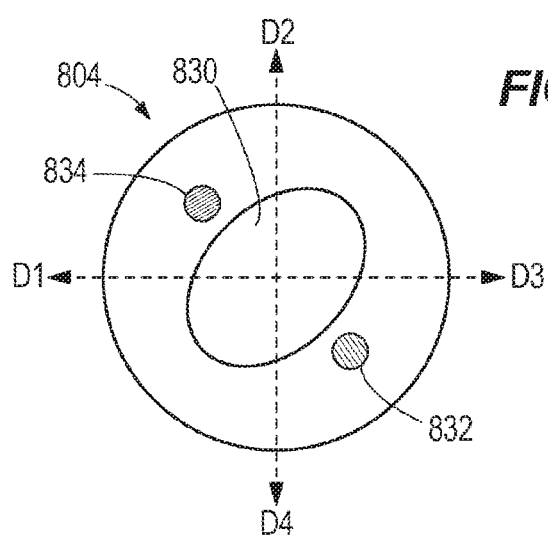
FIG. 28 is another cross-sectional view of an embodiment of the shaft of FIG. 25 at the location indicated in FIG. 24.

FIG. 28 is a cross-sectional view of an embodiment of the shaft 804 at the location indicated on FIG. 24. In FIG. 28, the first cable route 832 is disposed in the shaft 804 between directions D4 and D3 and the second cable route 834 is disposed in the shaft 804 between directions D2 and D1.

Figure 29:
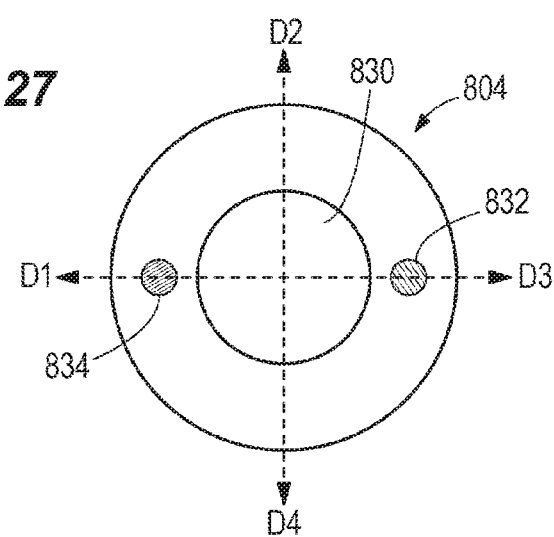
FIG. 29 is another cross-sectional view of an embodiment of the shaft of FIG. 25 at the location indicated in FIG. 24.

FIG. 29 is a cross-sectional view of an embodiment of the shaft 804 at the location indicated on FIG. 24. In FIG. 29, the first cable route 832 is disposed in the shaft 804 in the direction of D3 and the second cable route 834 is disposed in the shaft 804 in the direction of D1. As is illustrated by the sequence of cross-sectional views in FIGS. 25-29, the first cable route 832 and the second cable route 834 each switch to the opposite side of the shaft 804 by rotating through the wall of the shaft 804. In this manner, the first cable 812 connects a first radial side of the tip control lever 802 to the opposite radial side of the tip 808. Similarly, the second cable 814 connected the D3 side of the tip control lever 802 to the D1 side of the tip 808.

Figure 30:
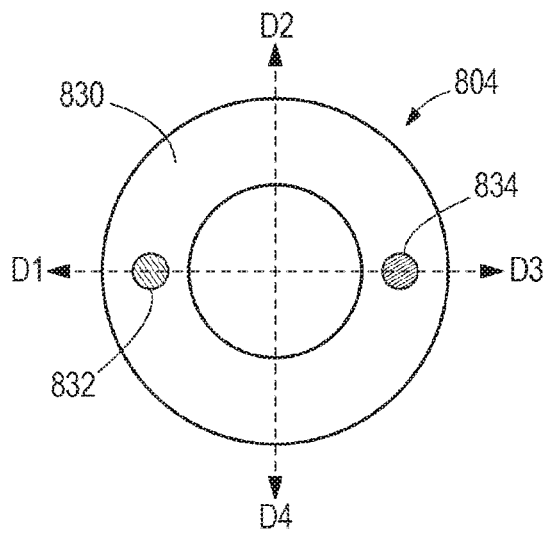
FIG. 30 is a cross-sectional view of another embodiment of the shaft of the articulating stylet of FIG. 19 at the location indicated in FIG. 24.

FIG. 30 is a cross-sectional view of another embodiment of the shaft 804 at the location indicated on FIG. 24. In the embodiment shown, the shaft 804 includes the lumen 830, the first cable route 832, and the second cable route 834. In FIG. 25, the first cable route 832 is disposed in the shaft 804 in the direction of D1 and the second cable route 834 is disposed in the shaft 804 in the direction of D3.

Figure 31:
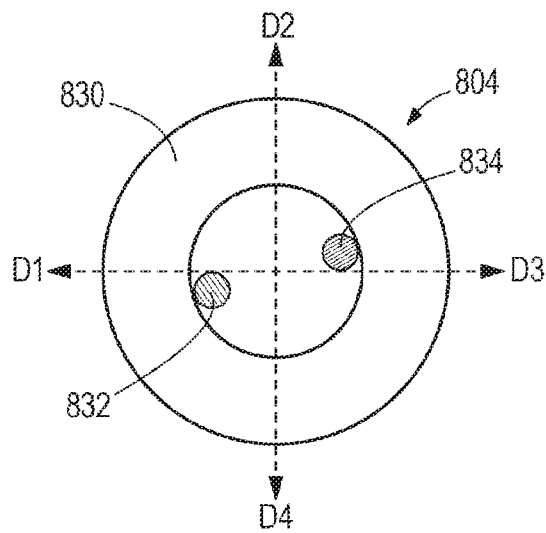
FIG. 31 is another cross-sectional view of an embodiment of the shaft of the articulating stylet of FIG. 30 at the location indicated in FIG. 24.

FIG. 31 is a cross-sectional view of an embodiment of the shaft 804 at the location indicated on FIG. 24. In FIG. 31, the first cable route 832 is disposed in the lumen 830 towards the direction D1 and the second cable route 834 is disposed in the lumen 830 towards the direction D3.

Figure 32:
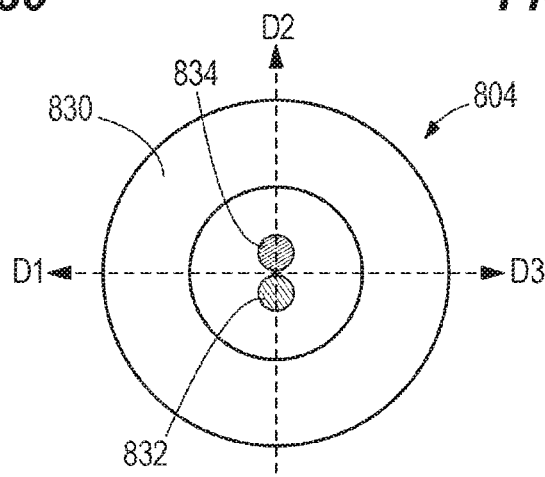
FIG. 32 is another cross-sectional view of an embodiment of the shaft of the articulating stylet of FIG. 30 at the location indicated in FIG. 24.

FIG. 32 is a cross-sectional view of an embodiment of the shaft 804 at the location indicated on FIG. 24. In FIG. 32, both the first cable route 832 and the second cable route 834 are disposed in the center of the lumen 830.

Figure 33:
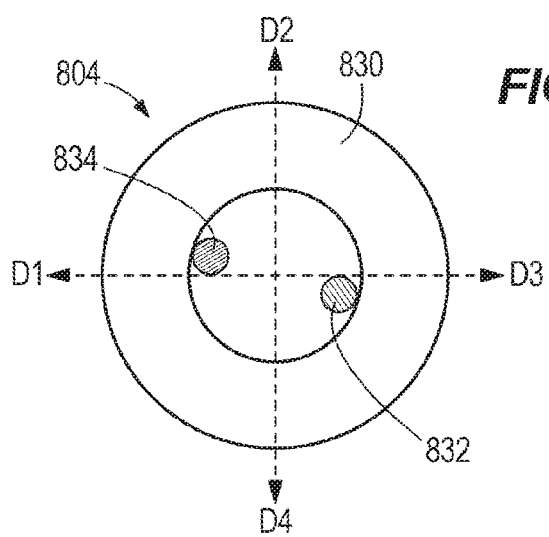
FIG. 33 is another cross-sectional view of an embodiment of the shaft of the articulating stylet of FIG. 30 at the location indicated in FIG. 24.

FIG. 33 is a cross-sectional view of an embodiment of the shaft 804 at the location indicated on FIG. 24. In FIG. 33, the first cable route 832 is disposed in the lumen 830 towards the direction D3 and the second cable route 834 is disposed in the lumen 830 towards the direction D1.

Figure 34:
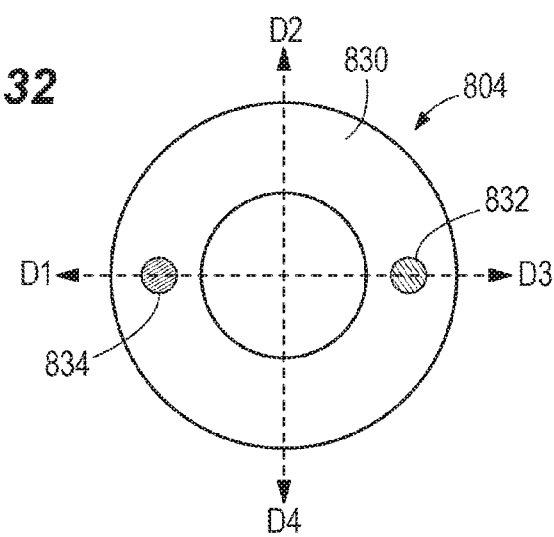
FIG. 34 is another cross-sectional view of an embodiment of the shaft of the articulating stylet of FIG. 30 at the location indicated in FIG. 24.

FIG. 34 is a cross-sectional view of an embodiment of the shaft 804 at the location indicated on FIG. 24. In FIG. 34, the first cable route 832 is disposed in the shaft 804 in the direction of D3 and the second cable route 834 is disposed in the shaft 804 in the direction of D1. As is illustrated by the sequence of cross-sectional views in FIGS. 30-34, the first cable route 832 and the second cable route 834 each switch to the opposite side of the shaft 804 by crossing through the lumen 830. In this manner, the first cable 812 connects a first radial side of the tip control lever 802 to the opposite side of the tip 808. Similarly, the second cable 814 connects a first radial side of the tip control lever 802 to the opposite radial side of the tip 808.

FIG. 35 is a perspective view of an embodiment of a pyramidal-shaped articulating disc 860. In some embodiments, the pyramidal-shaped articulating disc 860 includes a first articulating surface 862 and a second articulating surface 864. Both the first articulating surface 862 and the second articulating surface 864 are configured to contact and articulate against surfaces of adjacent articulating discs towards directions D1 or D3. This is shown and described in greater detail with respect to FIG. 36. Although shown with a rectangular cross-section, some embodiments the pyramidal-shaped articulating disc 860 have a round or circular cross-section. However, other embodiments of the pyramidal-shaped articulating disc 860 have other cross-sectional shapes.

In some embodiments, the first articulating surface 862 is formed from a first surface 866 and a second surface 868 that meet in a ridge 870. In some embodiments, the first surface 866 and the second surface 868 are flat surfaces. In some embodiments, the ridge 870 is angular and has an angle of between 135 degrees and 179 degrees. Other embodiments with larger or smaller angles are possible as well. In other embodiments, the first surface 866 and the second surface 868 meet at a flat or rounded ridge.

Similarly, the second articulating surface 864 is formed from a first surface 872 and a second surface 874 that meet in a ridge 876. In some embodiments, the first surface 872 and the second surface 874 are flat surfaces. In some embodiments, the ridge 876 is angular and has an angle of between 135 degrees and 179 degrees. Other embodiments with larger or smaller angles are possible as well. In other embodiments, the first surface 872 and the second surface 874 meet at a flat or rounded ridge.

FIG. 36 is a side view of an embodiment of a structure 878. The structure 878 includes the first cable 812, the second cable 814, a first pyramidal-shaped articulating disc 880, and a second pyramidal-shaped articulating disc 882. The first cable 812 and the second cable 814 pass through opposite ends of both the first pyramidal-shaped articulating disc 880 and the second pyramidal-shaped articulating disc 882. In use, tension may be applied to the first cable 812 or the second cable 814 by pulling on the respective cable.

In the example shown in FIG. 36, the first cable 812 is under tension, while the second cable 814 is relaxed. The tension in the first cable 812 pulls the edges nearest the first cable 812 of the first pyramidal-shaped articulating disc 880 and the second pyramidal-shaped articulating disc 882 together. Because the second cable 814 is relaxed, it allows the edges nearest the first cable 812 of the first pyramidal-shaped articulating disc 880 and the second pyramidal-shaped articulating disc 882 to separate. In this manner, the structure 878 bends or moves in the direction D1. Conversely, by creating tension in the second cable 814 and relaxing the first cable 812, the structure 878 will bend or move towards direction D3 instead.

Additionally, the structure 878 can also be used to create tension in or relax the first cable 812 or the second cable 814. By physically rotating the first pyramidal-shaped articulating disc 880 towards direction D1 while the second pyramidal-shaped articulating disc 882 is held in place, the first cable 812 is relaxed and the second cable 814 is put under tension.

In some embodiments of the articulating stylet 800, one or more of the structure 878 are included in the tip control lever 802 or the tip 808.

FIG. 37 is a perspective view of an embodiment of a round-shaped articulating disc 910. In some embodiments, the round-shaped articulating disc 910 includes a first articulating surface 912 and a second articulating surface 914. Both the first articulating surface 912 and the second articulating surface 914 are configured to contact and articulate against surfaces of adjacent articulating discs towards directions D1 or D3. This is shown and described in greater detail with respect to FIG. 38. In some embodiments, the first articulating surface 912 is round. Similarly, in some embodiments, the second articulating surface 914 is also round. Although shown with a rectangular cross-section, some embodiments the round-shaped articulating disc 910 have a round or circular cross-section. However, other embodiments of the pyramidal-shaped articulating disc 860 have other cross-sectional shapes.

FIG. 38 is a side view of an embodiment of a structure 940. The structure 940 includes the first cable 812, the second cable 814, a first round-shaped articulating disc 942, and a second round-shaped articulating disc 944. The first cable 812 and the second cable 814 pass through opposite ends of the first round-shaped articulating disc 942 and the second pyramidal-shaped articulating disc 944. In use, tension may be applied to the first cable 812 or the second cable 814 by pulling on the respective cable.

In the example shown in FIG. 38, the first cable 812 is under tension, while the second cable 814 is relaxed. The tension in the first cable 812 pulls the edges nearest the first cable 812 of the first round-shaped articulating disc 942 and the second round-shaped articulating disc 944 together. Because the second cable 814 is relaxed, it allows the edges nearest the second cable 814 of the first round-shaped articulating disc 942 and the second round-shaped articulating disc 944 to separate. In this manner, the structure 940 bends or moves in the direction D1. Conversely, by creating tension in the second cable 814 and relaxing the first cable 812, the structure 940 will bend or move in direction D3 instead.

Additionally, the structure 940 can also be used to create tension in or relax the first cable 812 or the second cable 814. By physically rotating the first round-shaped articulating disc 942 towards direction D1 while the second round-shaped articulating disc 944 is held in place, the first cable 812 is relaxed and the second cable 814 is put under tension.

In some embodiments of the articulating stylet 800, one or more of the structure 940 are included in the tip control lever 802 or the tip 808.

FIG. 39 is a side view of an embodiment of the articulating stylet 800. In this example, the tip control lever 802 is bent into position LP3, causing the first cable 812 to relax and the second cable 814 to be under tension. The first cable 812 and the second cable 814 cross in the middle of the shaft 804. Accordingly, the tension in the second cable 814 causes the tip 808 to bend into position TP1. In this example, the lever position LP3 and the tip position TP1 are both bent in substantially the same direction.

FIG. 40 is a side view of another embodiment of the articulating stylet 800. The embodiment shown in FIG. 40 is similar to the embodiment shown in FIG. 39, except that the first cable 812 and the second cable 814 do not cross in the shaft 804. In this example, the tip control lever 802 is bent into position LP4, causing the first cable 812 to be under tension and the second cable 814 to relax. The tension in the first cable 812 causes the tip 808 to bend into position TP1. In this example, the lever position LP4 and the tip position TP1 are bent in different directions.

Figure 41:
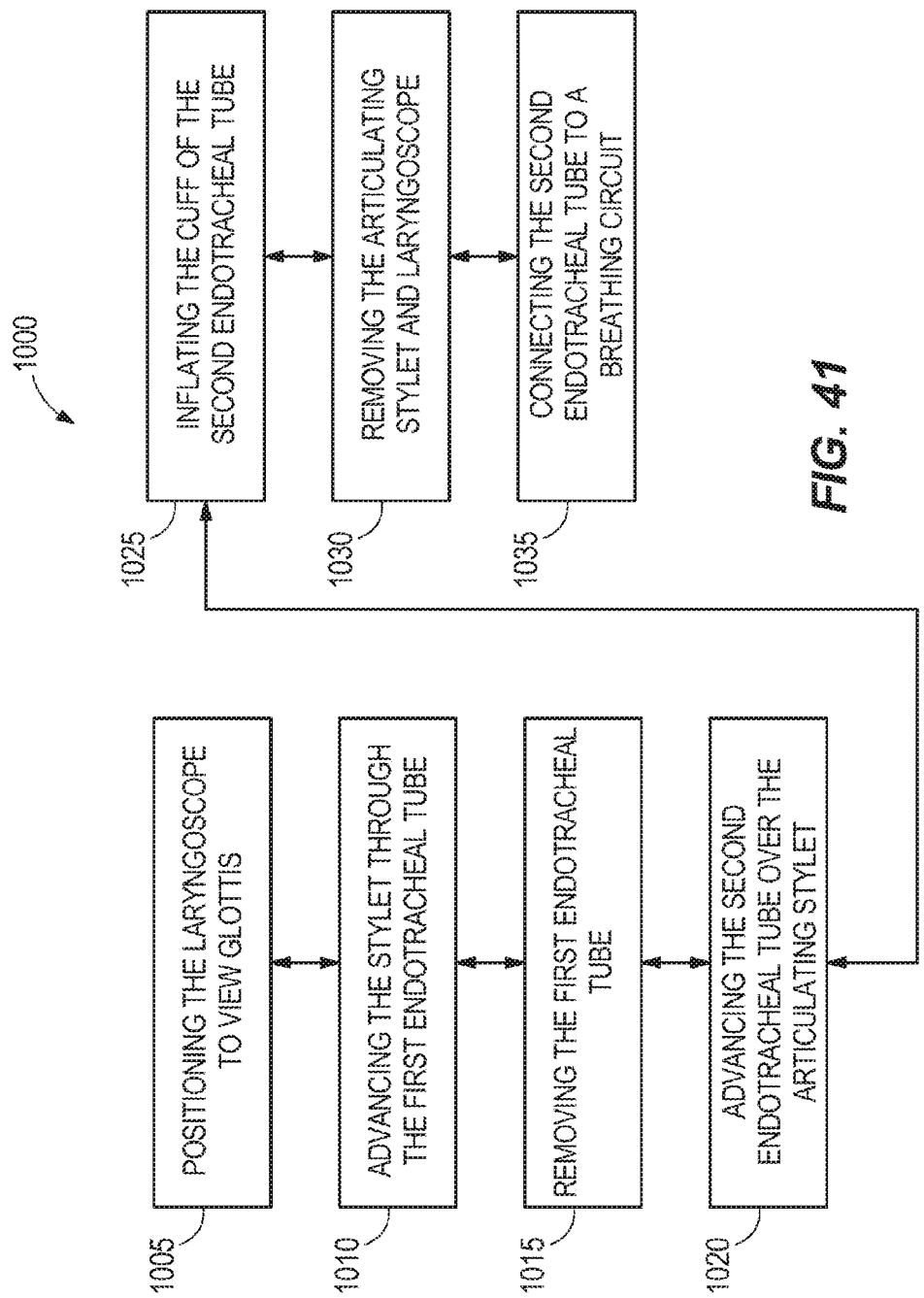
FIG. 41 is a flowchart of an example endotracheal tube exchange process using an embodiment of the articulating stylet of FIG. 19.

FIG. 41 is a flowchart of an example endotracheal tube exchange process 1000 for removing an existing first endotracheal tube and replacing it with a new second endotracheal tube using an example tracheal intubation system including a laryngoscope. In some embodiments, the articulating stylet includes a tip control lever, a shaft, and a tip that is directed by the lever.

Figure 42:
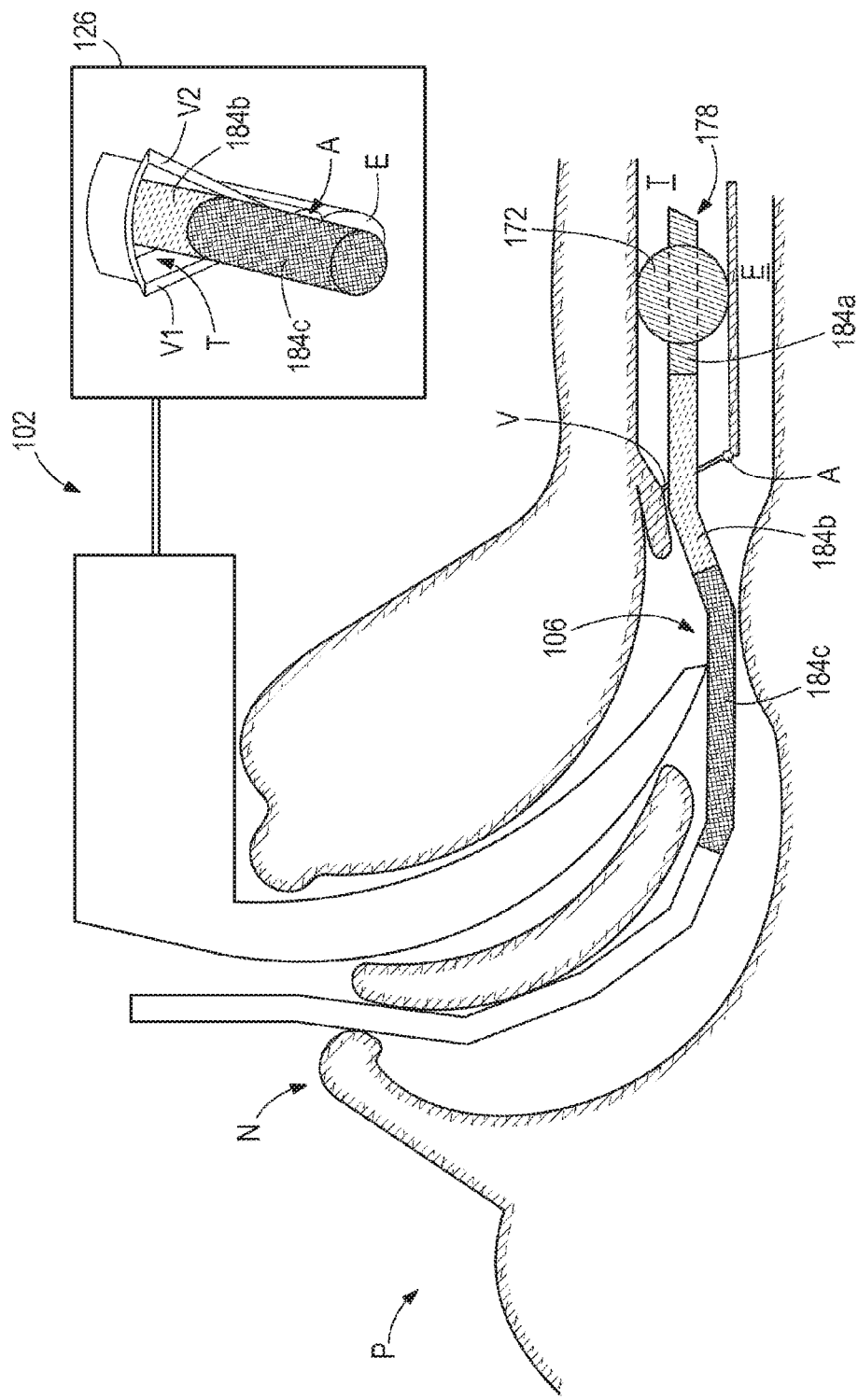
FIG. 42 is a cross-sectional view of a patient during an endotracheal tube exchange procedure using an example tracheal intubation system including a laryngoscope.

Initially, at operation 1005, the laryngoscope is positioned to view the glottis of the patient. This step is similar to step 700 of the process illustrated and described in greater detail with respect to FIG. 7. When the laryngoscope is properly positioned, both the glottis and the existing first endotracheal tube will be visible in the field of view of the laryngoscope. The position of the laryngoscope and the field of view of the laryngoscope are best illustrated in FIG. 42.

Figure 43:
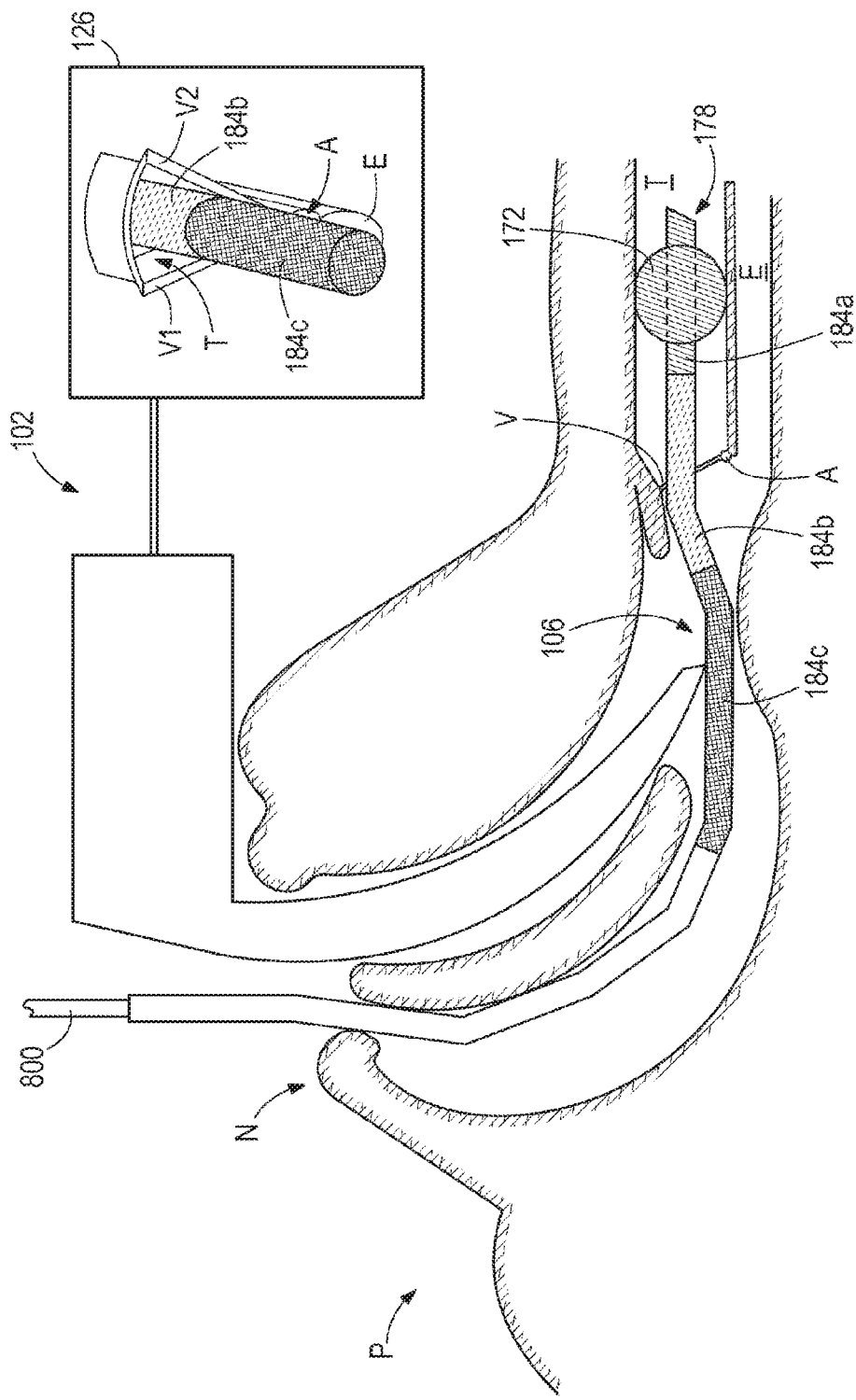
FIG. 43 is a cross-sectional view of a patient P during an endotracheal tube exchange procedure using an example tracheal intubation system including a laryngoscope.

Next, at operation 1010, the tip of the articulating stylet is positioned in the existing first endotracheal tube and advanced until it reaches or goes beyond the tip of the existing first endotracheal tube. This ensures that the tip of the articulating stylet is in the trachea. The shaft of the articulating stylet includes markers that indicate the distance from the marker to the tip of the articulating stylet. By monitoring these markers on the shaft of the articulating stylet, a caregiver can determine when the articulating stylet is fully inserted through the endotracheal tube. In some embodiments, the endotracheal tube is transparent or translucent, and the caregiver monitors markers (e.g., the depth-assessment bands) on or near the tip of the articulating stylet to determine the position of the tip of the articulating stylet. In other embodiments, the caregivers monitors a series of numbers on the shaft of the articulating stylet that correspond to the distance from the number to the tip of the articulating stylet to determine the position of the tip of the articulating stylet. These numbers on the shaft of the articulating stylet can be compared to the proximal end of the endotracheal tube. Because the length of the endotracheal tube is known, the position of the tip of the articulating stylet can be determined relative to it. The final position of the articulating stylet after operation 1010 is best illustrated in FIG. 43.

Figure 44:
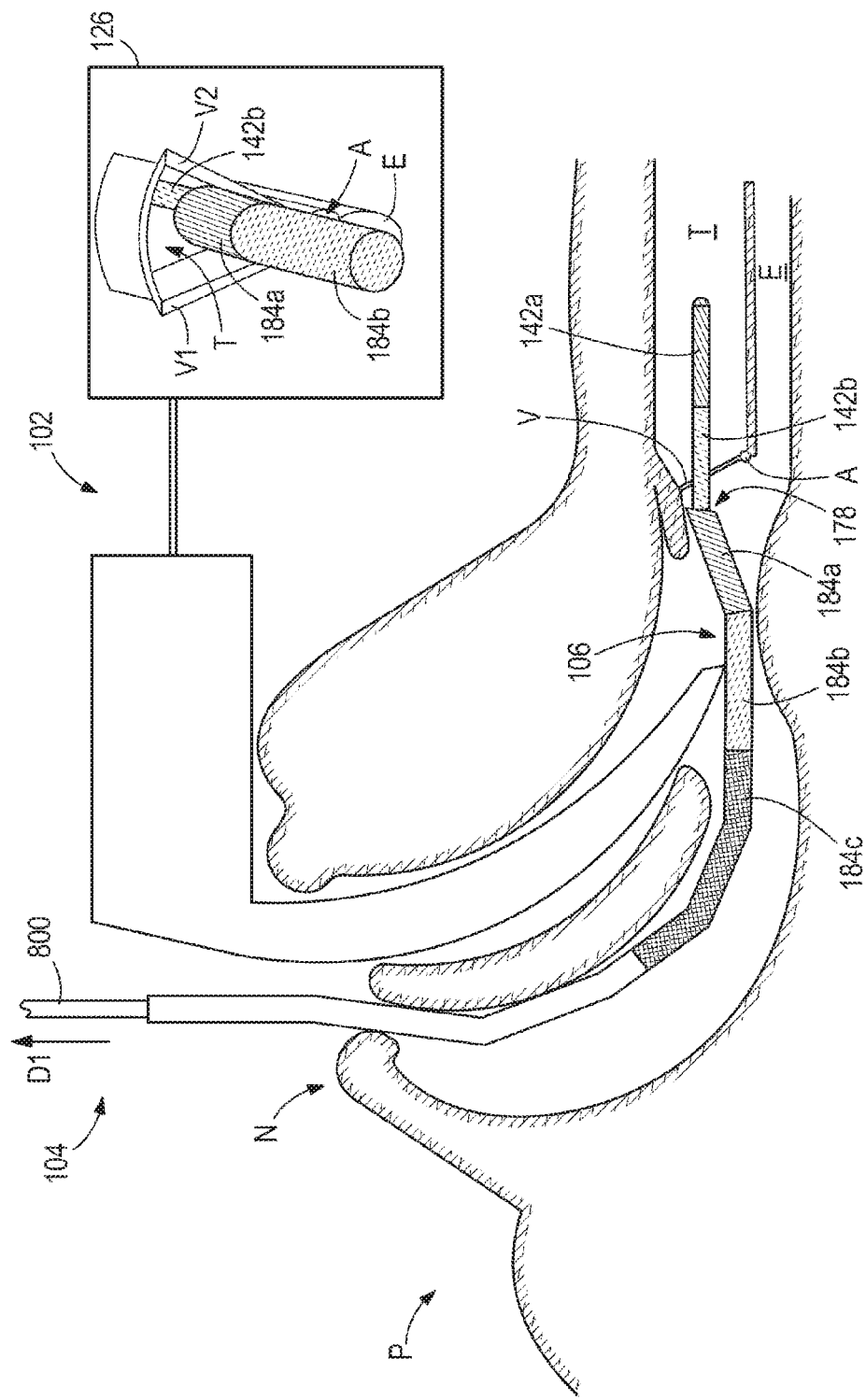
FIG. 44 is cross-sectional view of a patient P during an endotracheal tube exchange procedure using an example tracheal intubation system including a laryngoscope.
Figure 45:
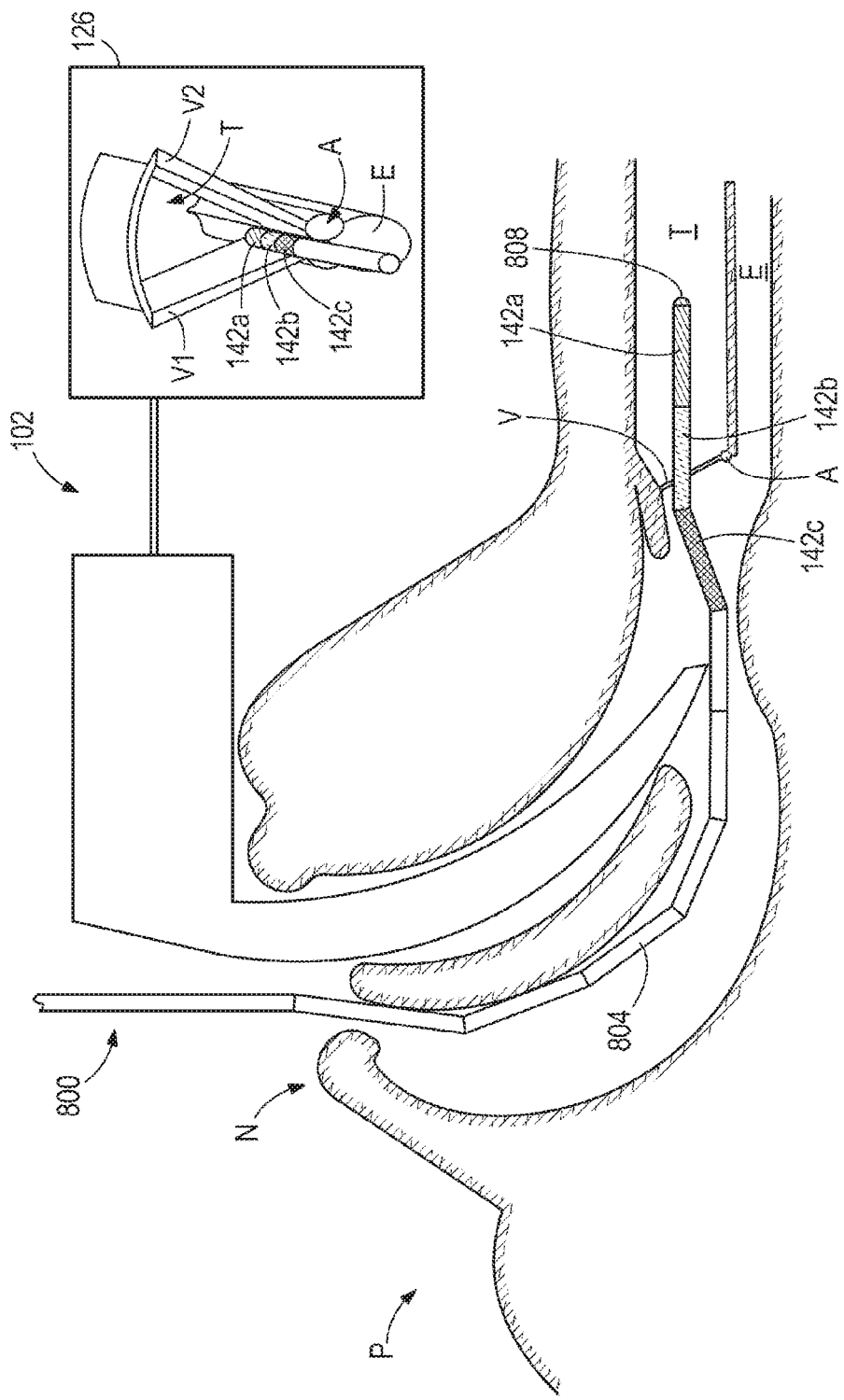
FIG. 45 is cross-sectional view of a patient P during an endotracheal tube exchange procedure using an example tracheal intubation system including a laryngoscope.

At operation 1015, the existing first endotracheal tube is removed. In some embodiments, a cuff of the existing first endotracheal tube is deflated. However, in some embodiments the endotracheal tube does not include a cuff. Then, the existing first endotracheal tube is advanced over the articulating stylet towards the lever. In this manner, the existing first endotracheal tube is removed from the patient. A caregiver continues to advance the existing first endotracheal tube until it is completely pulled over the lever of the articulating stylet and off of the articulating stylet. Throughout this operation, the caregiver monitors the depth-assessment bands on the tip of articulating stylet using the laryngoscope to ensure that the articulating stylet does not move into or out of the patient's trachea. As described with respect to operation 1010, the position of the tip of the articulating stylet can be determined by monitoring the depth-assessment bands on the tip of the articulating stylet through a transparent or translucent endotracheal tube or by monitoring depth markers on the shaft of the articulating stylet. This operation is best shown in FIGS. 44 and 45.

Figure 46:
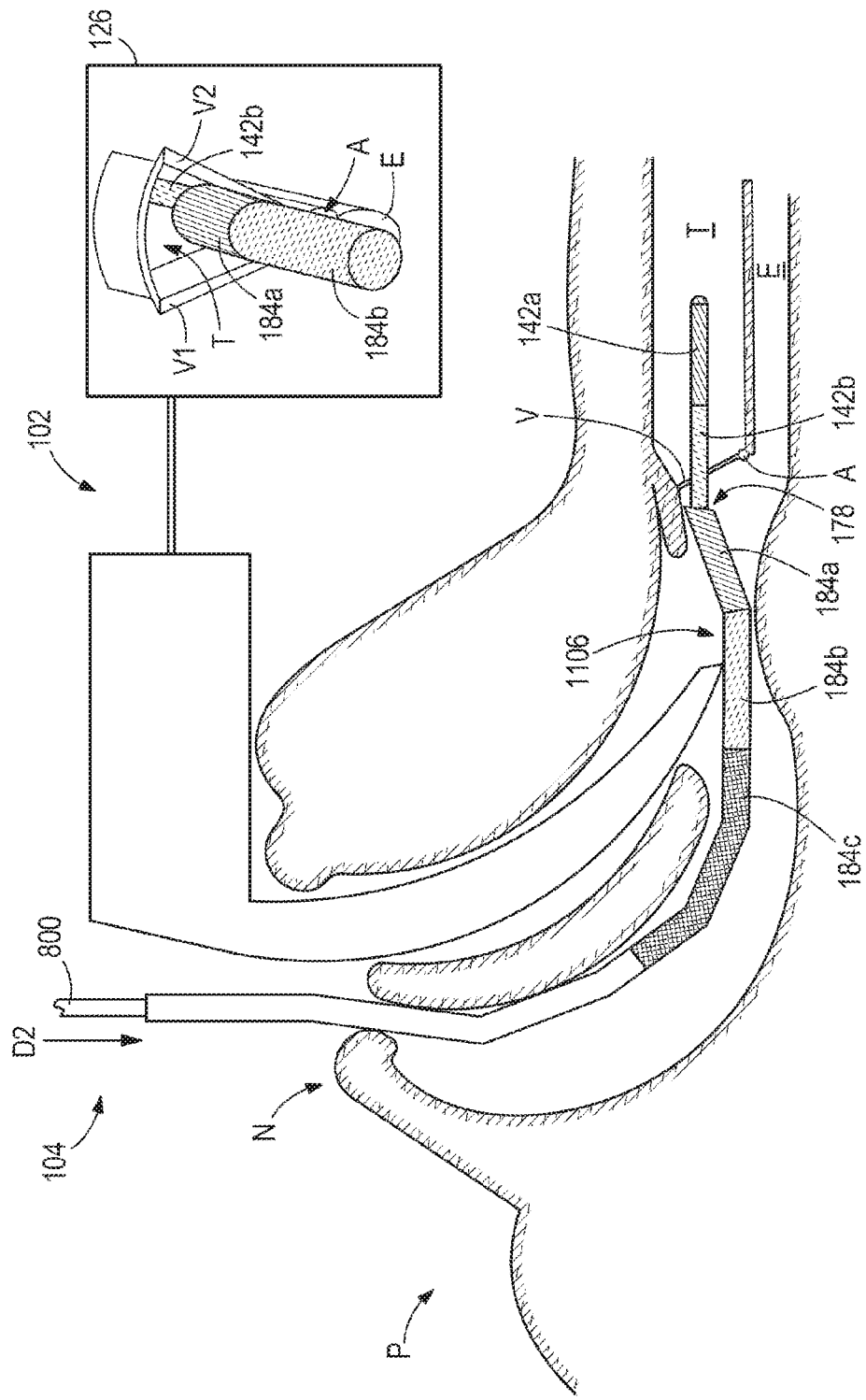
FIG. 46 is cross-sectional view of a patient P during an endotracheal tube exchange procedure using an example tracheal intubation system including a laryngoscope.

At operation 1020, the new second endotracheal tube is loaded over the lever of the articulating stylet and advanced over the shaft of the articulating stylet. In some embodiments, a caregiver, usually a physician or person assisting a physician grabs the endotracheal tube and slides it along the articulating stylet until the first end of the endotracheal tube enters the trachea of the patient. Throughout this operation, the caregiver also monitors the depth-assessment bands on the tip of articulating stylet using the laryngoscope to ensure that the tip of the articulating stylet does not move into or out of the patient's trachea. As described with respect to operation 1010, the position of the tip of the articulating stylet can be determined by monitoring the depth-assessment bands on the tip of the articulating stylet through a transparent or translucent endotracheal tube or by monitoring depth markers or numbers on the shaft of the articulating stylet. This operation is best shown in FIG. 46.

Figure 47:
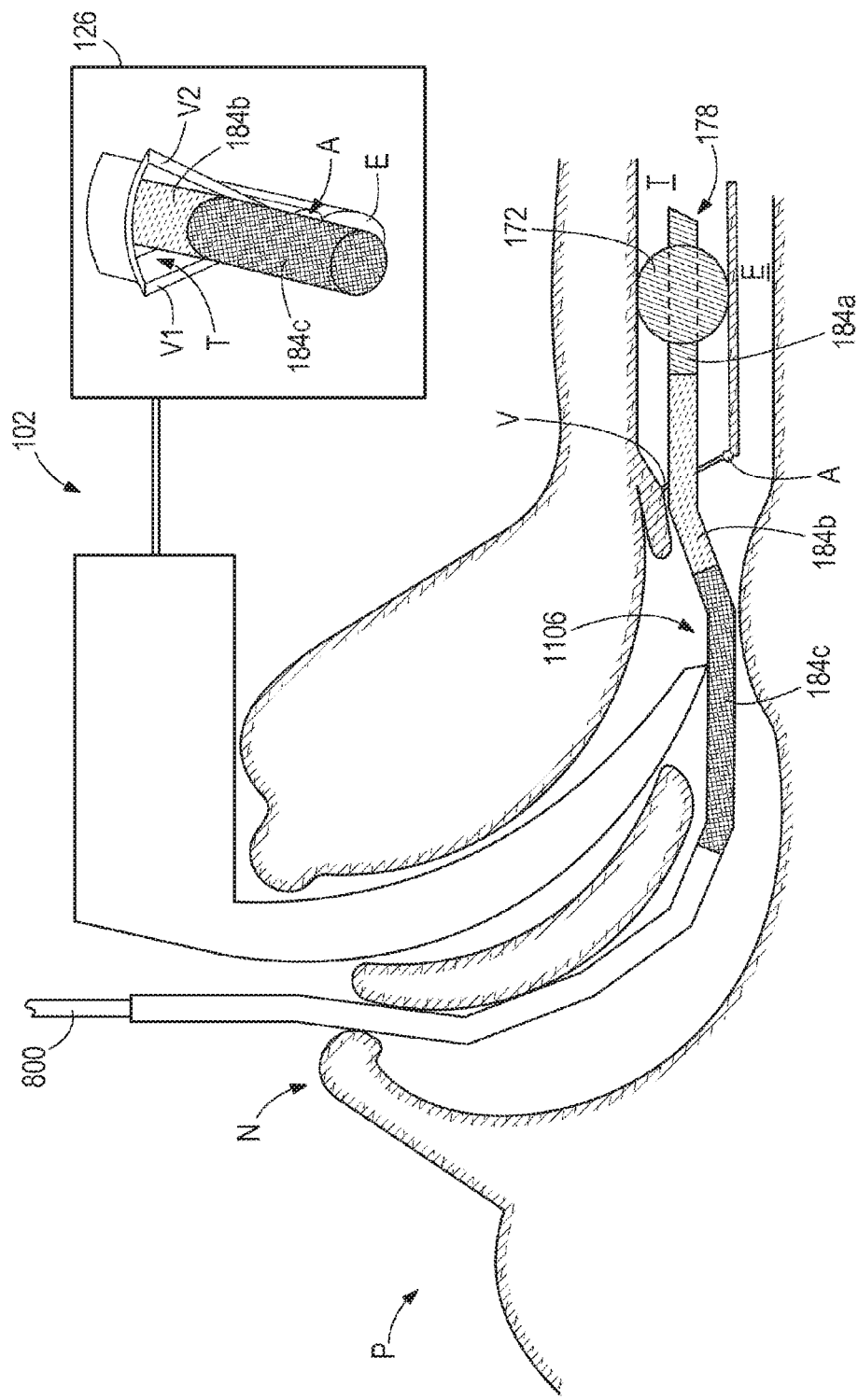
FIG. 47 is cross-sectional view of a patient P during an endotracheal tube exchange procedure using an example tracheal intubation system including a laryngoscope.

At operation 1025, the cuff of the endotracheal tube is inflated. This operation is similar to operation 730 of the process illustrated and described in greater detail with respect to FIG. 7. However, in embodiments where the endotracheal tube does not include a cuff, this operation 1025 is not performed. The endotracheal tube with expanded cuff is illustrated in FIG. 47.

At operation 1030, the articulating stylet and laryngoscope are removed. The shaft of the articulating stylet is pulled out of the endotracheal tube, leaving the endotracheal tube in place. This operation is similar to operation 735 of the process illustrated and described in greater detail with respect to FIG. 7.

At operation 1035, the endotracheal tube is connected to a ventilator or breathing circuit to provide ventilation for the patient. This operation is similar to operation 740 of the process illustrated and described in greater detail with respect to FIG. 7.

If the articulating stylet is removed from the trachea of the patient at any point during the endotracheal tube exchange process 1000, the caregiver can notice this with the laryngoscope. The caregiver can then redirect the articulating stylet back into the trachea using the articulating tip as described in operations 715 and 720 of the process illustrated in and described in greater detail with respect to FIG. 7.

FIG. 42 is a cross-sectional view of a patient P during an endotracheal tube exchange procedure using an example tracheal intubation system including a laryngoscope. In this example, the existing first endotracheal tube 106 is currently positioned in the trachea of the patient T and the cuff 172 is inflated. However, in some embodiments, the endotracheal tube 106 does not include the inflatable cuff 172. The blade 110 of the laryngoscope 102 is disposed in the pharynx of the patient P. The blade 110 is oriented so that the field of view of the optical capture device on blade 110 includes the vocal cords V and trachea T of the patient P, as well as the existing first endotracheal tube 106. The screen 126 displays that the endotracheal tube 106 is positioned in the trachea T.

FIG. 43 is a cross-sectional view of a patient P during an endotracheal tube exchange procedure using an example tracheal intubation system including a laryngoscope. In this example, the articulating stylet 800 is inserted into the existing first endotracheal tube 106.

FIG. 44 is cross-sectional view of a patient P during an endotracheal tube exchange procedure using an example tracheal intubation system including a laryngoscope. In this example, the existing first endotracheal tube 106 is being advanced in the direction D1 along the articulating stylet 800 out of the trachea T of the patient P and towards the tip control lever 802 of the articulating stylet 800.

FIG. 45 is cross-sectional view of a patient P during an endotracheal tube exchange procedure using an example tracheal intubation system including a laryngoscope. In this example, the existing first endotracheal tube 106 has been fully removed and is no longer shown. The articulating stylet 800 remains in the proper position in the trachea T of the patient P. The position of the tip 808 of the articulating stylet 800 can be monitored on the screen 126 using the depth-assessment bands 142.

FIG. 46 is cross-sectional view of a patient P during an endotracheal tube exchange procedure using an example tracheal intubation system including a laryngoscope. In this example, the new second endotracheal tube 1106 is being advanced in the direction D2 along the articulating stylet 800 into the trachea T of the patient P.

FIG. 47 is cross-sectional view of a patient P during an endotracheal tube exchange procedure using an example tracheal intubation system including a laryngoscope. In this example, the new second endotracheal tube 1106 has been fully advanced along the articulating stylet 800 and is properly positioned in the trachea T of the patient P. In some embodiments, the cuff 172 is expanded to secure the new second endotracheal tube 1106 in place. However, in some embodiments, the endotracheal tube 1106 does not include the inflatable cuff 172.

Figure 48:
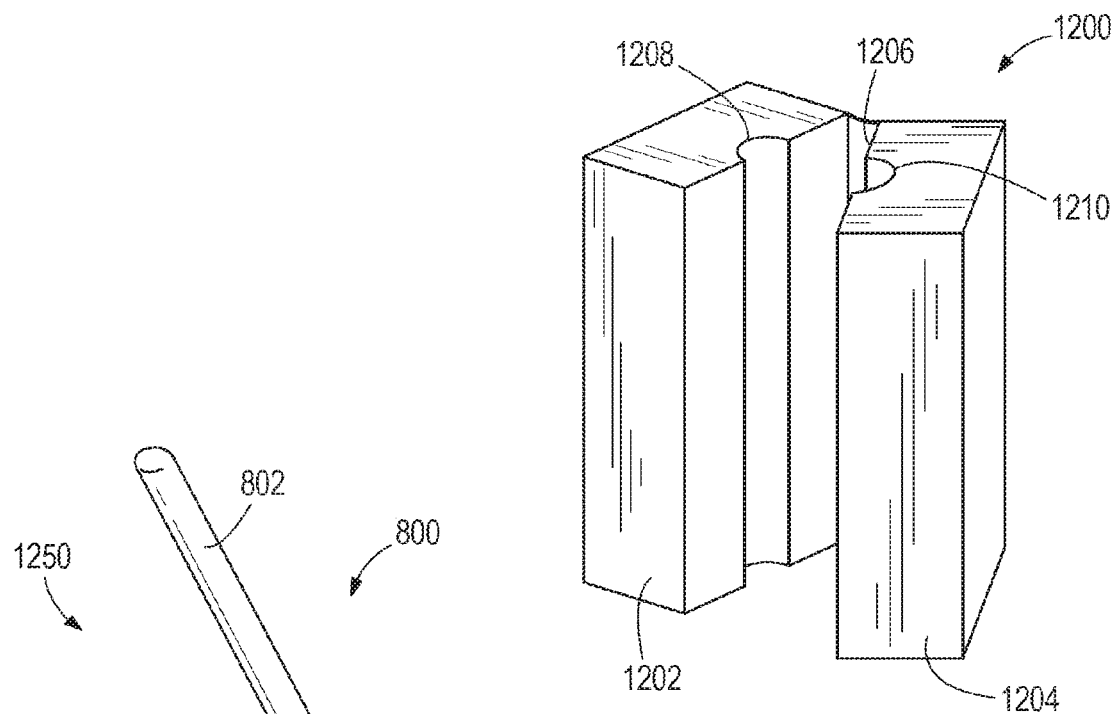
FIG. 48 is a perspective view of an embodiment of a removable handle for the articulating stylet of FIG. 19.

FIG. 48 is a perspective view of an embodiment of a removable handle 1200 for the articulating stylet 800. The removable handle 1200 includes a first portion 1202 and a second portion 1204. However, some embodiments of the articulating stylet 800 do not include a handle, removable or otherwise.

The first portion 1202 and the second portion 1204 are physical structures and are configured to be gripped. In some embodiments, the first portion 1202 and the second portion 1204 are formed from rigid or semi-rigid materials. In some embodiment, the first portion 1202 and the second portion 1204 are formed from plastic or rubber. Yet other embodiments of the first portion 1202 and the second portion 1204 are possible as well. In some embodiments, either or both of the first portion 1202 and the second portion 1204 include finger-shaped grooves to provide an ergonomic and comfortable grip for the caregiver.

In some embodiments, the first portion 1202 and the second portion 1204 are joined by a joint 1206. The joint 1206 is an apparatus the couples the first portion 1202 to the second portion 1204 and allows movement between an open position and a closed position. In some embodiments, the joint 1206 is a rotational hinge and is configured to allow the first portion 1202 to rotate relative to the second portion 1204 between an open position and a closed position. In other embodiments, the joint 1206 is a different rotational device. In yet other embodiments, the joint 1206 is flexible and bends to allow movement between the open position and the closed position. Yet other embodiments of joint 1206 are possible as well. Additionally, some embodiments of the removable handle include a latching mechanism, such as a latch, hook, or clasp to removably secure the removable handle 1200 in the closed position.

The first portion 1202 includes a first groove 1208. Similarly, the second portion 1204 includes a corresponding second groove 1210. The first groove 1208 and the second groove 1210 are configured to fit against the shaft 804 of the articulating stylet 800. In the closed position, the first groove 1208 and the second groove 1210 are configured to wrap around the shaft 804 of the articulating stylet 800. In this manner, the removable handle can be secured to and removed from the shaft of the articulating stylet 800. In some embodiments, the surface of one or both of the first groove 1208 and the second groove 1210 are textured to improve the grip on the shaft 804 of the articulating stylet 800. In other embodiments, one or both of the first grove 1208 and the second groove 1210 are lined with a material, such as a high friction material, to improve the grip on the shaft 804 of the articulating stylet 800.

Figure 49:
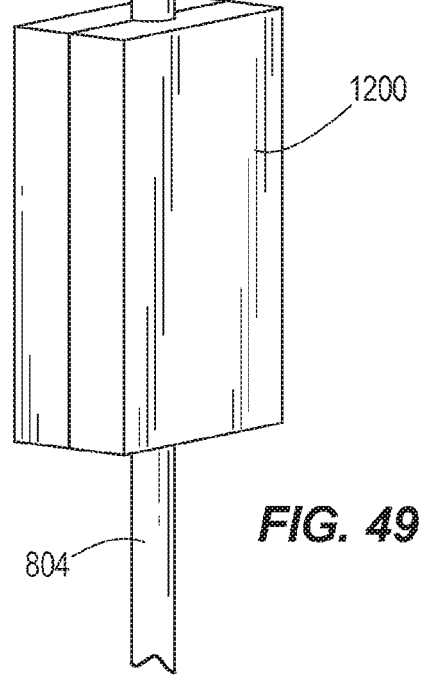
FIG. 49 is a perspective view of the embodiment of the removable handle of FIG. 48 coupled to the articulating stylet of FIG. 19.

FIG. 49 is a perspective view of an articulating stylet system 1250. The articulating stylet system 1250 includes the articulating stylet 800 and the removable handle 1200. In some embodiments, the removable handle 1200 is removably coupled to the articulating stylet 800. In the example shown, the removable handle 1200 is removably coupled to the shaft 804 of the articulating stylet 800 below the tip control lever 802. A caregiver can couple the removable handle 1200 to the shaft 804 when the caregiver needs to control the tip 808 of the articulating stylet 800. The caregiver can then remove the removable handle 1200 as necessary to remove or insert an endotracheal tube 106 over the tip control lever 802 of the articulating stylet 800.

Figure 50:
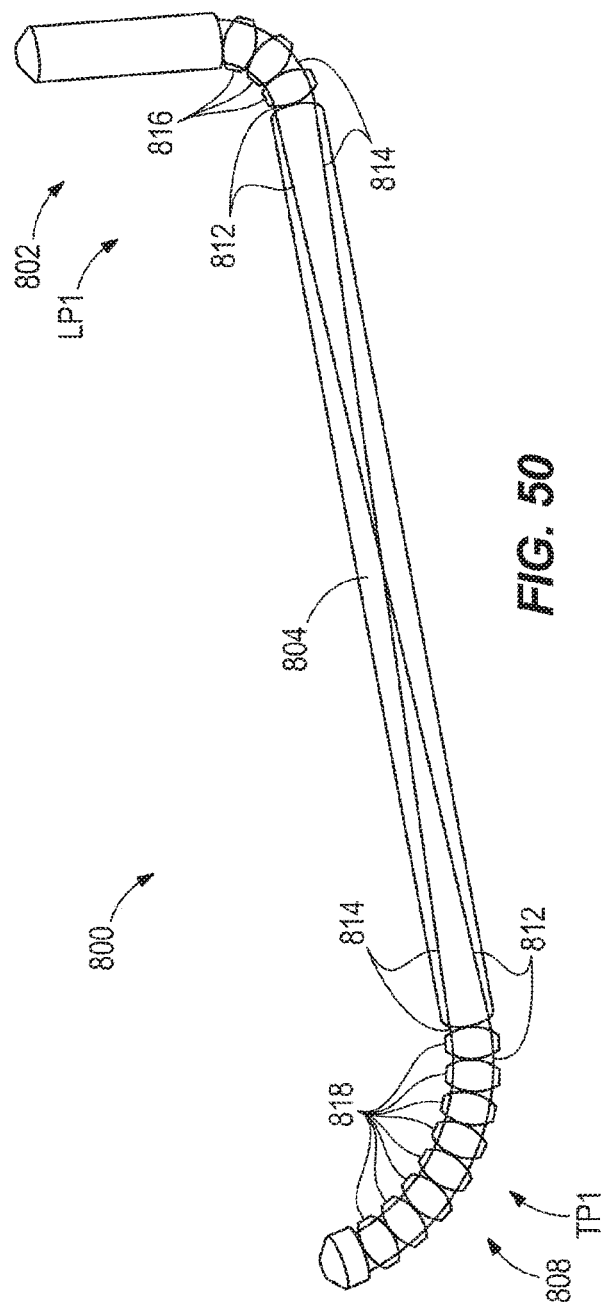
FIG. 50 is a side view of an embodiment of the articulating stylet of FIG. 19.

FIG. 50 is a side view of an embodiment of the articulating stylet 800. In this example, the tip control lever 802 is rigid and is rotated into position LP1, causing the first cable 812 to relax and the second cable 814 to be under tension. Although the tip control lever 802 is rigid, it is joined to the shaft 804 with a plurality of articulating discs 816. The first cable 812 and the second cable 814 cross in the middle of the shaft 804. Accordingly, the tension in the second cable 814 causes the tip 808 to bend into position TP1. In this example, the lever position LP1 and the tip position TP1 are both bent in substantially the same direction.

Figure 51:
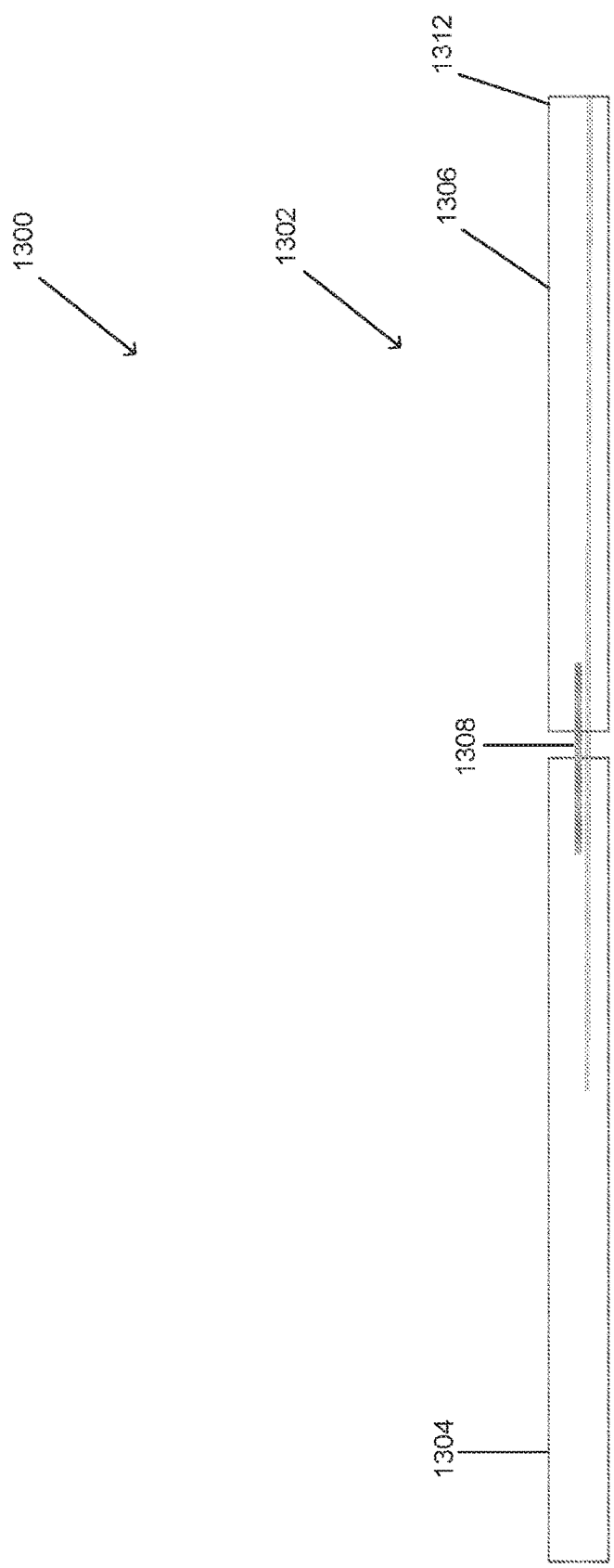
FIG. 51 is a schematic diagram of an embodiment of an articulating stylet.

Turning now to FIG. 51, a schematic diagram of an embodiment of an articulating stylet 1300 is shown. The articulating stylet 1300 allows for control of a tip 1312. The articulating stylet 1300 is an example of the articulating stylet 104. The articulating stylet 1300 includes a shaft 1302, which includes a proximal shaft portion 1304 and a distal shaft portion 1306 that are joined by an expanding connector 1308. Embedded within the shaft 1302 is a control wire 1310. In this example, the control wire 1310 is connected at one end to the tip 1312 and at the other end to the proximal shaft portion 1304.

The expanding connector 1308 connects the proximal shaft portion 1304 to the distal shaft portion 1306 and allows the distance between the distal shaft portion 1306 and proximal shaft portion 1304 to be adjusted. The expanding connector 1308 includes a sliding assembly in some embodiments. The sliding assembly may include one or more pins that are disposed in a lumen in the proximal shaft portion 1304 and the distal shaft portion 1306 and upon which one or both of the proximal shaft portions 1304 and distal shaft portion 1306 slide. Other embodiments of the expanding connector 1308 are possible as well.

When the distal shaft portion 1306 is separated from the proximal shaft portion 1304, the control wire 1310 is pulled. By pulling the control wire 1310, the control wire is put under tension, which causes the tip 1312 to move.

Figure 52:
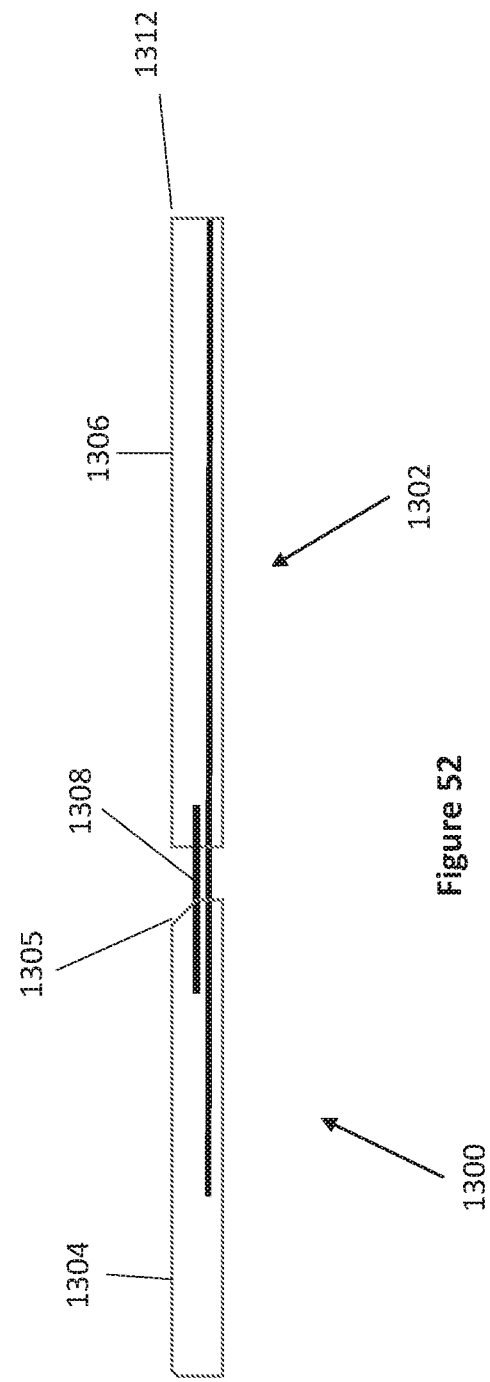
FIG. 52 is a schematic diagram of an embodiment of an articulating stylet.

FIG. 52 illustrates a schematic diagram of an embodiment of an articulating stylet 1300. The articulating stylet 1300 allows for control of a tip 1312. The articulating stylet 1300 is an example of the articulating stylet 104. The articulating stylet 1300 includes a shaft 1302, which includes a proximal shaft portion 1304 and a distal shaft portion 1306 that are joined by an expanding connector 1308. The proximal shaft portion 1304 includes an indentation 1305 at a distal end. Embedded within the shaft 1302 is a control wire 1310. In this example, the control wire 1310 is connected at one end of the distal shaft portion 1306 to the tip 1312 and extends to the proximal shaft portion 1304.

The expanding connector 1308 connects the proximal shaft portion 1304 to the distal shaft portion 1306 and allows the distance between the distal shaft portion 1306 and proximal shaft portion 1304 to be adjusted. The expanding connector 1308 includes a sliding assembly in some embodiments. The sliding assembly may include one or more pins that are disposed in a lumen in the proximal shaft portion 1304 and the distal shaft portion 1306 and upon which one or both of the proximal shaft portions 1304 and distal shaft portion 1306 slide. Other embodiments of the expanding connector 1308 are possible as well.

When the distal shaft portion is separated from the proximal shaft portion 1304, the control wire 1310 is pulled. By pulling the control wire 1310, the control wire is put under tension, which causes the tip 1312 to move.

Figure 53:
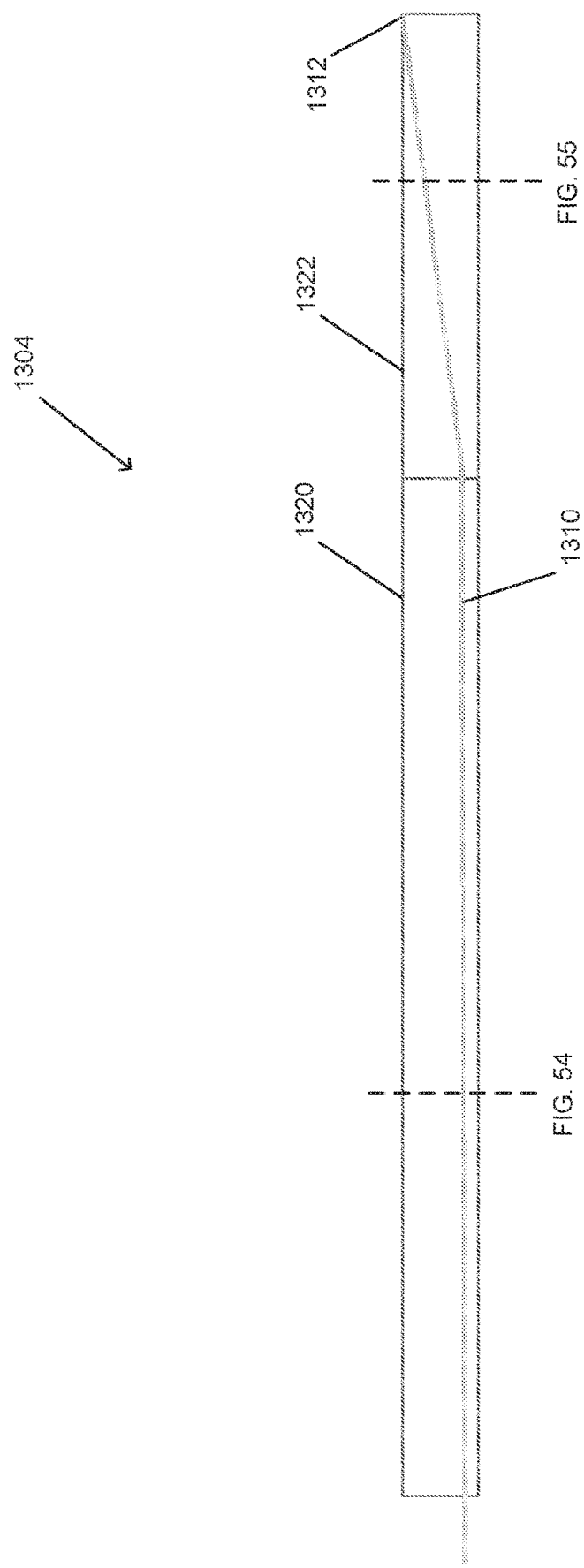
FIG. 53 is a schematic diagram of an embodiment of shaft portion of the articulating stylet.

Turning now to FIG. 53, a schematic diagram of an embodiment of the distal shaft portion 1304 of an articulating stylet 1300 is shown. In this example, the distal shaft portion 1304 includes a proximal shaft body portion 1320 and a distal shaft portion 1322. In some embodiments, the proximal shaft body portion 1320 is more rigid than the distal shaft portion 1322. In other words, the distal shaft tip portion 1322 is more flexible than the proximal shaft portion 1320. For example, the proximal shaft body portion 1320 may be formed from a more rigid material such as a plastic having a higher rigidity and the distal shaft tip portion 1322 is formed from a more flexible material such as a plastic that has a lower rigidity. In this manner, when the wire 1310 under tension from being pulled by the proximal shaft body portion 1320, the tension causes the more flexible distal shaft portion 1322 to deform, causing the tip 1312 to move. As shown in the example of FIG. 53, the wire 1310 is connected to a corner of the tip 1312. As the wire 1310 is pulled, the tip is pulled towards the corner where the wire 1310 is joined. In some embodiments, the proximal shaft body portion 1320 and the distal shaft body portion 1322 are formed integrally. Alternatively, the proximal shaft body portion 1320 and the distal shaft body portion 1322 are formed separately and joined together (e.g., with a weld such as a butt weld, an adhesive, or a coupling device). Cross sections of the proximal shaft body portion 1320 and the proximal shaft tip portion are illustrated further in FIGS. 55 and 56 respectively.

The distal shaft portion 1304 includes a proximal shaft body portion 1320 and a distal shaft portion 1322. While the proximal shaft body portion 1320 is more rigid than the distal shaft portion 1322. In other words, the distal shaft tip portion 1322 is more flexible than the proximal shaft portion 1320. For example, the proximal shaft body portion 1320 may be formed from a more rigid material such as a plastic having a higher rigidity and the distal shaft tip portion 1322 is formed from a more flexible material such as a plastic that has a lower rigidity.

Figure 54:
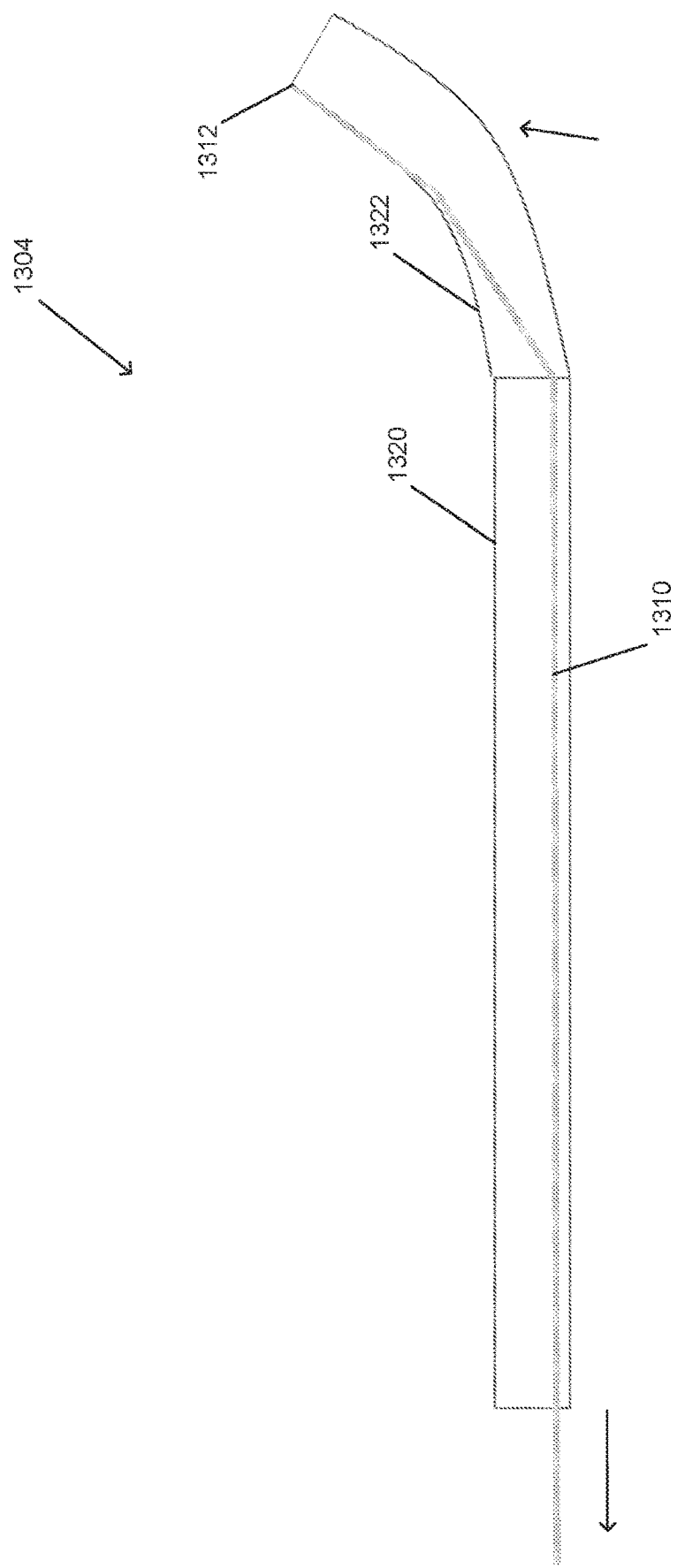
FIG. 54 is a schematic diagram of an embodiment of a distal shaft portion when a wire is under tension.

Turning now to FIG. 54, an embodiment of the proximal shaft portion 1304 is illustrated when the wire 1310 is under tension. As described previously, the distal shaft body portion 1322 deforms when the wire 1310 is under tension, causing the tip 1312 to move upwards.

Figure 55:
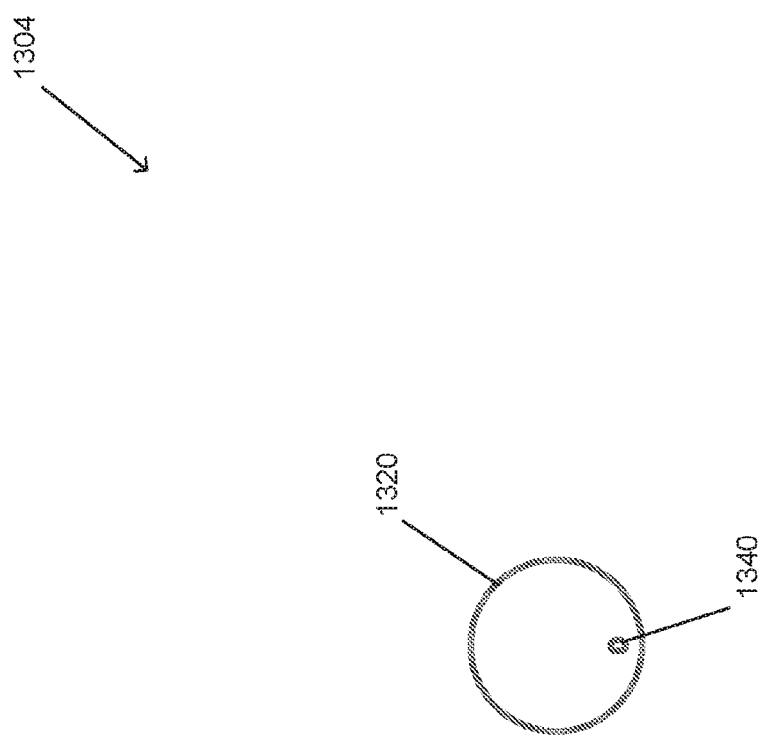
FIG. 55 shows a cross-sectional schematic diagram of an embodiment of the proximal shaft body portion.

FIG. 55 shows a cross-sectional schematic view of an embodiment of the proximal shaft body portion 1320. The proximal shaft body portion 1320 includes a lumen 1340. The lumen 1340 may be formed as a generally round recess in an extruded plastic structure. The lumen 1340 is configured to constrain the movement of the wire 1310. In other embodiments, more than one lumen 1340 may be present in the shaft body portion 1320.

Figure 56:
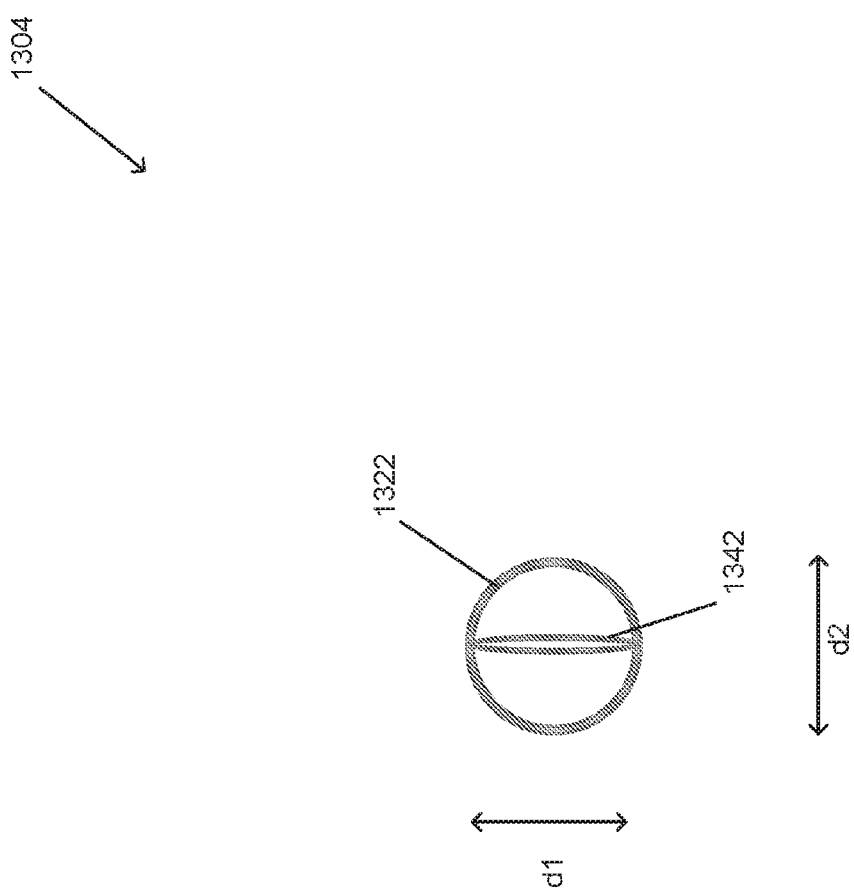
FIG. 56 is a cross-section schematic diagram of an embodiment of the proximal shaft tip portion.

Turning now to FIG. 56, a schematic diagram of an embodiment of the proximal shaft tip portion 1322 is illustrated in cross-section. The distal shaft body portion 1322 includes a lumen 1342. The lumen 1342 has an oblong shape that allows the wire 1310 to cross the distal shaft body portion 1322 in the dimension d1, while generally constraining the wire 1310 to the center of the distal shaft body portion 1322 in the dimension d2. In this manner, the wire 1310 causes the distal shaft body portion 1322 to deform in the dimension d1 when under tension.

Figure 57:
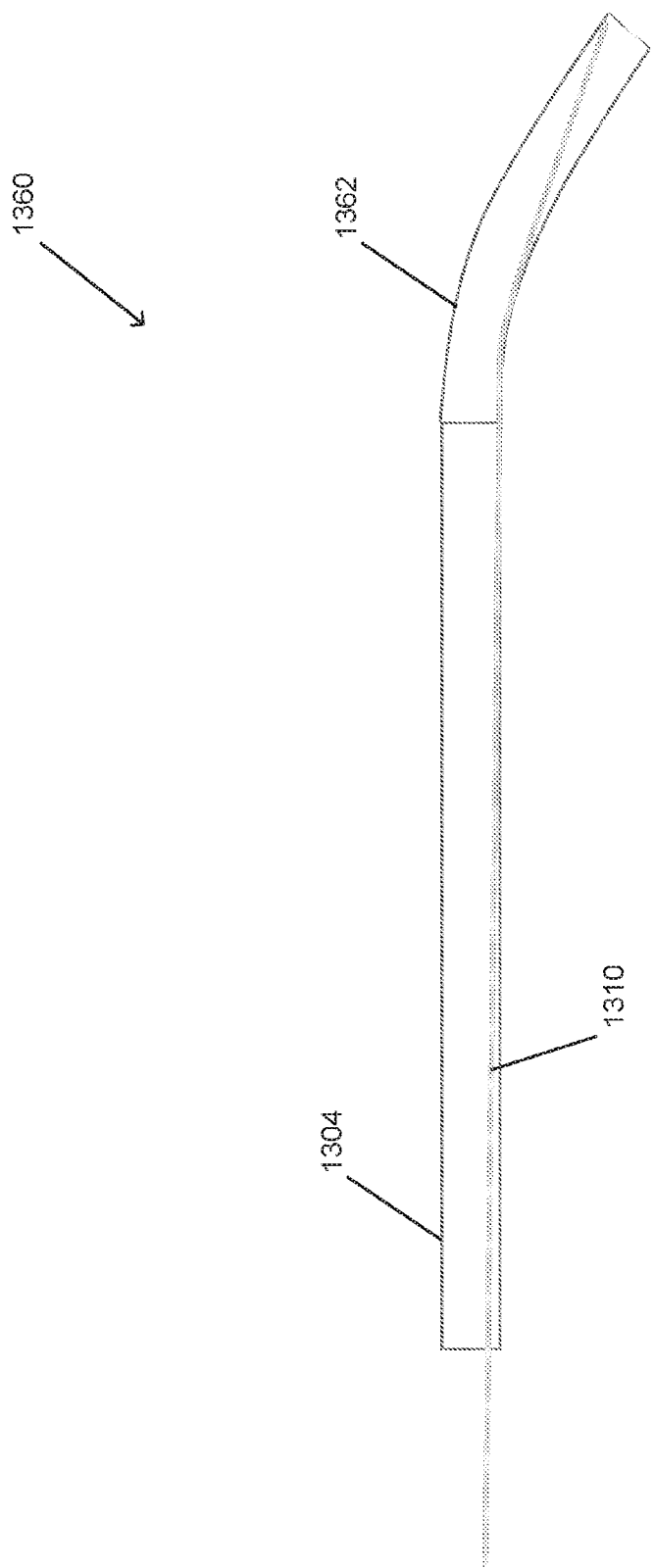
FIG. 57 is a schematic diagram of an alternative embodiment of a distal shaft portion when a wire is under tension.

Turning now to FIG. 57, an embodiment of a distal shaft portion 1360 is shown. The distal shaft portion 1360 may be used as an alternative to the previously described proximal shaft portion 1304 in the articulating stylet 1300. The distal shaft portion 1360 is similar to the previously described proximal shaft portion 1304 except that it includes a biased distal shaft tip portion 1362. The biased distal shaft tip portion 1362 is biased in one direction (e.g., a direction in dimension d1 as shown in FIG. 56). In some embodiments, the biased distal shaft tip portion 1362 is formed using a thermal molding process to have a bias in one direction. In this manner the tip 1312 of the articulating stylet 1300 is biased in a first direction when the wire 1310 is relaxed. When the wire 1310 is pulled and put under tension the tip 1312 moves in a direction opposite to the bias. This movement is illustrated further in the following figures.

Figure 58:
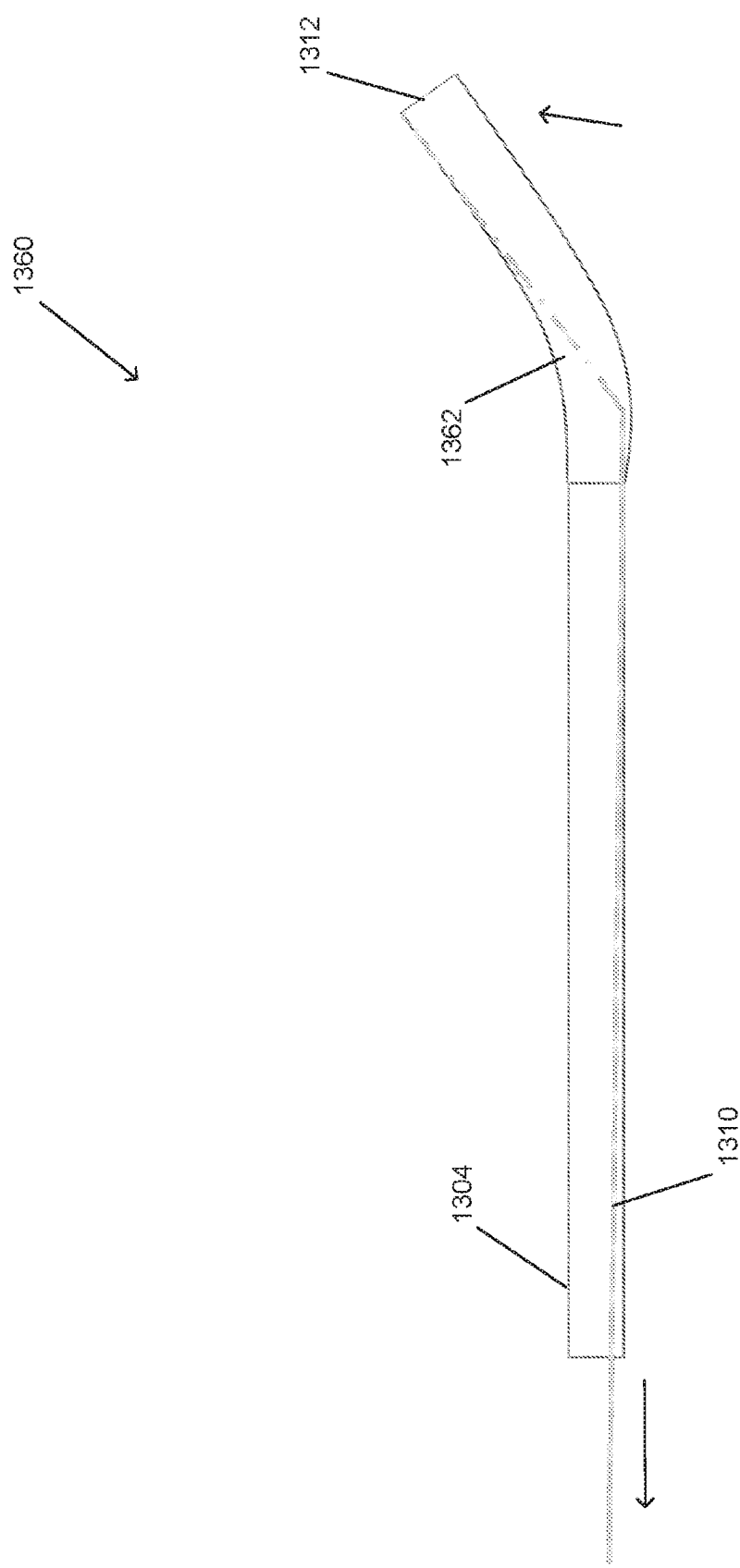
FIG. 58 is a schematic diagram of an embodiment of the distal shaft portion when the wire is under tension.

Turning now to FIG. 58, an embodiment of the distal shaft portion 1360 is illustrated when the wire 1310 is under tension. The wire 1310 is put under tension by being pulled away from the tip 1312 (e.g., when the expanding connector 1308 is expanded due to the distal shaft portion 1306 being pulled away from the proximal shaft portion 1304). When the wire is under tension, the articulating tip moves in a direction opposite the bias of the biased distal shaft tip portion 1362.

Figure 59:
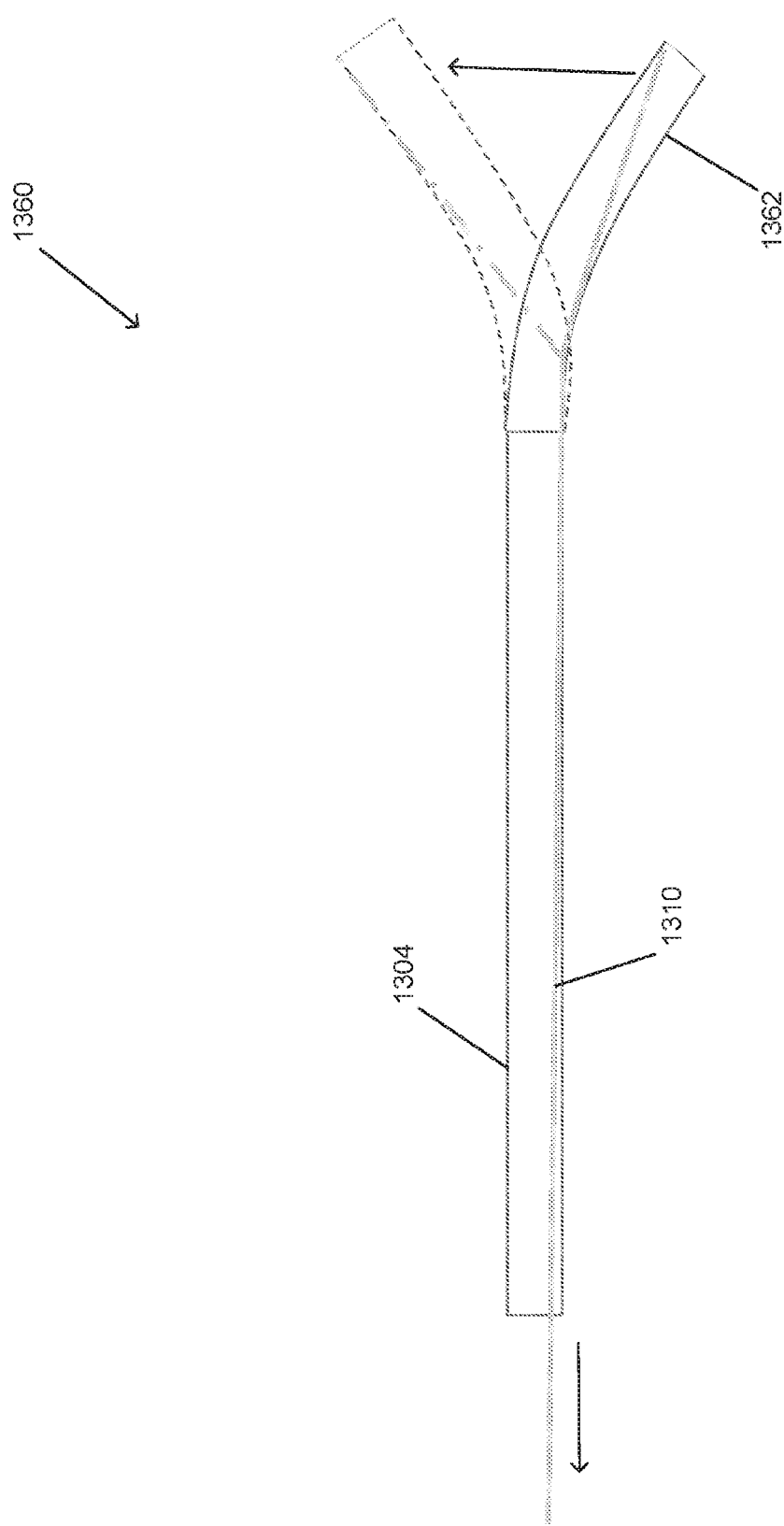
FIG. 59 is a schematic diagram illustrating an embodiment of the distal shaft portion in action as tension is applied to the wire.

Turning now to FIG. 59, a schematic diagram illustrating an embodiment of the distal shaft portion 1360 in action as tension is applied to the wire 1310 is shown. As shown in the figure, the biased distal shaft tip portion 1362 moves from a biased downward position to an upward position as the wire 1310 is put under tension by being pulled.

Figure 60:
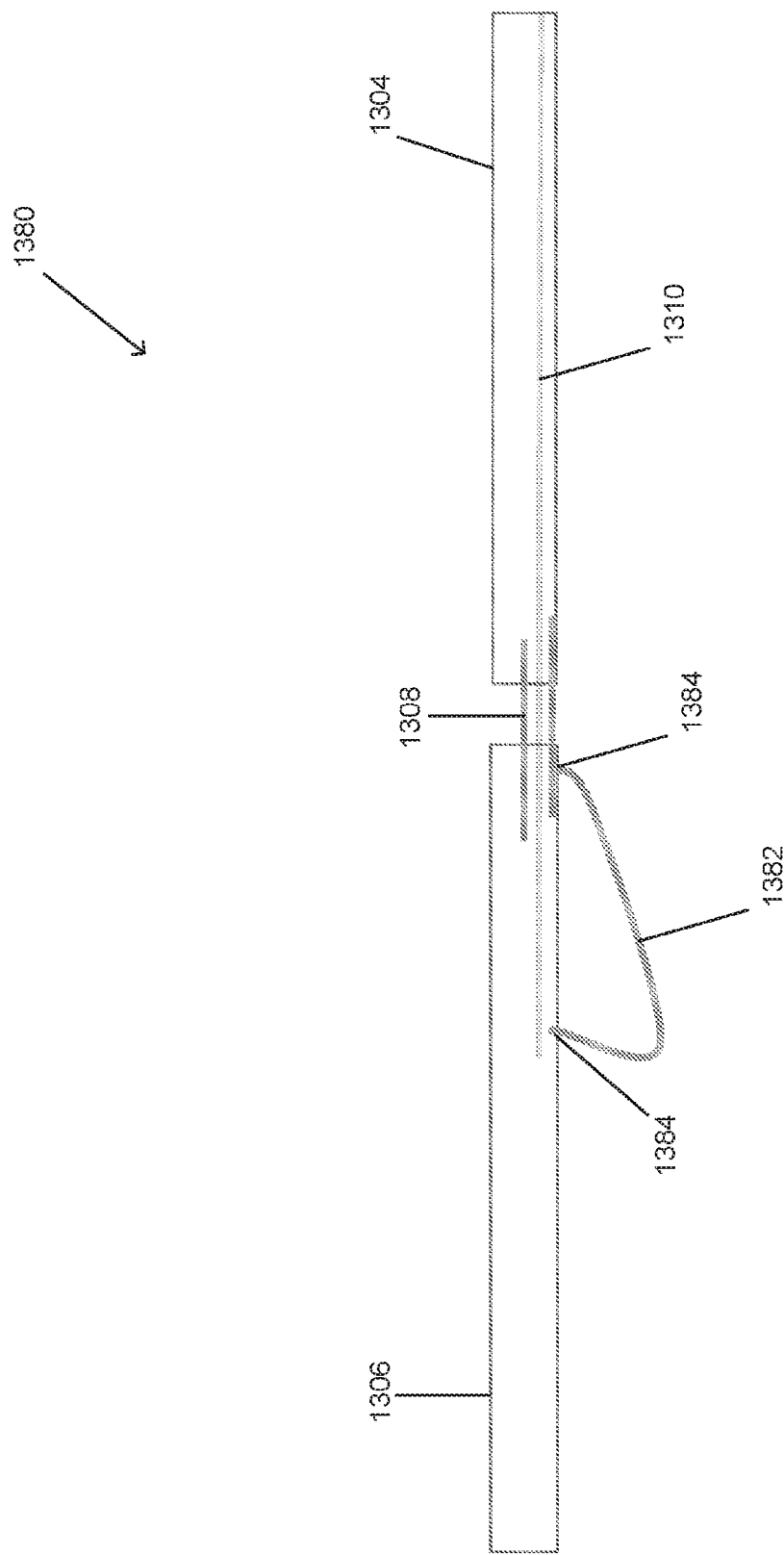
FIG. 60 is a schematic diagram of an embodiment of the articulating stylet.

Turning now to FIG. 60, a schematic diagram of an embodiment of an articulating stylet 1380 is shown. The articulating stylet 1380 is an example of the articulating stylet 1300. In this example the proximal shaft portion 1306 includes a handle 1382. The handle 1382 is joined to the proximal shaft portion 1306 by a connector assembly 1384, which may be an adhesive or a physical connector. In some embodiments, the handle 1382 is a collapsing thumb loop formed from a flexible material that is capable of being compressed to allow passage of an endotracheal tube or another type of device over the articulating stylet 1380.

Figure 61:
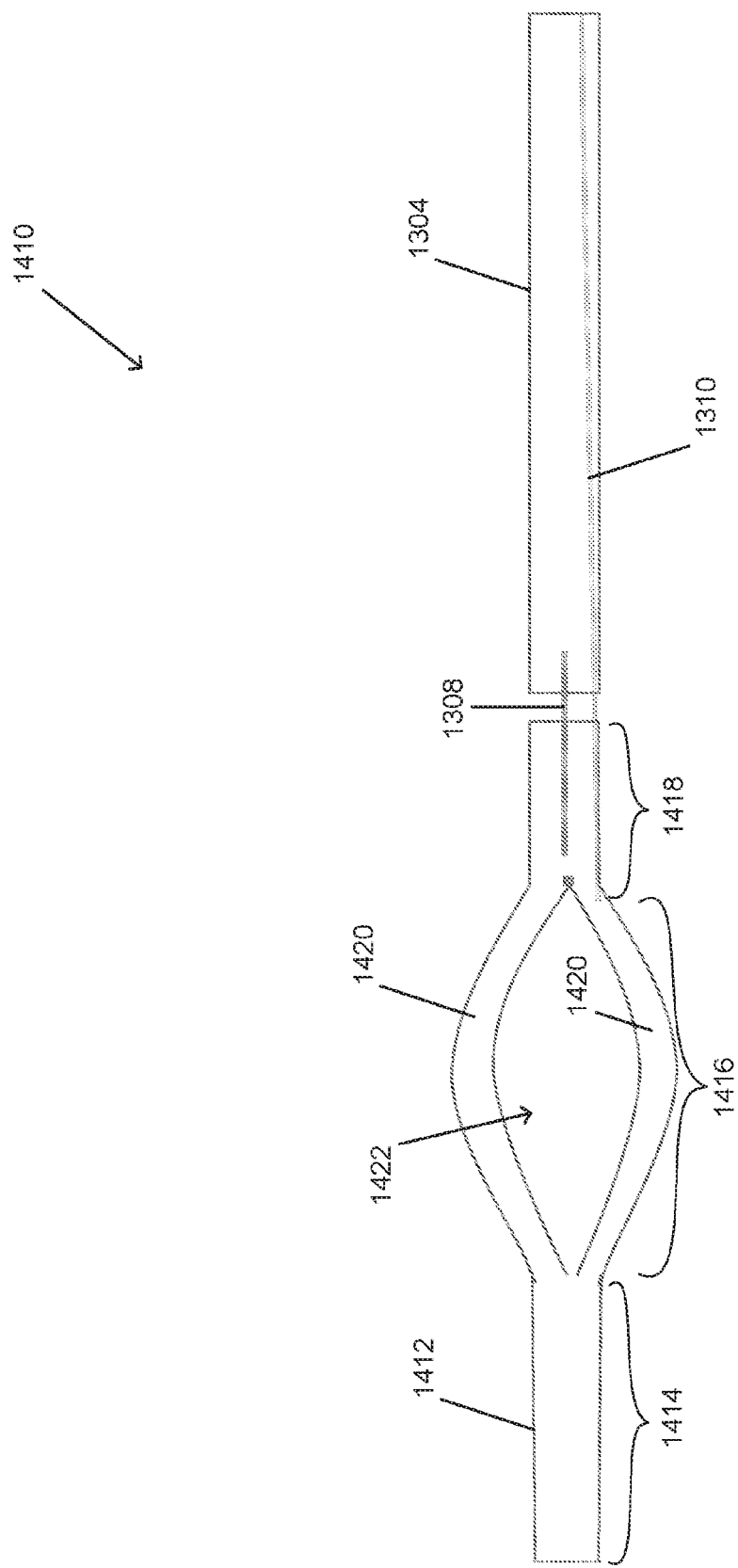
FIG. 61 is a schematic diagram of an embodiment of the articulating stylet.

Turning now to FIG. 61, a schematic diagram of an embodiment of an articulating stylet 1410 is shown. The articulating stylet 1410 includes a proximal shaft portion 1412. The proximal shaft portion 1412 includes a first region 1414, a second region 1416, and a third region 1418. The second region 1416 defines a split loop assembly 1420. As shown in the figure, the split loop assembly is formed by a split in the proximal shaft portion 1412 in the second region 1416 so that the distal shaft portion comprises two separate parts in the second region 1416. Between the two parts in the second region 1416, a grip aperture is formed through which a medical care professional may place a thumb or finger to pull the proximal shaft portion 1412 away from the distal shaft portion 1304.

Figure 62:
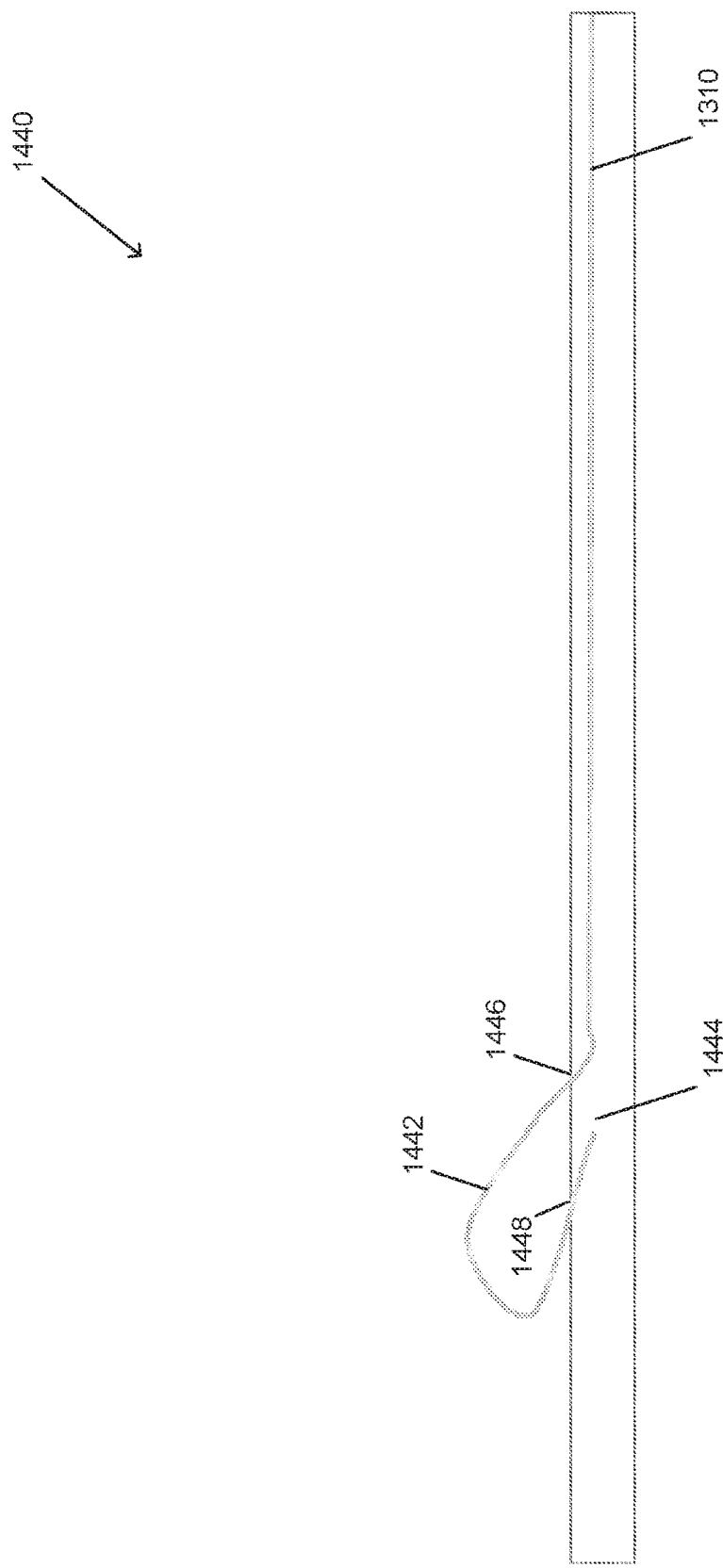
FIG. 62 is a schematic diagram of an embodiment of the articulating stylet.

Turning now to FIG. 62, a schematic diagram of an embodiment of a distal shaft portion 1440 is provided. The distal shaft portion 1440 is an example of the distal shaft portion 1306. The distal shaft portion 1440 includes a wire loop 1442 that is formed from an end of the wire 1310. As shown in this example, the wire 1310 emerges from the distal shaft portion 1440 through an aperture 1446 and forms a loop before a distal end 1444 of the wire 1310 re-enters the distal shaft portion 1440 at an aperture 1448. The distal end portion 1444 of the wire 1310 may be rigidly connected to the distal shaft portion 1440. The wire loop 1442 is a flexible loop in which a medical professional can insert a thumb or finder, to pull the distal shaft portion 1440 to pull away from the proximal shaft portion 1304 (which is not shown in this figure).

Figure 63:
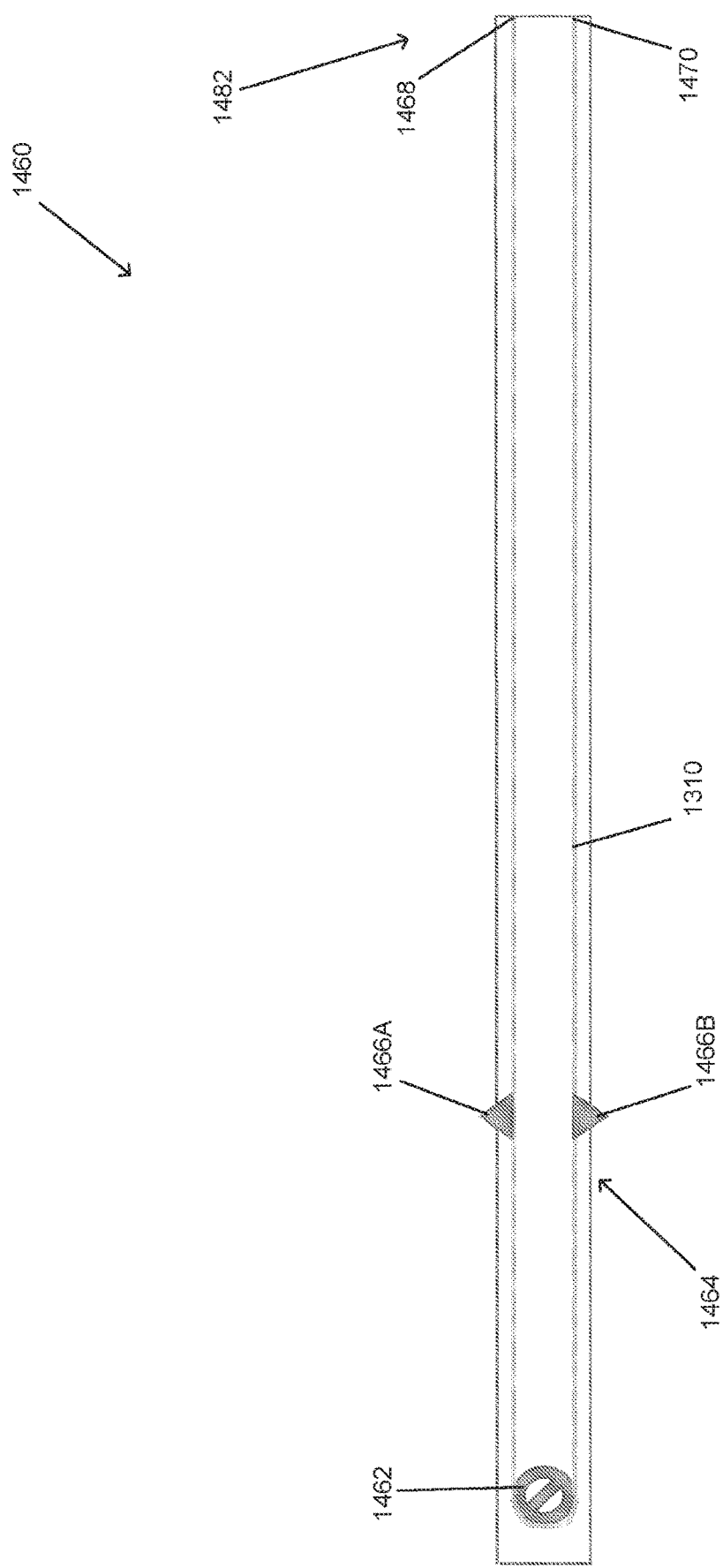
FIG. 63 is a schematic diagram of an embodiment of an articulating stylet.

Turning now to FIG. 63, a schematic diagram of an articulating stylet 1460 is shown. The articulating stylet 1460 allows for articulation of the tip in two directions and includes two connection points for the wire 1310 at the tip 1482. The wire 1310 connects at connection point 1468 on one side of the tip 1482 and at connection point 1470 on the other side of the tip 1482. The wire 1310 runs through the articulating stylet 1460 (e.g., in a first generally round lumen) to a distal end of an articulating stylet 1460 (e.g., in a second generally round lumen), where it is threaded through a pulley 1462 and then returns to the proximal end at connection point 1470. The articulating stylet 1460 also includes a pull assembly 1464, which allows a practitioner to pull on one or the other ends of the wire 1310 to control the movement of the tip 1482. The pull assembly includes tabs 1466A and 1466B that are configured to pull the wire 1310. As the wire is pulled (e.g., with a finger) using tab 1466A or tab 1466B, the tip 1482 will be deflected in the direction of the tab that is pulled.

Alternatively, the articulating stylet 1460 allows for articulation of the tip in two directions and includes two connection points for the wire 1310 at the tip 1482. The wire 1310 connects at connection point 1468 on one side of the tip 1482 and at connection point 1470 on the other side of the tip 1482. The wire 1310 runs through the articulating stylet 1460 (e.g., in a first generally round lumen) to a distal end of an articulating stylet 1460 (e.g., in a second generally round lumen) and then returns to the proximal end at connection point 1470, without the use of a pulley.

In yet another embodiment, the pull assembly includes tabs 1466A and 1466B that are configured to pull the wire 1310, wherein the tabs can fold toward the distal tip 148 as the endotracheal tube passes over the tabs 1466A, 1466B. As the wire is pulled (e.g., with a finger) using tab 1466A or tab 1466B, the tip 1482 will be deflected in the direction of the tab that is pulled.

Figure 64:
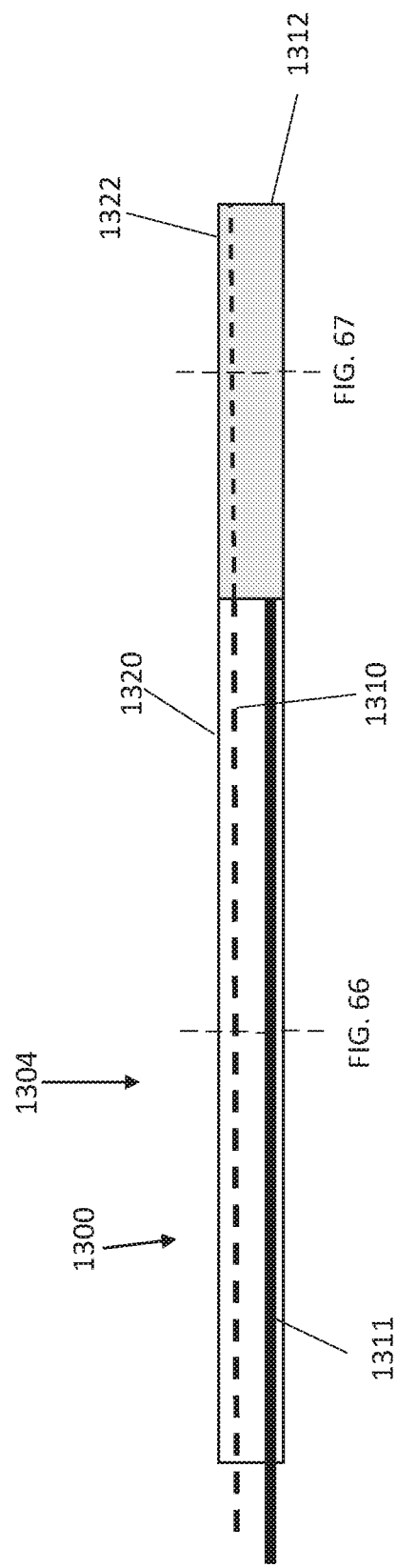
FIG. 64 is a schematic diagram of an embodiment of a distal shaft portion of an articulating stylet.

Referring now to FIG. 64, a schematic diagram of an embodiment of the proximal shaft portion 1304 of an articulating stylet 1300 is shown. In this example, the proximal shaft portion 1304 includes a proximal shaft body portion 1320 and a distal shaft tip portion 1322. The distal shaft tip portion 1322 is more flexible than the proximal shaft portion 1320. A stiffening wire 1311 extends through the proximal shaft body portion 1320, but does not extend through distal shaft tip 1322. Stiffening wire 1311 may be a carbon fiber wire, or made from other materials that are stiffer than wire 1310. Stiffening wire 1311 makes proximal shaft body portion 1320 more rigid than the distal shaft tip portion 1322. In other words, the distal shaft tip portion 1322 is more flexible than the proximal shaft portion 1320 because the stiffening wire 1311 does not extend into the distal shaft tip portion 1322. In this manner, when the wire 1310 is under tension from being pulled by the distal shaft portion 1306, the tension causes the more flexible distal shaft tip portion 1322 to deform, causing the tip 1312 to move. As shown in the example of FIG. 64, the wire 1310 is connected to an end of the tip 1312. As the wire 1310 is pulled, the tip is pulled towards the proximal shaft body portion 1320 in an L-shape. In some embodiments, the proximal shaft body portion 1320 and the distal shaft tip portion 1322 are formed integrally. Alternatively, the proximal shaft body portion 1320 and the distal shaft tip portion 1322 are formed separately and joined together (e.g., with a weld such as a butt weld, an adhesive, or a coupling device). Cross sections of the proximal shaft body portion 1320 and the proximal shaft tip portion are illustrated further in FIGS. 66 and 67 respectively.

Figure 65:
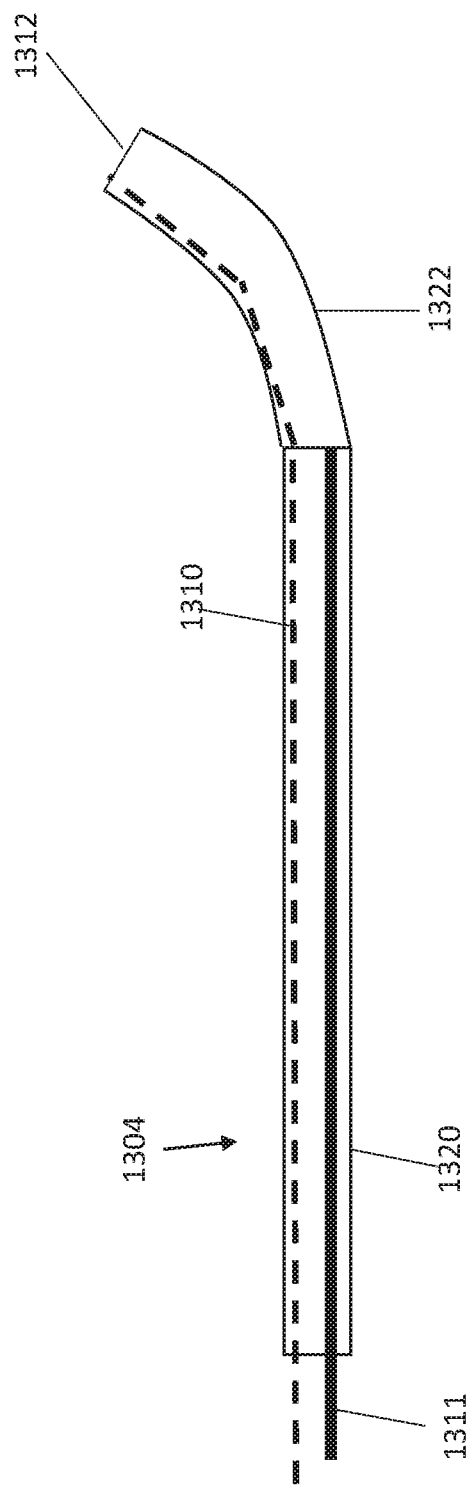
FIG. 65 is a schematic diagram of an embodiment of a distal shaft portion when a wire is under tension.

FIG. 65 illustrates an embodiment of the proximal shaft portion 1304 is illustrated when the wire 1310 is under tension. As described previously, the distal shaft tip portion 1322 deforms when the wire 1310 is under tension, causing the tip 1312 to move upwards.

Figure 66:
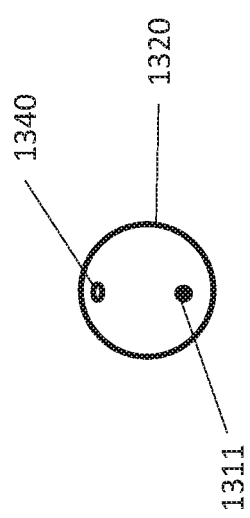
FIG. 66 shows a cross-sectional schematic diagram of an embodiment of the distal shaft body portion.

FIG. 66 shows a cross-sectional view of an embodiment of the proximal shaft body portion 1320. The proximal shaft body portion 1320 includes a lumen 1340. The lumen 1340 may be formed as a generally round recess in an extruded plastic structure. The lumen 1340 is configured to constrain the movement of the wire 1310. The proximal shaft body portion 1320 also includes stiffening wire 1311.

Figure 67:
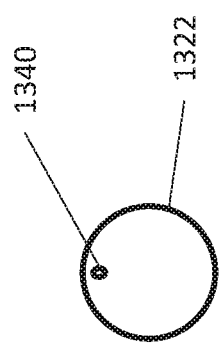
FIG. 67 is a cross-section schematic diagram of an embodiment of the distal shaft tip portion.

FIG. 67 illustrates a schematic diagram of an embodiment of the proximal shaft tip portion 1322 in cross-section. The distal shaft tip portion 1322 includes a lumen 1340. Wire 1310 extends through lumen 1340.

Figure 68:
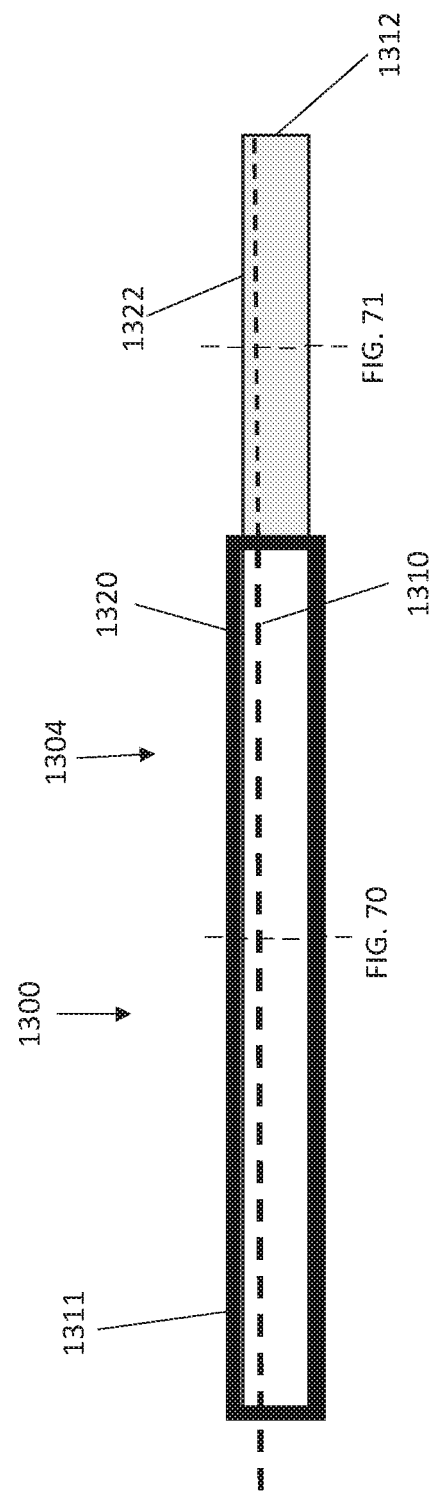
FIG. 68 is a schematic diagram of an embodiment of a distal shaft portion of an articulating stylet.

FIG. 68 illustrates a schematic diagram of an embodiment of the proximal shaft portion 1304 of an articulating stylet 1300 is shown. In this example, the proximal shaft portion 1304 includes a proximal shaft body portion 1320 and a distal shaft tip portion 1322. In some embodiments, the proximal shaft body portion 1320 is more rigid than the distal shaft tip portion 1322. In other words, the distal shaft tip portion 1322 is more flexible than the proximal shaft portion 1320. For example, the proximal shaft body portion 1320 is wrapped with a wrapping 1311 that is made from a material more rigid than a material the articulating stylet 1300 is made from. Materials such as shrink wrap may be used as wrapping 1311. In this manner, when the wire 1310 under tension from being pulled by the distal shaft portion 1306, the tension causes the more flexible distal shaft tip portion 1322 to deform, causing the tip 1312 to move. As shown in the example of FIG. 68, the wire 1310 is connected to an end of the tip 1312. As the wire 1310 is pulled, the tip is pulled towards the shaft body portion 1320 in an L-shape. In some embodiments, the proximal shaft body portion 1320 and the distal shaft tip portion 1322 are formed integrally. Alternatively, the proximal shaft body portion 1320 and the distal shaft tip portion 1322 are formed separately and joined together (e.g., with a weld such as a butt weld, an adhesive, or a coupling device). Cross sections of the proximal shaft body portion 1320 and the proximal shaft tip portion are illustrated further in FIGS. 70 and 71 respectively.

Figure 69:
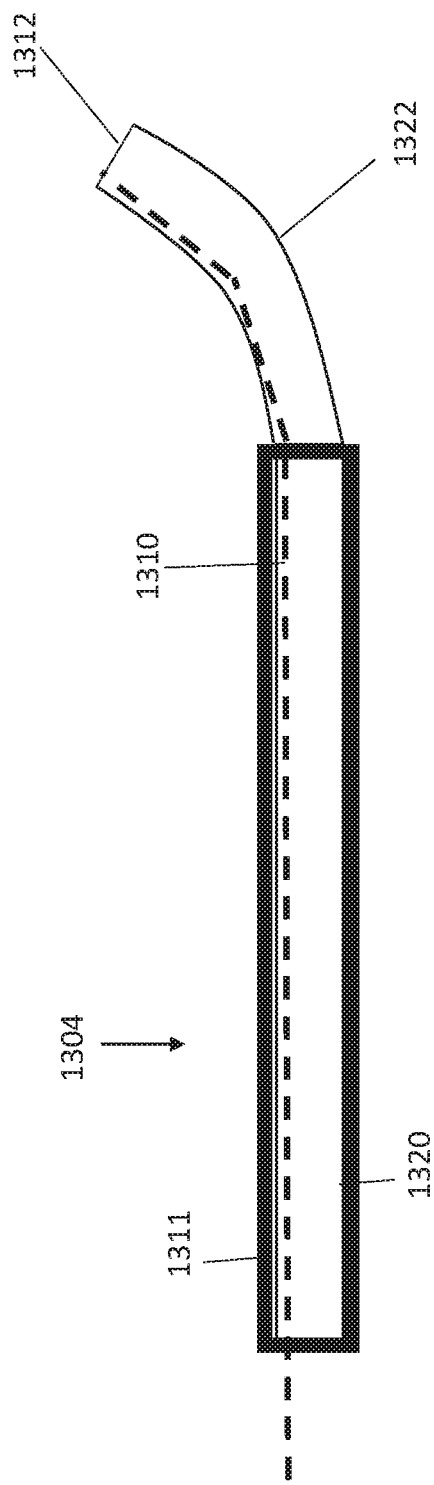
FIG. 69 is a schematic diagram of an embodiment of a distal shaft portion when a wire is under tension.

Turning now to FIG. 69, an embodiment of the proximal shaft portion 1304 is illustrated when the wire 1310 is under tension. As described previously, the distal shaft tip portion 1322 deforms when the wire 1310 is under tension, causing the tip 1312 to move upwards.

Figure 70:
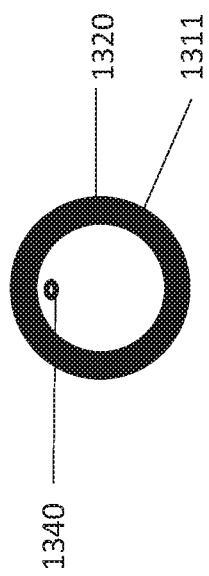
FIG. 70 shows a cross-sectional schematic diagram of an embodiment of the shaft body portion.

FIG. 70 shows a cross-sectional schematic view of an embodiment of the proximal shaft body portion 1320. The proximal shaft body portion 1320 includes wrapping 1311, which circumvents proximal shaft body portion 1320. The proximal shaft body portion 1320 also includes a lumen 1340. The lumen 1340 may be formed as a generally round recess in an extruded plastic structure. The lumen 1340 is configured to constrain the movement of the wire 1310.

Figure 71:
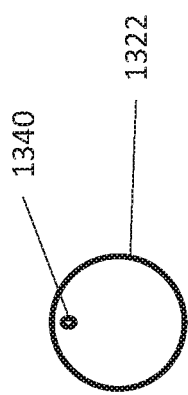
FIG. 71 is a cross-section schematic diagram of an embodiment of the distal shaft tip portion.

Turning now to FIG. 71, a schematic diagram of an embodiment of the proximal shaft tip portion 1322 is illustrated in cross-section. The proximal shaft tip portion 1322 includes a lumen 1340 through which wire 1310 extends.

Figure 72:
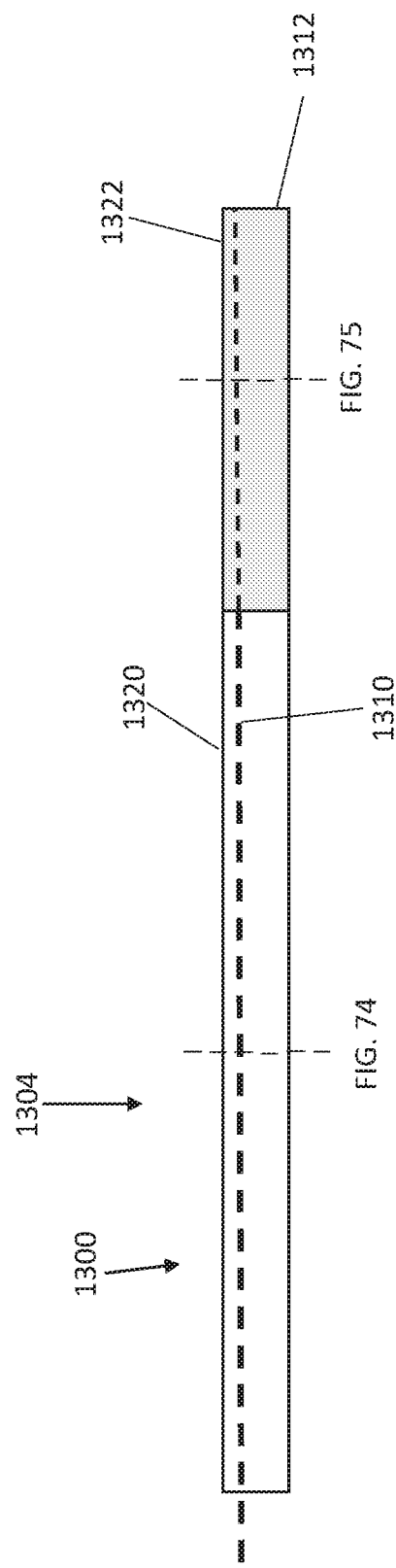
FIG. 72 is a schematic diagram of an embodiment of a distal shaft portion of an articulating stylet.

Referring now to FIG. 72, a schematic diagram of an embodiment of the proximal shaft portion 1304 of an articulating stylet 1300 is shown. In this example, the proximal shaft portion 1304 includes a proximal shaft body portion 1320 and a distal shaft tip portion 1322. In some embodiments, the proximal shaft body portion 1320 is more rigid than the distal shaft tip portion 1322. In other words, the distal shaft tip portion 1322 is more flexible than the proximal shaft portion 1320. For example, the proximal shaft body portion 1320 may be formed from a material such as a plastic or epoxy that upon exposure to an external source becomes stiffer than the distal shaft tip portion 1322. Example materials may be a photopolymer or a light-activated resin. An external source that causes proximal shaft body portion 1320 to become stiffer may be water, UV light, or similar additive. The distal shaft tip portion 1322 is formed from a more flexible material. In this manner, when the wire 1310 is under tension from being pulled, the tension causes the more flexible distal shaft tip portion 1322 to deform, causing the tip 1312 to move. As shown in the example of FIG. 72, the wire 1310 is connected to an end of the tip 1312. The wire 1310 extends in a generally straight direction from proximal shaft portion 1304 to and end of the tip 1312. As the wire 1310 is pulled, the tip is pulled towards the shaft body portion 1320 in an L-shape. In some embodiments, the proximal shaft body portion 1320 and the distal shaft tip portion 1322 are formed integrally. Alternatively, the proximal shaft body portion 1320 and the distal shaft tip portion 1322 are formed separately and joined together (e.g., with a weld such as a butt weld, an adhesive, or a coupling device). Cross sections of the proximal shaft body portion 1320 and the proximal shaft tip portion are illustrated further in FIGS. 74 and 75 respectively.

Figure 73:
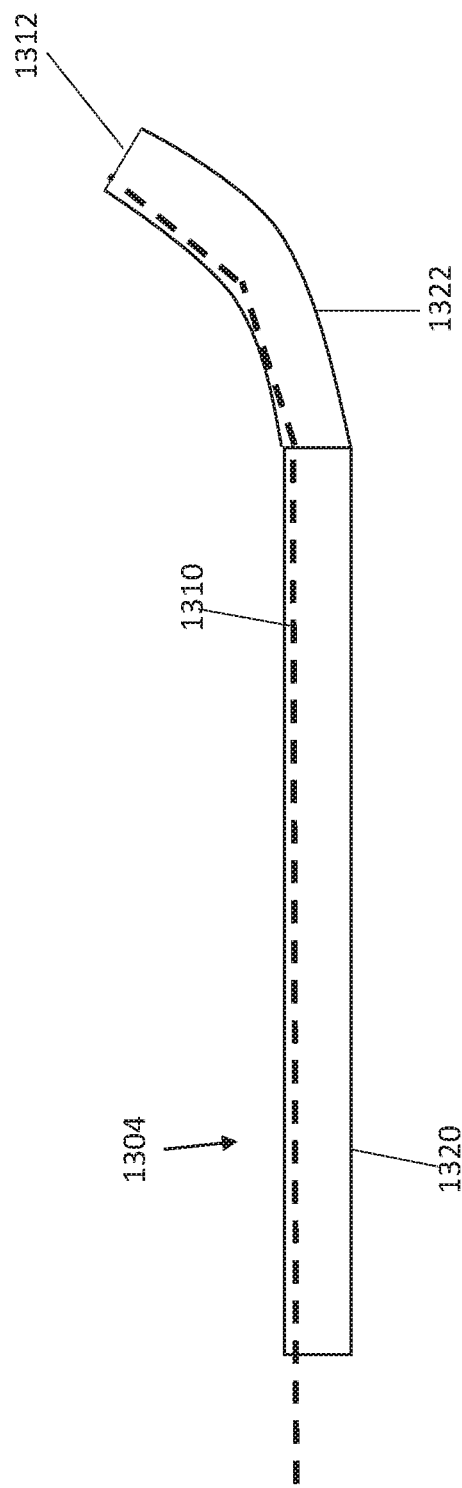
FIG. 73 is a schematic diagram of an embodiment of a distal shaft portion when a wire is under tension.

FIG. 73 illustrates an embodiment of the proximal shaft portion 1304 is illustrated when the wire 1310 is under tension. As described previously, the distal shaft tip portion 1322 deforms when the wire 1310 is under tension, causing the tip 1312 to move upwards.

Figure 74:
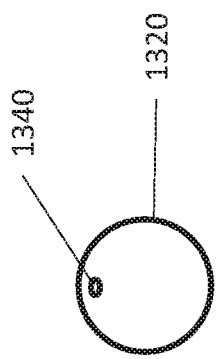
FIG. 74 shows a cross-sectional schematic diagram of an embodiment of the shaft body portion.

FIG. 74 shows a cross-sectional view of an embodiment of the proximal shaft body portion 1320. The proximal shaft body portion 1320 includes a lumen 1340. The lumen 1340 may be formed as a generally round recess in an extruded plastic structure. The lumen 1340 is configured to constrain the movement of the wire 1310.

Figure 75:
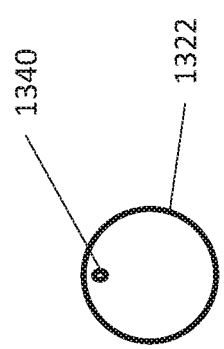
FIG. 75 is a cross-section schematic diagram of an embodiment of the proximal shaft tip portion.

FIG. 75 illustrates a schematic diagram of an embodiment of the distal shaft tip portion 1322 in cross-section. The distal shaft tip portion 1322 includes a lumen 1340. Wire 1310 extends through lumen 1340.

Figure 76:
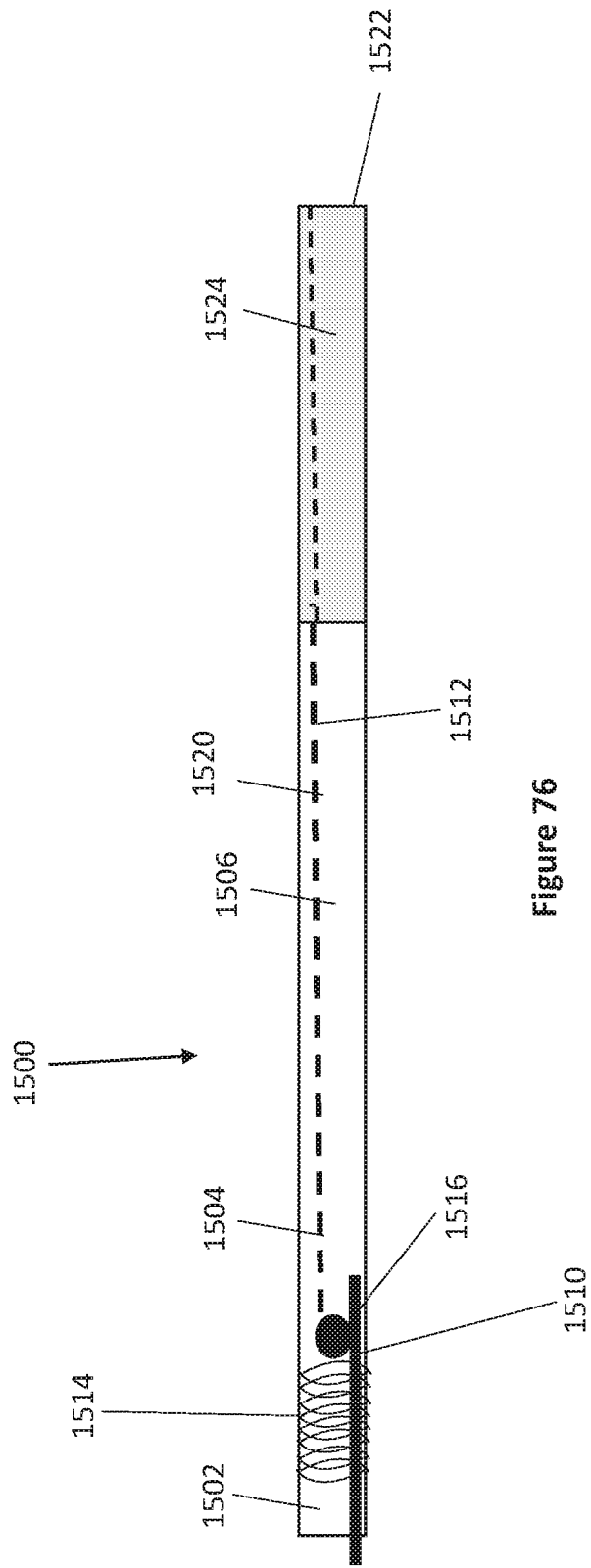
FIG. 76 is a cross-sectional schematic diagram of an embodiment of the distal shaft portion.

FIG. 76 illustrates a schematic diagram of an embodiment of an articulating stylet 1500. The articulating stylet 1500 allows for control of a tip 1522. The articulating stylet 1500 includes a lumen 1520 through which a pull string 1512 extends from the tip 1522 to the proximal shaft portion 1504. A push rod 1510 is attached to the pull string 1512 at a proximal end. The pull string 1512 extends around a pulley 1516 and is attached to the pull string 1512. The push rod 1510 is attached to a spring 1514 at an opposing end. The spring 1514 is located within the lumen 1520 at the proximal shaft end 1502. The articulating stylet 1500 has a first state where the tip is relaxed, or straight relative to the shaft 1506.

Figure 77:
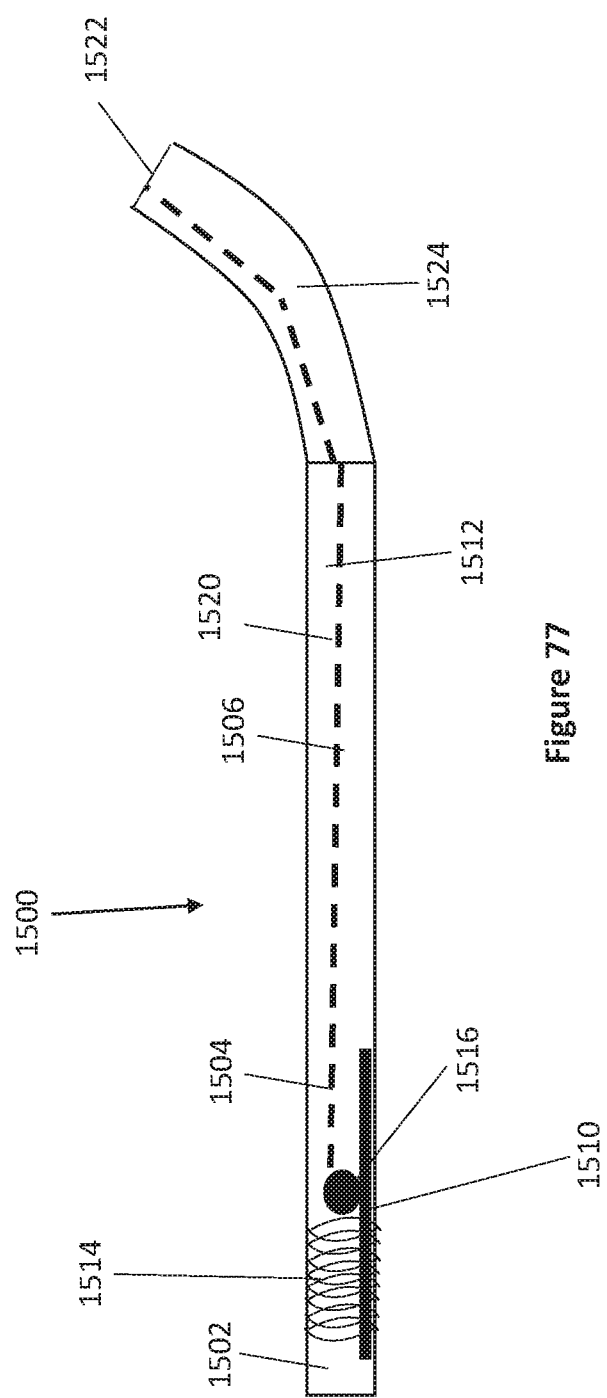
FIG. 77 is a schematic diagram of an embodiment of a distal shaft portion when a wire is under tension.

As shown in FIG. 77, the articulating stylet 1500 has a second state where the tip 1522 is deformed when the pull string 1512 is under tension, causing the tip 1522 to move upwards. When the push rod 1510 is pushed, it causes the pull string 1512 to retract the tip 1522 into the deformed position.

Figure 78:
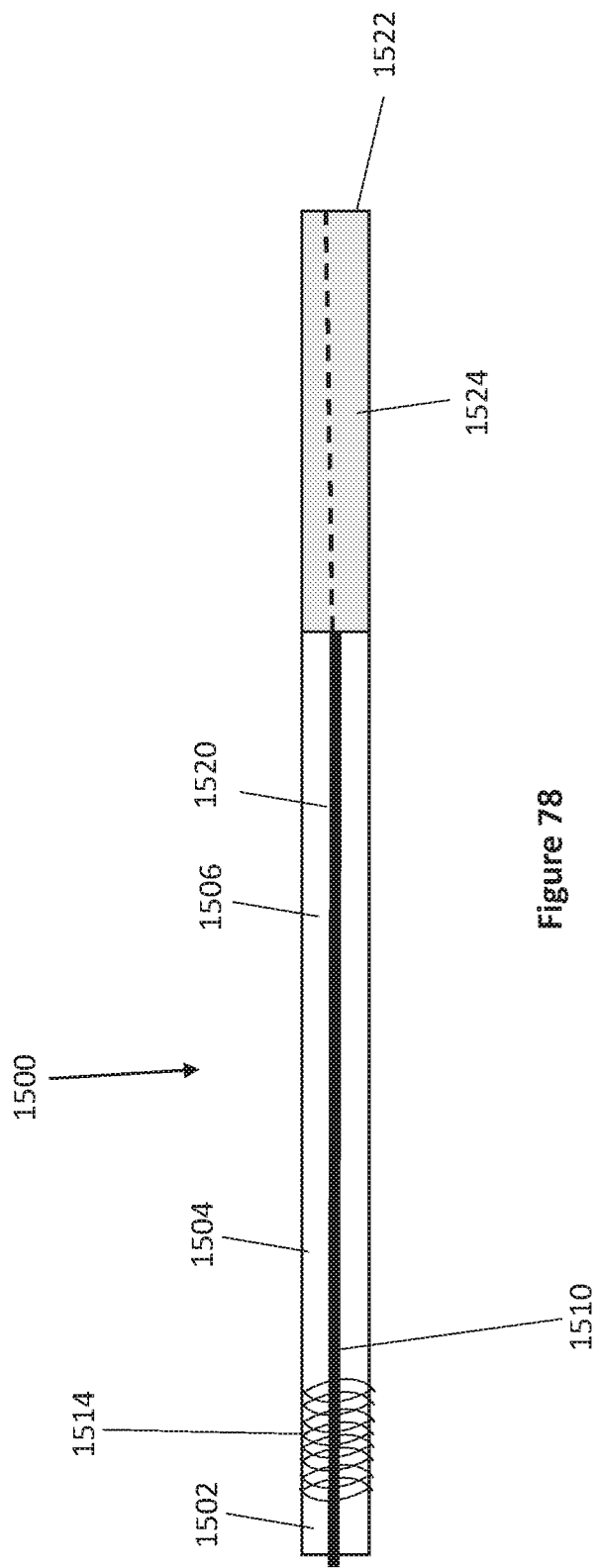
FIG. 78 is a cross-sectional schematic diagram of an embodiment of the distal shaft portion.

FIG. 78 illustrates a schematic diagram of an embodiment of an articulating stylet 1500. The articulating stylet 1500 allows for control of a tip 1522. The articulating stylet 1500 includes a lumen 1520 through which a push rod 1510 extends from the tip 1522 to the proximal shaft portion 1504. The push rod 1510 extends along a spring 1514 at the proximal end. The spring 1514 is located within the lumen 1520 at the proximal shaft end 1502. The articulating stylet 1500 has a first state where the tip is relaxed, or straight relative to the shaft 1506.

Figure 79:
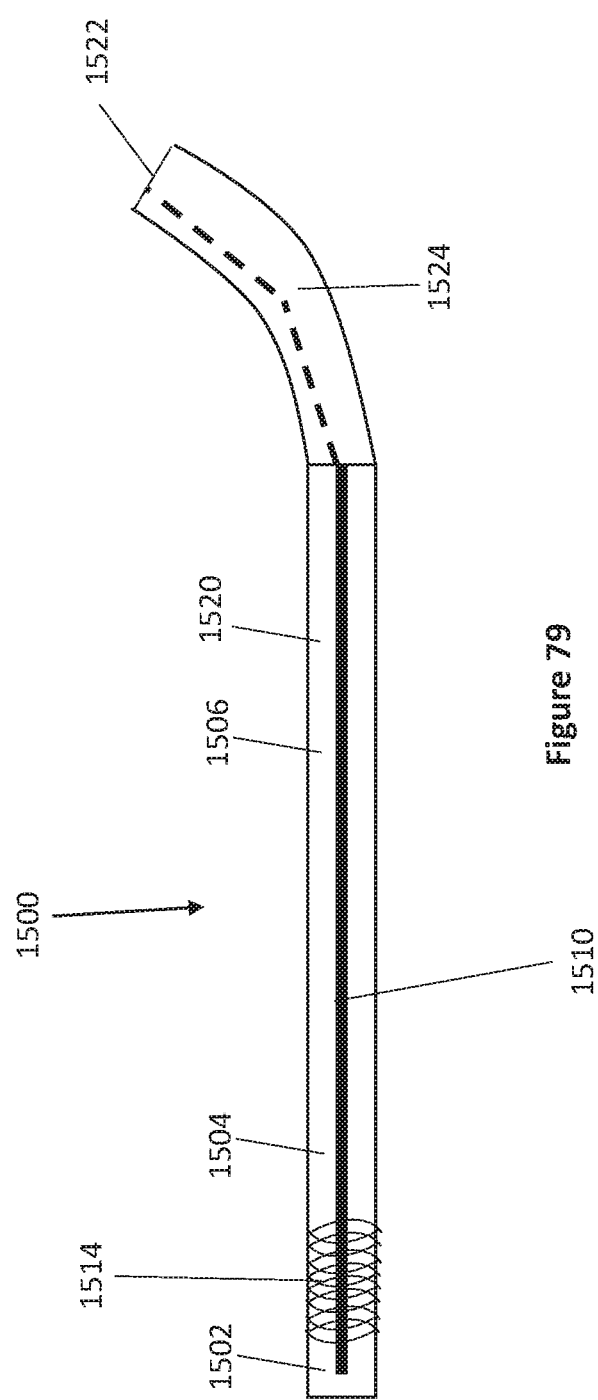
FIG. 79 is a schematic diagram of an embodiment of a distal shaft portion when a wire is under tension.

As shown in FIG. 79 the articulating stylet 1500 has a second state where the tip 1522 is deformed when the push rod 1510 is pushed it causes the tip 1522 to retract into the deformed position.

Figure 80:
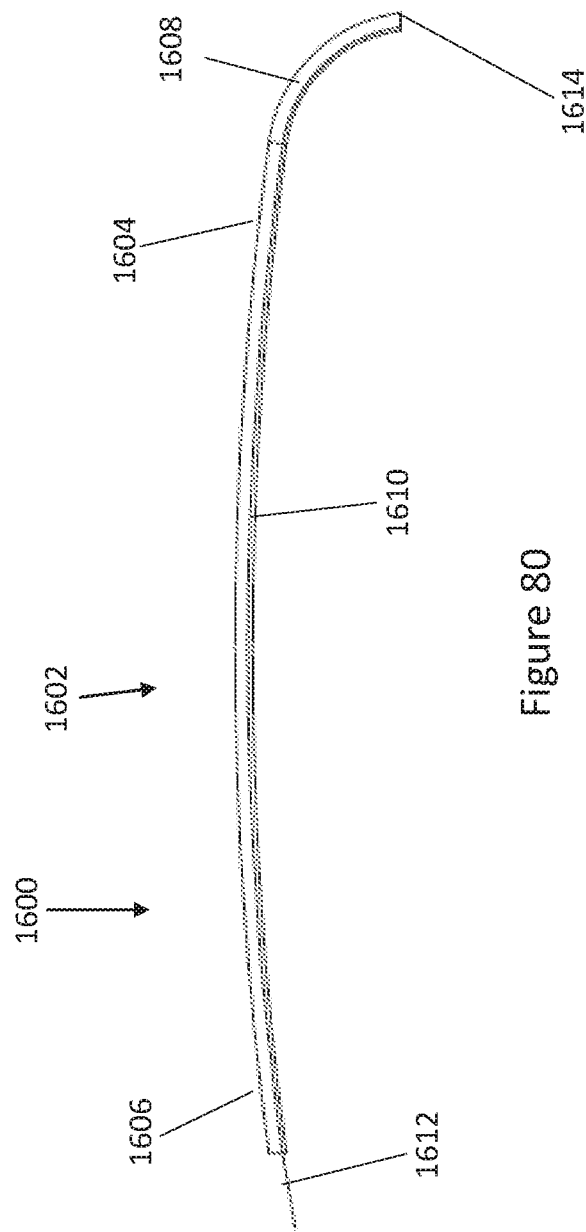
FIG. 80 is a schematic diagram of an embodiment of the articulating stylet.

Turning now to FIG. 80, a schematic diagram of an embodiment of the distal shaft portion 1602 of an articulating stylet 1600 is shown. In this example, the distal shaft portion 1602 includes a proximal shaft body portion 1606 and a distal shaft portion 1608. In some embodiments, the proximal shaft body portion 1606 is more rigid than the distal shaft portion 1608. In other words, the distal shaft tip portion 1614 is more flexible than the proximal shaft portion 1606. The flexibility of the distal shaft portion 1602 may change once or may change more than once, over the length of the distal shaft portion 1602. For example, the proximal shaft body portion 1606 may have a flexibility that is greater than medial shaft portion 1610 but less than the flexibility of the distal shaft portion 1608. In this manner, when the wire 1610 is under tension from being pulled by the proximal shaft body portion 1606, the tension causes the more flexible distal shaft portion 1608 to deform, causing the tip 1614 to move. Advantageously, the flexibility of the distal shaft portion 1602 conforms to the anatomy of an upper airway of a patient.

Figure 81:
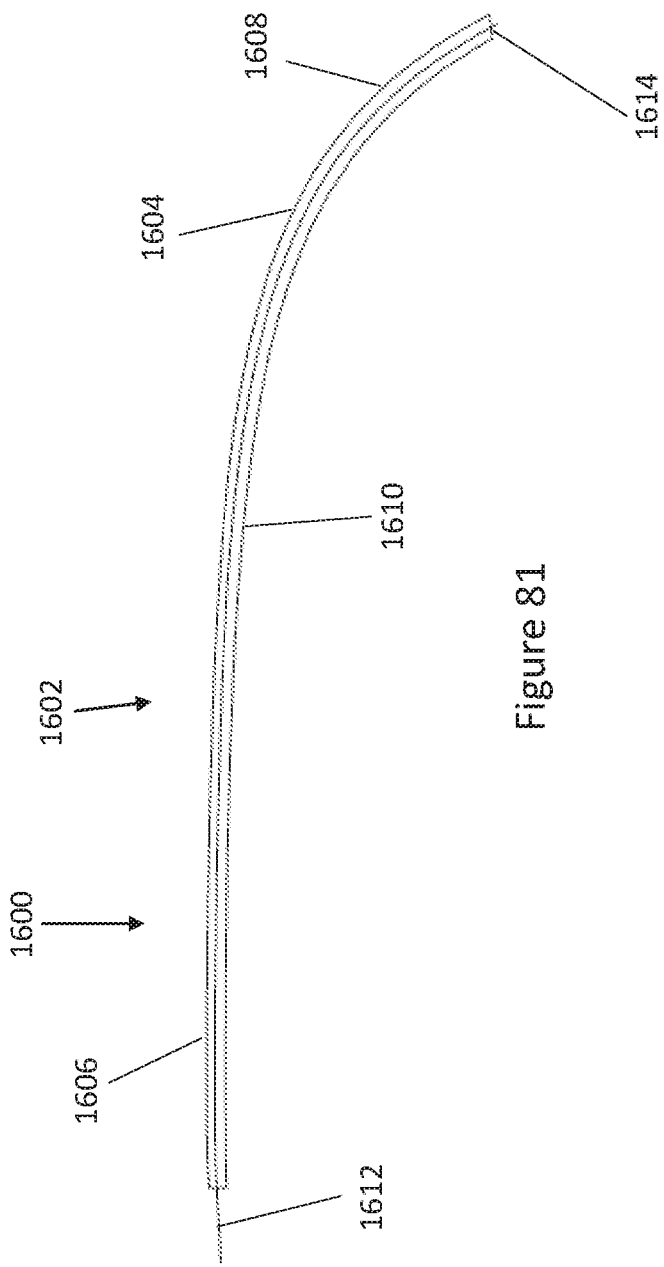
FIG. 81 is a schematic diagram of an embodiment of the articulating stylet.

Turning now to FIG. 81, a schematic diagram of an embodiment of the distal shaft portion 1602 of an articulating stylet 1600 is shown. In this example, the distal shaft portion 1602 includes a proximal shaft body portion 1606 and a distal shaft portion 1608. In some embodiments, the proximal shaft body portion 1606 is more rigid than the distal shaft portion 1608. In other words, the distal shaft tip portion 1614 is more flexible than the proximal shaft portion 1606. For example, the distal shaft portion 1602 may have a gradient or spectrum of flexibility. The distal shaft portion 1602 may have a linear gradient of flexibility, or alternatively, may have a non-linear gradient of flexibility. The flexibility of the distal shaft portion 1602 may change continuously, and at different rates over the length of the distal shaft portion 1602. For example, the proximal shaft body portion 1606 may have a flexibility that is greater than medial shaft portion 1610 but less than the flexibility of the distal shaft portion 1608. In this manner, when the wire 1610 is under tension from being pulled by the proximal shaft body portion 1606, the tension causes the more flexible distal shaft portion 1608 to deform, causing the tip 1614 to move.

Figure 82:
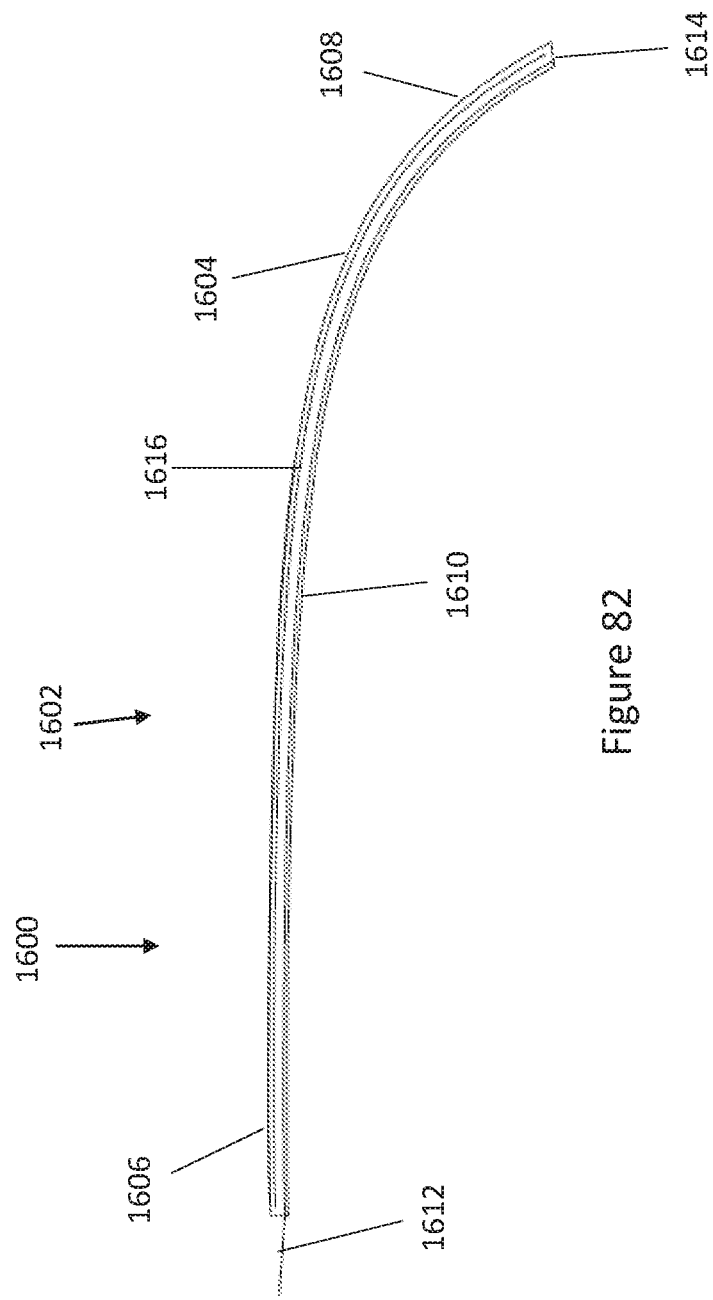
FIG. 82 is a schematic diagram of an embodiment of an articulating stylet.

Turning now to FIG. 82, a schematic diagram of an embodiment of the distal shaft portion 1602 of an articulating stylet 1600 is shown. In this example, the distal shaft portion 1602 includes a proximal shaft body portion 1606 and a distal shaft portion 1608. A stiffening wire 1616 extends through the distal shaft portion 1602. Stiffening wire 1616 may be a carbon fiber wire, or made from other materials that allows for a gradient or spectrum of flexibility. Stiffening wire 1616 makes proximal shaft body portion 1606 more rigid than the distal shaft portion 1608. The stiffening wire 1616 may have a linear gradient of flexibility, or alternatively, may have a non-linear gradient of flexibility. The stiffening wire 1616 causes the flexibility of the distal shaft portion 1602 to change continuously, or at different rates over the length of the distal shaft portion 1602. For example, the stiffening wire 1616 provides for the proximal shaft body portion 1606 to have flexibility that is greater than medial shaft portion 1610 but less than the flexibility of the distal shaft portion 1608. In this manner, when the wire 1610 is under tension from being pulled by the proximal shaft body portion 1606, the tension causes the more flexible distal shaft portion 1608 to deform, causing the tip 1614 to move.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:
1. A stylet adapted for mounting an endotracheal tube comprising:
   a shaft comprising:
      a proximal shaft portion;
      a distal shaft portion, the distal shaft portion having a body portion and a tip portion, the tip portion having greater flexibility than the body portion;
      an expanding connector which includes a sliding assembly to connect the proximal shaft portion to the distal shaft portion across a distance, the expanding connector configured to adjust the distance between the proximal shaft portion and the distal shaft portion;
      a control wire at least partially disposed within the proximal shaft portion and the distal shaft portion and configured to cause the tip portion of the distal shaft portion to deform in response to a change in the distance between the proximal shaft portion and the distal shaft portion; and
   a handle loop joined to the body portion of the proximal shaft portion, the handle loop comprising: a flexible material such that the handle loop may be compressed to allow passage of the endotracheal tube over the stylet from a proximal end of the stylet to a distal end of the stylet before returning to an original shape.

2. The stylet of claim 1, wherein the tip portion is biased in a first direction and the control wire is configured to cause the tip portion to deform in a second direction that is opposite the first direction.

3. The stylet of claim 1, wherein the body portion is made from a material that has a stiffness greater than a stiffness of the tip portion.

4. The stylet of claim 3, wherein the body portion is made from a material selected from a photopolymer and a light-activated resin.

5. The stylet of claim 3, wherein the body portion further comprises a stiffening material located on an external surface.

6. The stylet of claim 5, wherein the tip portion does not comprise the stiffening material located on an external surface.

7. The stylet of claim 1, wherein the distal shaft portion further comprises a stiffening wire extending through the body portion and not through the tip portion.

8. The stylet of claim 1, wherein the body portion comprises a lumen, and the control wire is located within the lumen of the body portion and is moveable within the lumen.

9. The stylet of claim 8, wherein the sliding assembly comprises one or more pins disposed in the lumen.

10. The stylet of claim 1, wherein the control wire is fixedly connected to the tip portion of the distal shaft portion and the proximal shaft portion.

11. The stylet of claim 1, wherein the proximal shaft portion comprises a proximal end and a distal end, the distal end abutting the expanding connector, and wherein the distal end of the proximal shaft portion comprises an indentation.

12. The stylet of claim 1, wherein the control wire is fixedly connected with the tip portion at a first end and fixedly connected to the proximal shaft portion at a second end.

* * * * *